(12) United States Patent
Edwards et al.

(10) Patent No.: US 7,648,482 B2
(45) Date of Patent: *Jan. 19, 2010

(54) DEVICES, SYSTEMS, AND METHODS FOR MEDICAMENT DELIVERY

(75) Inventors: Evan Thomas Edwards, Fredericksburg, VA (US); Eric Shawn Edwards, Midlothian, VA (US); Mark J. Licata, Doswell, VA (US)

(73) Assignee: Intelliject, Inc., Richmond, VA (US)

( * ) Notice: Subject to any disclaimer, the term of this patent is extended or adjusted under 35 U.S.C. 154(b) by 317 days.

This patent is subject to a terminal disclaimer.

(21) Appl. No.: 11/562,061

(22) Filed: Nov. 21, 2006

(65) Prior Publication Data

US 2007/0149925 A1 Jun. 28, 2007

Related U.S. Application Data

(63) Continuation-in-part of application No. 10/515,571, filed as application No. PCT/US2004/039386 on Nov. 23, 2004, now Pat. No. 7,416,540, application No. 11/562,061, which is a continuation-in-part of application No. 10/572,148, filed as application No. PCT/US2006/003415 on Feb. 1, 2006.

(60) Provisional application No. 60/648,822, filed on Feb. 1, 2005, provisional application No. 60/731,886, filed on Oct. 31, 2005.

(51) Int. Cl.
*A61M 5/20* (2006.01)
(52) U.S. Cl. ...................................... 604/136; 604/140
(58) Field of Classification Search ................ 604/131, 604/136, 141, 140

See application file for complete search history.

(56) References Cited

U.S. PATENT DOCUMENTS

| 2,960,087 | A | 11/1960 | Uytenbogaart |
| 3,055,362 | A | 9/1962 | Uytenbogaatt |
| 3,115,133 | A | 12/1963 | Morando |

(Continued)

FOREIGN PATENT DOCUMENTS

EP    1 712 178 A2    10/2006

(Continued)

OTHER PUBLICATIONS

International Search Report and Written Opinion for PCT/US07/84891, mailed Sep. 15, 2008, 7 pages.

(Continued)

*Primary Examiner*—Nicholas D Lucchesi
*Assistant Examiner*—Gerald Landry, II
(74) *Attorney, Agent, or Firm*—Cooley Godward Kronish LLP

(57) ABSTRACT

An apparatus includes a housing, a medicament container and an actuator. The actuator includes a release member and an energy storage member having a first position and a second position. In the first position, the energy storage member has a first potential energy. In the second position the energy storage member has a second potential energy. The energy storage member is configured to convert a portion of the first potential energy into kinetic energy when moved from the first position to the second position to move the medicament container within the housing. The energy storage member has a longitudinal axis offset from a longitudinal axis of the medicament container. The release member is configured to selectively deploy the energy storage member from its first position to its second position.

26 Claims, 46 Drawing Sheets

U.S. PATENT DOCUMENTS

| | | |
|---|---|---|
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,945,379 A | 3/1976 | Pritz et al. |
| 4,108,177 A | 8/1978 | Pistor |
| 4,226,235 A | 10/1980 | Sarnoff et al. |
| 4,360,019 A | 11/1982 | Portner et al. |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,853,521 A | 8/1989 | Claeys et al. |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,125,898 A | 6/1992 | Kaufhold, Jr. et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,412 A | 5/1994 | Rex |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,399,163 A | 3/1995 | Peterson et al. |
| 5,417,660 A | 5/1995 | Martin |
| 5,466,217 A | 11/1995 | Myers et al. |
| 5,514,135 A | 5/1996 | Earle |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A * | 4/1997 | Newman ................... 604/185 |
| 5,645,534 A | 7/1997 | Chanoch |
| 5,681,291 A | 10/1997 | Galli |
| 5,695,476 A | 12/1997 | Harris |
| 5,716,338 A | 2/1998 | Hjertman et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,814,020 A | 9/1998 | Gross |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,852,590 A | 12/1998 | de la Huerga |
| 5,853,292 A | 12/1998 | Eggert et al. |
| 5,868,713 A | 2/1999 | Klippenstein |
| 5,868,721 A | 2/1999 | Marinacci |
| D407,487 S | 3/1999 | Greubel et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,971,953 A | 10/1999 | Bachynsky |
| 6,015,438 A | 1/2000 | Shaw |
| 6,039,713 A | 3/2000 | Botich et al. |
| 6,045,534 A | 4/2000 | Jacobsen et al. |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,258,063 B1 | 7/2001 | Haar et al. |
| 6,259,654 B1 | 7/2001 | de la Huerga |
| 6,264,629 B1 | 7/2001 | Landau |
| 6,312,412 B1 | 11/2001 | Saied et al. |
| 6,317,630 B1 | 11/2001 | Gross et al. |
| 6,334,070 B1 | 12/2001 | Nova et al. |
| 6,364,866 B1 | 4/2002 | Furr et al. |
| 6,371,939 B2 | 4/2002 | Bergens et al. |
| 6,387,078 B1 | 5/2002 | Gillespie, III |
| 6,405,912 B2 | 6/2002 | Giannou |
| 6,406,455 B1 * | 6/2002 | Willis et al. ................... 604/68 |
| 6,411,567 B1 | 6/2002 | Niemiec et al. |
| 6,413,236 B1 | 7/2002 | Van Dyke |
| 6,425,897 B2 | 7/2002 | Overes et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,771 B1 | 11/2002 | Lavi et al. |
| 6,494,863 B1 | 12/2002 | Shaw et al. |
| 6,500,150 B1 * | 12/2002 | Gross et al. ................. 604/131 |
| 6,514,230 B1 | 2/2003 | Munk et al. |

| | | | | | | |
|---|---|---|---|---|---|---|
| 6,529,446 B1 | 3/2003 | de la Huerga | | 2001/0005781 A1 | 6/2001 | Bergens et al. |
| 6,530,900 B1 | 3/2003 | Daily et al. | | 2002/0074345 A1 | 6/2002 | Schneider et al. |
| 6,530,904 B1 | 3/2003 | Edwards et al. | | 2002/0076679 A1 | 6/2002 | Aman |
| 6,535,714 B2 | 3/2003 | Melker et al. | | 2003/0028145 A1 | 2/2003 | Duchon et al. |
| 6,540,675 B2 | 4/2003 | Aceti et al. | | 2003/0040717 A1 | 2/2003 | Saulenas et al. |
| 6,544,234 B1 | 4/2003 | Gabriel | | 2003/0100862 A1 | 5/2003 | Edwards et al. |
| 6,551,276 B1 | 4/2003 | Mann et al. | | 2003/0105430 A1 | 6/2003 | Lavi et al. |
| 6,551,298 B1 | 4/2003 | Zhang | | 2003/0106824 A1 | 6/2003 | Wilmot et al. |
| 6,554,798 B1 | 4/2003 | Mann et al. | | 2003/0135388 A1 | 7/2003 | Martucci et al. |
| 6,558,320 B1 | 5/2003 | Causey, III et al. | | 2003/0233070 A1 | 12/2003 | De La Serna et al. |
| 6,569,123 B2 | 5/2003 | Alchas | | 2004/0015125 A1 | 1/2004 | Alexandre et al. |
| 6,572,584 B1 | 6/2003 | Shaw et al. | | 2004/0019326 A1 | 1/2004 | Gilbert et al. |
| 6,574,166 B2 | 6/2003 | Niemiec | | 2004/0039336 A1 | 2/2004 | Amark et al. |
| 6,575,939 B1 | 6/2003 | Brunel | | 2004/0039337 A1 | 2/2004 | Letzing |
| RE38,189 E | 7/2003 | Walker et al. | | 2004/0039368 A1 | 2/2004 | Reilly et al. |
| 6,585,685 B2 | 7/2003 | Staylor et al. | | 2004/0054327 A1 | 3/2004 | Gillespie, III |
| 6,585,698 B1 | 7/2003 | Packman et al. | | 2004/0116854 A1 | 6/2004 | Abulhaj et al. |
| 6,589,158 B2 | 7/2003 | Winkler | | 2004/0138611 A1 | 7/2004 | Griffiths et al. |
| 6,595,956 B1 | 7/2003 | Gross et al. | | 2004/0143298 A1 | 7/2004 | Nova et al. |
| 6,599,272 B1 * | 7/2003 | Hjertman et al. ............ 604/209 | | 2004/0159364 A1 * | 8/2004 | Landau et al. ................. 141/2 |
| 6,633,796 B1 | 10/2003 | Pool et al. | | 2004/0220524 A1 | 11/2004 | Sadowski et al. |
| 6,641,566 B2 | 11/2003 | Douglas et al. | | 2004/0249358 A1 | 12/2004 | McWethy et al. |
| 6,645,181 B1 | 11/2003 | Lavi et al. | | 2004/0267204 A1 | 12/2004 | Brustowicz |
| 6,648,850 B2 | 11/2003 | Landau | | 2005/0033234 A1 | 2/2005 | Sadowski et al. |
| 6,676,630 B2 | 1/2004 | Landau et al. | | 2005/0033386 A1 | 2/2005 | Osborn et al. |
| 6,689,093 B2 | 2/2004 | Landau | | 2005/0062603 A1 | 3/2005 | Fuerst et al. |
| 6,702,778 B2 | 3/2004 | Hill et al. | | 2005/0090781 A1 | 4/2005 | Baba et al. |
| 6,707,763 B2 | 3/2004 | Osberg et al. | | 2005/0134433 A1 | 6/2005 | Sweeney, II |
| 6,708,050 B2 | 3/2004 | Carim | | 2005/0148931 A1 | 7/2005 | Juhasz |
| 6,722,916 B2 | 4/2004 | Buccinna et al. | | 2005/0148945 A1 | 7/2005 | Chen |
| 6,723,077 B2 | 4/2004 | Pickup et al. | | 2005/0159705 A1 | 7/2005 | Crawford et al. |
| 6,726,661 B2 | 4/2004 | Munk et al. | | 2005/0165360 A1 | 7/2005 | Stamp |
| 6,736,796 B2 | 5/2004 | Shekalim | | 2005/0171477 A1 | 8/2005 | Rubin et al. |
| 6,743,635 B2 | 6/2004 | Neel et al. | | 2005/0182358 A1 | 8/2005 | Veit et al. |
| 6,749,437 B2 | 6/2004 | Chan | | 2005/0197654 A1 | 9/2005 | Edman et al. |
| 6,752,781 B2 | 6/2004 | Landau et al. | | 2005/0267403 A1 | 12/2005 | Landau et al. |
| 6,767,336 B1 | 7/2004 | Kaplan | | 2005/0277891 A1 | 12/2005 | Sibbitt |
| 6,770,052 B2 | 8/2004 | Hill et al. | | 2006/0030819 A1 | 2/2006 | Young et al. |
| 6,783,509 B1 | 8/2004 | Landau et al. | | 2006/0053036 A1 | 3/2006 | Coffman et al. |
| 6,786,875 B2 | 9/2004 | Barker et al. | | 2006/0058848 A1 | 3/2006 | Piraino et al. |
| 6,793,646 B1 | 9/2004 | Giambattista et al. | | 2006/0111666 A1 | 5/2006 | Hommann et al. |
| 6,803,856 B1 | 10/2004 | Murphy et al. | | 2006/0111671 A1 | 5/2006 | Klippenstein |
| 6,808,514 B2 | 10/2004 | Schneider et al. | | 2006/0129090 A1 | 6/2006 | Moberg et al. |
| 6,809,653 B1 | 10/2004 | Mann et al. | | 2006/0189938 A1 | 8/2006 | Hommann et al. |
| 6,817,986 B2 | 11/2004 | Slate et al. | | 2006/0200077 A1 | 9/2006 | Righi et al. |
| 6,830,560 B1 | 12/2004 | Gross et al. | | 2006/0247579 A1 | 11/2006 | Friedman |
| 6,839,304 B2 | 1/2005 | Niemiec et al. | | 2006/0265186 A1 | 11/2006 | Holland et al. |
| 6,872,200 B2 | 3/2005 | Mann et al. | | 2007/0008113 A1 | 1/2007 | Spoonhower et al. |
| 6,875,195 B2 | 4/2005 | Choi | | 2007/0074722 A1 | 4/2007 | Giroux et al. |
| 6,883,222 B2 | 4/2005 | Landau | | 2007/0088268 A1 | 4/2007 | Edwards et al. |
| 6,923,764 B2 | 8/2005 | Aceti et al. | | 2007/0129708 A1 | 6/2007 | Edwards et al. |
| 6,936,029 B2 | 8/2005 | Mann et al. | | 2007/0184847 A1 | 8/2007 | Hansen et al. |
| 6,937,150 B2 | 8/2005 | Medema et al. | | 2007/0210147 A1 | 9/2007 | Morrone et al. |
| 6,942,646 B2 | 9/2005 | Langley et al. | | 2007/0213598 A1 | 9/2007 | Howard et al. |
| 6,946,299 B2 | 9/2005 | Neel et al. | | 2007/0239114 A1 | 10/2007 | Edwards et al. |
| 6,949,082 B2 | 9/2005 | Langley et al. | | 2008/0033393 A1 | 2/2008 | Edwards et al. |
| 6,952,604 B2 | 10/2005 | DeNuzzio et al. | | 2008/0058719 A1 | 3/2008 | Edwards et al. |
| 6,953,445 B2 | 10/2005 | Wilmot et al. | | 2008/0059133 A1 | 3/2008 | Edwards et al. |
| 6,953,693 B2 | 10/2005 | Neel et al. | | 2008/0103490 A1 | 5/2008 | Edwards et al. |
| 6,958,691 B1 | 10/2005 | Anderson et al. | | | | |
| 6,959,247 B2 | 10/2005 | Neel et al. | | FOREIGN PATENT DOCUMENTS | | |
| 6,961,285 B2 | 11/2005 | Niemiec et al. | | | | |
| 6,964,650 B2 | 11/2005 | Alexandre et al. | | FR | 2 509 615 | 1/1983 |
| 6,969,259 B2 | 11/2005 | Pastrick et al. | | MX | PA04009276 | 1/2005 |
| 6,979,316 B1 * | 12/2005 | Rubin et al. ................. 604/156 | | WO | WO 91/04760 A1 | 4/1991 |
| 6,979,326 B2 | 12/2005 | Mann et al. | | WO | WO 95/26009 | 9/1995 |
| 6,985,870 B2 | 1/2006 | Martucci et al. | | WO | WO 95/35126 | 12/1995 |
| 6,997,911 B2 | 2/2006 | Klitmose | | WO | WO 01/24690 A2 | 4/2001 |
| 7,014,470 B2 | 3/2006 | Vann | | WO | WO 01/26020 A1 | 4/2001 |
| 7,113,101 B2 | 9/2006 | Peterson et al. | | WO | WO 01/88828 | 11/2001 |
| 7,116,233 B2 | 10/2006 | Zhurin | | WO | WO 03/095001 A1 | 11/2003 |
| 7,126,879 B2 | 10/2006 | Snyder | | WO | WO 03/097133 A1 | 11/2003 |
| 7,158,011 B2 | 1/2007 | Brue | | WO | WO 2004/054644 | 7/2004 |

| | | | |
|---|---|---|---|
| WO | WO 2005/050526 A2 | 6/2005 | |
| WO | WO 2005/077441 A2 | 8/2005 | |
| WO | WO 2006/109778 A1 | 10/2006 | |
| WO | WO 2008/082704 A2 | 7/2008 | |

OTHER PUBLICATIONS

"Solutions for Medical Devices," 3M Brochure.
Merle Tingelstad, "Revolutionary Medical Technology Increases Demand for Flexible Interconnects."
"Flexible circuits / Flex circuits / Flexible Technology Ltd.," Flexible Technology Limited.
"Flexible circuits capabilities of Flexible Technology Limited," Our Flexible Circuits Capabilities.
"Flex Circuits/flexible circuits design guide."
"Insect Stings Auto-injector Pouches and Carry Cases," The Insect Stings On-Line Shop.
"Anaphylaxis Canada Product Catalogue," Anaphylaxis Canada > Living with Anaphylaxis > Tools and Resources.
"Microfuidics Device Provides Programmed, Long-Term Drug Dosing," nano techwire.com.
Roger Allan, "Medical Electronics: Technology Advances Will Revolutionize Healthcare," Sep. 30, 2002.
RFID Gazette, "Smart Labels in Healthcare," Sep. 29, 2005.
"Merck Serono Launches easypod(R), First Electronic Growth Hormone Injection Device," Jan. 30, 2007.
Dr. Oliver Scholz, "Drug depot in a tooth."
Heartsine Technology, samaritan™ PAD Accessories [online] [retrieved on Jun. 1, 2007] Retrieved from the Internet <URL: http://www.heartsinecom/aboutsam-accessories.htm>.
ClineSense Corporation, "Drug delivery devices A potentially harsh environment for drugs," Stability [online] [retrieved on Jun. 1, 2007] Retrieved from the Internet <URL: http://www.clinisense.com/devices.htm>.
CliniSense Corporation, "LifeTrack Technology A new method to detect improper storage." Stability [online] [retrieved on Jun. 1, 2007] Retrieved from the Internet <URL: http://www.clinisense.com/tech.htm>.
AED Professionals™ Brochure [online] [retrieved on Jun. 1, 2007] Retrieved from the Internet <URL: http://www.aedprofessionals.com/>.
Daniel Ruppar, "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8>.
International Search Report and Written Opinion for International Patent Application No. PCT/US07/007626 mailed Sep. 29, 2008.
Examination Report for GB 0708523.6, mailed Dec. 8, 2008.
Combined Search and Examination Report for GB 0822532.8, mailed Jan. 21, 2009.
Examination Report for GB 0822532.8, mailed May 21, 2009.

* cited by examiner

DEVICES, SYSTEMS, AND METHODS FOR MEDICAMENT DELIVERY

CROSS-REFERENCE TO RELATED APPLICATIONS

This application is a continuation-in-part of U.S. patent application Ser. No. 10/515,571 entitled "Devices, Systems and Methods for Medicament Delivery," filed Nov. 23, 2004, now U.S. Pat. No. 7,416,540, which is a national stage filing under 35 U.S.C. § 371 of International Patent Application No. PCT/US2004/039386, entitled "Devices, Systems and Methods for Medicament Delivery," filed Nov. 23, 2004, each of which is incorporated herein by reference in its entirety. This application is a continuation-in-part of U.S. patent application Ser. No. 10/572,148, entitled "Devices, Systems and Methods for Medicament Delivery," filed Mar. 16, 2006, which is a national stage filing under 35 U.S.C. § 371 of International Patent Application No. PCT/US2006/003415, entitled "Devices, Systems and Methods for Medicament Delivery," filed Feb. 1, 2006, which claims priority to U.S. Provisional Application Ser. No. 60/648,822, entitled "Devices, Systems and Methods for Medicament Delivery," filed Feb. 1, 2005 and U.S. Provisional Application Ser. No. 60/731,886, entitled "Auto-Injector with Feedback," filed Oct. 31, 2005, each of which is incorporated herein by reference in its entirety

BACKGROUND

The invention relates generally to a medical device, and more particularly to an auto-injector for injecting a medicament into a body of a patient.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure.

Because emergency medical facilities may not available when an individual is suffering from an allergic reaction, some individuals carry an auto-injector to rapidly self-administer a medicament in response to an allergic reaction. Some known auto-injectors are cylindrical in shape and include a spring loaded needle to automatically penetrate the user's skin and inject the medicament. Such known auto-injectors can be bulky and conspicuous, which can make carrying them inconvenient and undesirable. Moreover, some known auto-injectors do not have a retractable needle and, as such, cause a sharps hazard when injection is complete.

Some known auto-injectors include a locking cap at the proximal end of the auto-injector to prevent inadvertent actuation and a needle cover at the distal end of the auto-injector. Such a configuration can, at times, cause a user to become confused as to which end of the auto-injector is the "needle end" (i.e., the distal end) and which end of the auto-injector is the "actuation end" (i.e., the proximal end). As such, in some situations, a user may mistakenly actuate the known auto-injector away from the intended injection site. Such an error can result, for example, in the auto-injector being actuated into the user's thumb and/or finger.

Thus, a need exists for an auto-injector that can be more conveniently carried by a user and does not present a sharps hazard upon completion of the injection. Furthermore, a need exists for an auto-injector that can be actuated from its distal end.

SUMMARY

Apparatuses and methods for automatic medicament injection are described herein. In one embodiment, an apparatus includes a housing, a medicament container disposed within the housing and an actuator. The actuator is configured to be disposed within the housing and to move the medicament container within the housing. The actuator includes a release member and an energy storage member. The energy storage member has a first position and a second position. When in the first position, the energy storage member has a first potential energy. When in the second position the energy storage member has a second potential energy less than the first potential energy. The energy storage member is configured to convert a portion of the first potential energy into kinetic energy when it moves from its first position to its second position to move the medicament container within the housing. The energy storage member has a longitudinal axis offset from a longitudinal axis of the medicament container. The release member is configured to selectively deploy the energy storage member from its first position to its second position.

DETAILED DESCRIPTION

Figure 1:
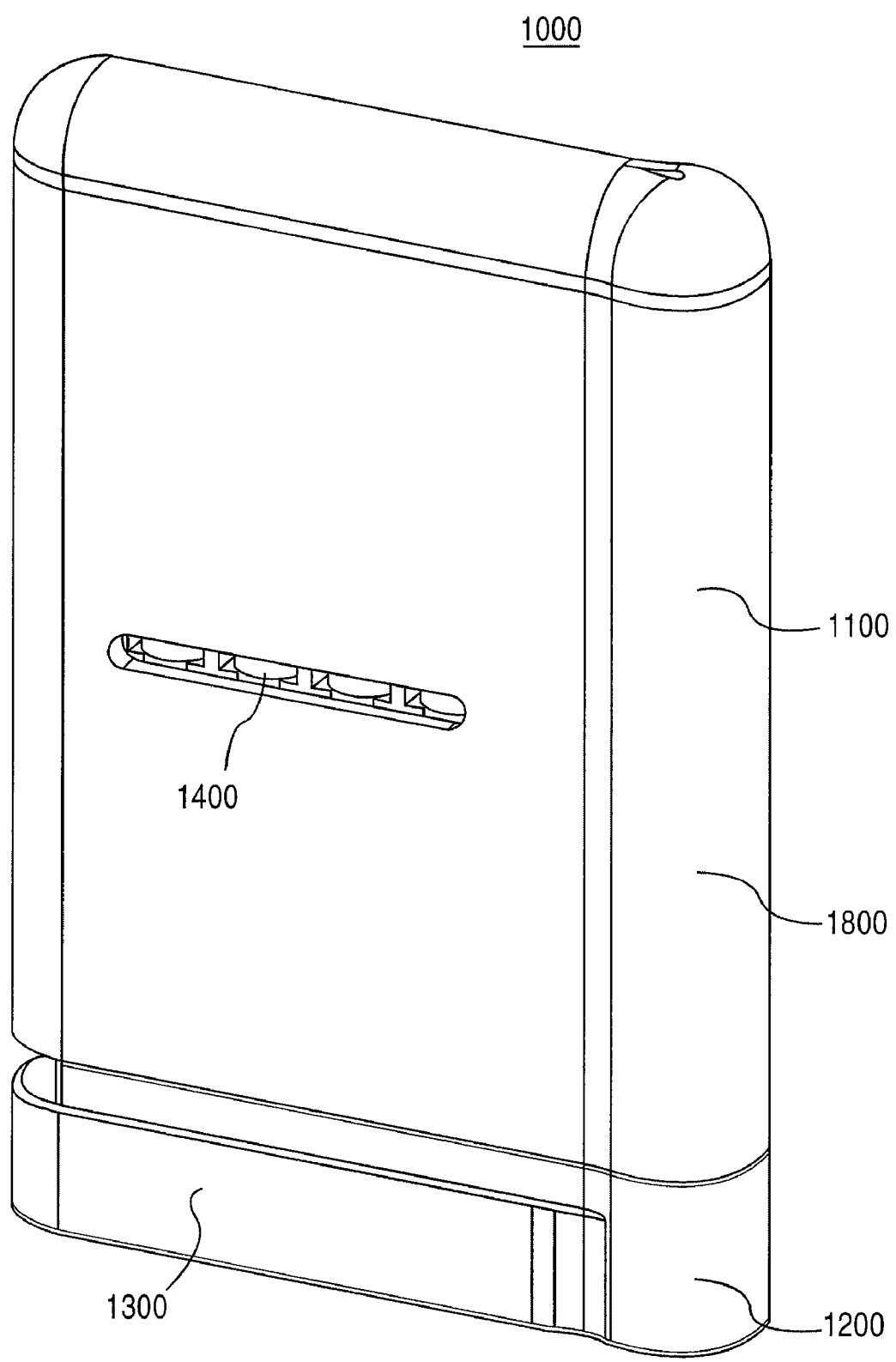
FIG. 1 is a perspective view of a system according to an embodiment of the invention.

Apparatuses and methods for automatic medicament injection are described herein. In some embodiments, an apparatus includes a housing, a medicament container disposed within the housing and an actuator. The actuator is configured to be disposed within the housing and to move the medicament container within the housing. The actuator includes a release member and an energy storage member. The energy storage member, which can be, for example, a compressed gas container, has a first position and a second position. When in the first position, the energy storage member has a first potential energy. When in the second position the energy storage member has a second potential energy less than the first potential energy. The energy storage member is configured to convert a portion of the first potential energy into kinetic energy when moved from its first position to its second position to move the medicament container within the housing. The energy storage member has a longitudinal axis offset from a longitudinal axis of the medicament container. The release member is configured to selectively deploy the energy storage member from its first position to its second position.

In some embodiments, an apparatus includes a housing, a needle and an actuator. The needle has a first end and a second end and defines a longitudinal axis. The actuator is configured to be disposed within the housing and to move the needle between a first needle position and a second needle position. When in the first needle position, the second end of the needle is within the housing. When in the second needle position, the second end of the needle is outside the housing. The actuator includes a release member and an energy storage member. The energy storage member has a first position and a second position. When in the first position, the energy storage member has a first potential energy. When in the second position the energy storage member has a second potential energy less than the first potential energy. The energy storage member is configured to convert a portion of the first potential energy into kinetic energy when moved from its first position to its second position to move the needle between the first needle position and the second needle position. The energy storage member has a longitudinal axis offset from the longitudinal axis of the needle. The release member is configured to selectively deploy the energy storage member from its first position to its second position.

In some embodiments, an apparatus includes a housing, a needle, a medicament container and an actuator. The needle has a first end and a second end and defines a longitudinal axis. The actuator is configured to be disposed within the housing and to move the needle between a first needle position and a second needle position. When in the first needle position, the second end of the needle is within the housing. When in the second needle position, the second end of the needle is outside the housing. The actuator is further configured to move the medicament container between a first medicament container position and a second medicament container position. When in the first medicament container position, a lumen defined by the needle is fluidically isolated from the medicament container. When in the second medicament container position, the first end of the needle is disposed within the medicament container such that the lumen is in fluid communication with the medicament container. The actuator includes a release member and an energy storage member. The energy storage member has a first position and a second position. When in the first position, the energy storage member has a first potential energy. When in the second position the energy storage member has a second potential energy less than the first potential energy. The energy storage member is configured to convert a portion of the first potential energy into kinetic energy when moved from its first position to its second position to move the needle between the first needle position and the second needle position. The energy storage member has a longitudinal axis offset from the longitudinal axis of the needle. The release member is configured to selectively deploy the energy storage member from the first position to the second position.

In some embodiments, an apparatus includes an actuator disposable within a housing of an auto-injector. The actuator is configured to move a medicament container relative to the housing, and includes a gas container, a biasing member and a puncturer. The gas container, which is configured to store a compressed gas, is movable between a first position and a second position. The biasing member has a retracted configuration and an expanded configuration. The biasing member is configured to engage the gas container such that when the biasing member moves from the retracted configuration to the expanded configuration the gas container is moved from the first position to the second position. The puncturer is configured to penetrate a portion of the gas container when the gas container moves to the second position to allow a portion of the compressed gas to be released from the gas container into a gas chamber defined within the housing adjacent the medicament container.

In some embodiments, an apparatus includes a housing having a distal end portion and a proximal end portion, a medicament injector, an energy storage member and a retainer. The medicament injector is disposed within the housing and includes a medicament container and a needle. The energy storage member, which can be, for example, a gas container configured to contain a pressurized gas, is configured to produce a force when moved from a first configuration to a second configuration to move the medicament injector between a first position and a second position. The retainer has a first position and a second position. When the retainer is in its first position, the retainer is configured to retain the energy storage member in its first configuration. When the retainer is in its second position, the retainer is configured to allow the energy storage member to be moved from its first configuration to its second configuration. The retainer is configured to be selectively moved from its first position to its second position by manipulating an actuator adjacent the distal end portion of the housing.

Figure 2:
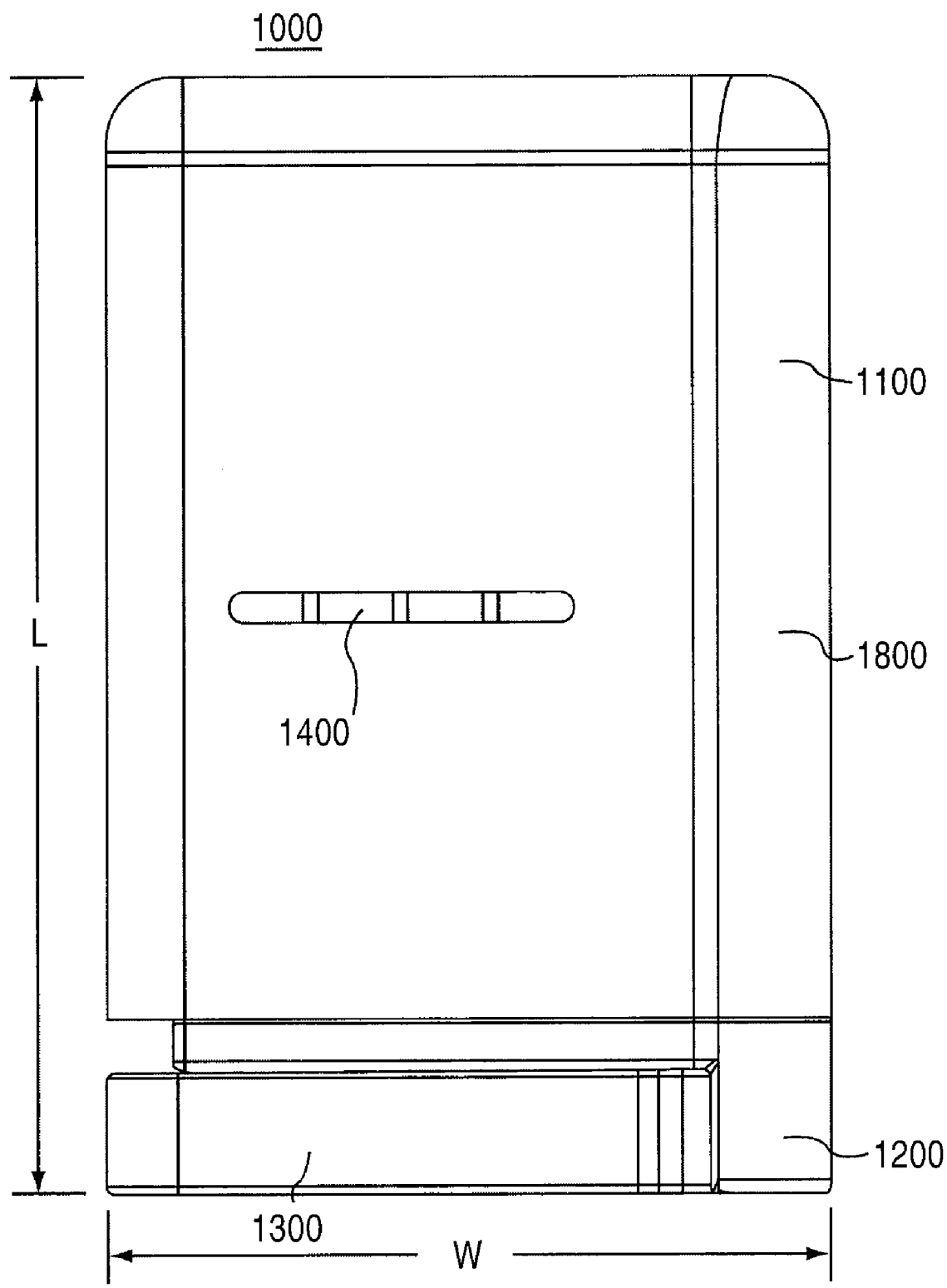
FIG. 2 is a front view of a system according to an embodiment of the invention.
Figure 3:
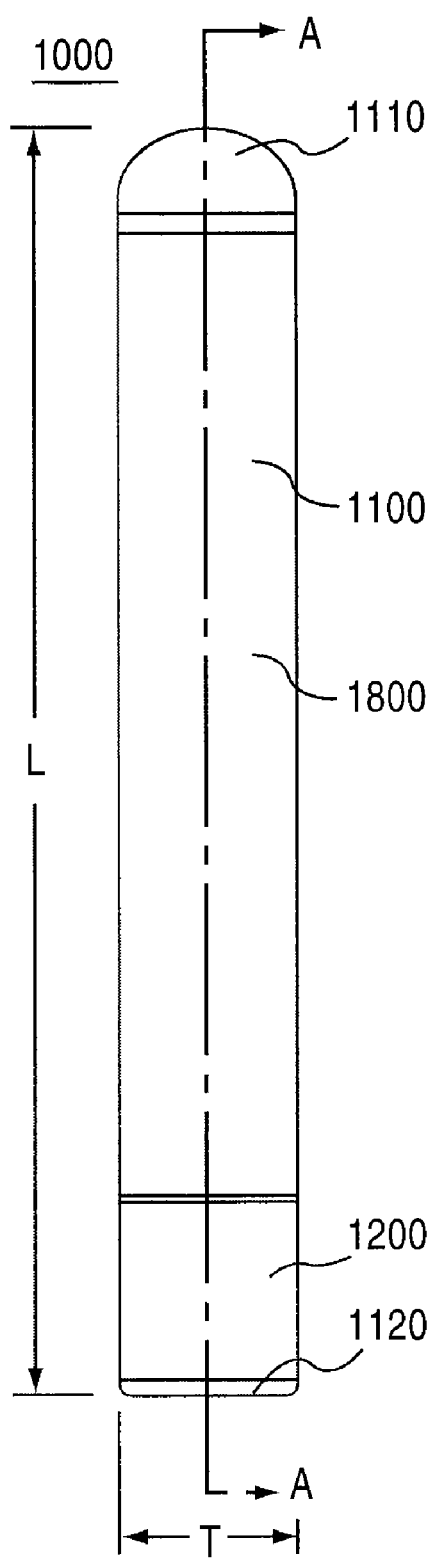
FIG. 3 is a side view of a system according to an embodiment of the invention.

FIG. 1 is a perspective view, FIG. 2 is a front view, and FIG. 3 is a side view, of a system 1000 according to the invention, which can comprise a housing 1100, which, in some embodiments, can comprise a handheld portion 1800 separated via an actuation guard 1200 from an actuation bar 1300. Actuation guard 1200 can prevent accidental activation of system 1000. Housing 1100 can be constructed of a durable material, such as stainless steel, aluminum, polycarbonate, etc., to protect a compressed gas container, medicament, injection apparatus and/or user of system 1000. The injection apparatus can be actuated by a fluid pressure, such as pressure provided by the compressed gas, which upon completion of actuation can escape housing 1100 via gas escape opening, such as via status indicator 1400.

A status of a system 1000 can be determined via status indicator 1400, which can provide a view, such as via a UV blocking, photo-sensitive, and/or translucent window, into an interior of housing 1100. Viewable through the window can be a status of medicament carried by housing 1100, a location of a needle and/or injection apparatus for the medicament, and/or an activation status of system 1000. For example, if the medicament has aged to the point of discoloration, which aging might or might not render the medication useless, harmful, etc., status indicator 1400 can allow that situation to be determined. In some embodiments, gas can escape housing 1100 via status indicator 1400 and/or another opening in housing 1100.

Some embodiments of system 1000 can provide a compact medicament delivery mechanism that can efficiently and/or rapidly deliver a prescribed dose. The length (L) and width (W) of system 1000 can be similar to that of a credit card, and the thickness (T) can be less than one inch. Thus, some embodiments of system 1000 can provide a conveniently carried, easy-to-use, easy to activate drug delivery apparatus that can require little to no training to safely carry, use, and/or dispose of.

To assist a user in positioning system 1000 in a correct orientation for injection, system 1000 and/or housing 1100 can provide various tactile clues. For example, a top 1110 of housing 1100 can be rounded, and a bottom 1120 of actuation bar 1300 of housing 1100 can be flat. Other tactile clues are also possible, such as bulges, ribs, grooves, gaps, roughened surfaces, indentations, etc.

Figure 4:
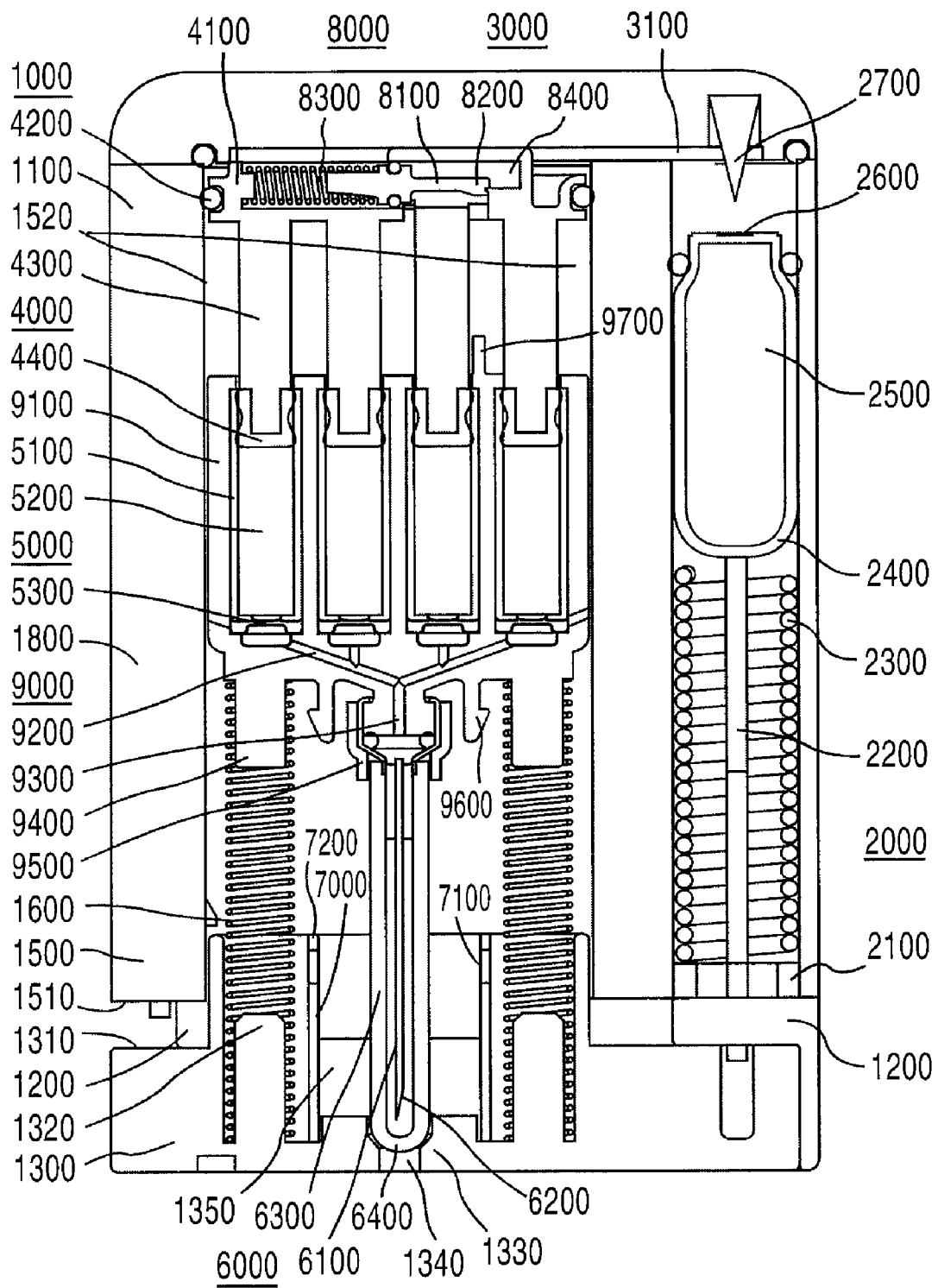
FIG. 4 is a cross-sectional view taken along line A-A of FIG. 3 of a system according to an embodiment of the invention in a first operative position.

FIG. 4 is a cross-sectional view taken along line A-A of FIG. 3 of an embodiment of a system 1000 in a first operative position. FIGS. 5, 6, 7, 8, and 9 show system 1000 of FIG. 4 in second, third, fourth, fifth, and sixth operative positions, respectively.

System 1000 can comprise a housing 1100, handheld portion 1800, actuation guard 1200, and/or actuation bar 1300. System 1000 can comprise system actuator 2000, gas reservoirs 3000, medicament actuator 4000, medicament storage assembly 5000, medicament carrier 9000, needle assembly 6000, use indicator 7000, and/or gas vent mechanism 8000, etc.

Upon removal, release, rotation, and/or relocation of actuation guard 1200, system actuator 2000 can be adapted to rapidly discharge an actuating portion of a contents of a compress gas container. For example, system actuator 2000 can comprise a compressed gas container 2400, which initially can contain a compressed gas 2500, an actuating portion of which can be released from container 2400 by penetration of a gas port 2600 via a point of a puncturer 2700. Upon removal and/or relocation of actuation guard 1200, actuation bar 1300 can be moved closer to and/or in contact with handheld portion 1800. Upon removal and/or relocation of actuation guard 1200, gas container 2400 can be brought into contact with puncturer 2700 via extension of a pre-compressed spring 2300 and/or movement of an actuation stick 2200. Thus, actuation guard 1200 can prevent accidental activation of system 1000 and/or unintended discharge of an actuating portion of the contents 2500 of gas container 2400.

Once gas port 2600 has been punctured, an actuating portion of compressed gas 2500 can escape from container 2400 and flow via gas reservoirs 3000, such as gas channel 3100. The flowing gas can meet and/or apply gas pressure to medicament actuator 4000, which can comprise a pusher 4100, which can travel within a sleeve 1500 defined by walls 1520. Sleeve 1500 can be constructed of metal, stainless steel, aluminum, plastic, polycarbonate, etc. Seals 4200, such as o-rings, can resist gas leakage, such as past pusher 4100 and/or out of housing 1100. Thus, pusher 4100 can function as a piston traveling within a cylinder, although it is not necessarily required that the cross-sectional shape of sleeve 1500 be round.

Medicament actuator 4000 can interface with medicament storage assembly 5000. For example, medicament actuator 4000 can comprise a plurality of plungers 4300, each of which can be capped with a piston 4400 which can sealingly slide and/or move within a corresponding vial 5100 containing a liquid medicament 5200. For example, in response to pressure applied by an actuating portion of the contents 2500 of compressed gas container 2400, pusher 4100 can cause plungers 4300 and/or pistons 4400 to simultaneously move. The number of corresponding sets of plungers 4300, pistons 4400, and/or vials 5100 can be 2, 3, 4, 5, 6, or more. Pistons 4400 can be constructed of a resilient, durable, and/or sealing material, such as a rubber. Each plunger 4300 from the plurality of plungers can define a longitudinal axis, the longitudinal axes (e.g., axes 4310, 4320, 4330, 4340) of the plurality of plungers can be parallel, non-coaxial, and/or co-planar.

Each vial 5100 from the plurality of vials can be substantially cylindrical with a substantially round and/or substantially elliptical cross-sectional shape. Thus, each vial 5100 can define a longitudinal axis, the longitudinal axes of the plurality of vials can be parallel, non-coaxial, and/or co-planar. The longitudinal axis of each vial can be co-axial with the longitudinal axis of its corresponding plunger.

Each vial can be capped at one end with a frangible seal 5300, which can be burst when piston 4400 generates sufficient pressure upon medicament 5200, thereby allowing at least a portion of medicament 5200 to flow out of vial 5100 and into medicament carrier 9000. Thus, the plurality of vials can be fluidly coupleable to the actuating portion of the contents 2500 of gas container 2400.

Medicament carrier 9000 can hold each of vials 5100 and can travel within sleeve 1500. Medicament carrier 9000 can comprise a plurality of channels 9200 adapted to receive medicament 5200 as it exits its respective vial 5100, and direct medicament 5200 to a common conduit 9300. Medicament carrier 9000 can interface with needle assembly 6000 and/or use indicator 7000.

From common conduit 9300, medicament 5200 can enter needle assembly 6000, such as into a single needle 6100 via which medicament can approach needle tip 6200. As medicament actuator 4000 and/or medicament carrier 9000 are driven toward actuator bar 1300, needle tip 6200 can penetrate an end 6400 of needle sheath 6300 and exit actuator bar 1300 at needle port 1340.

Figure 5:
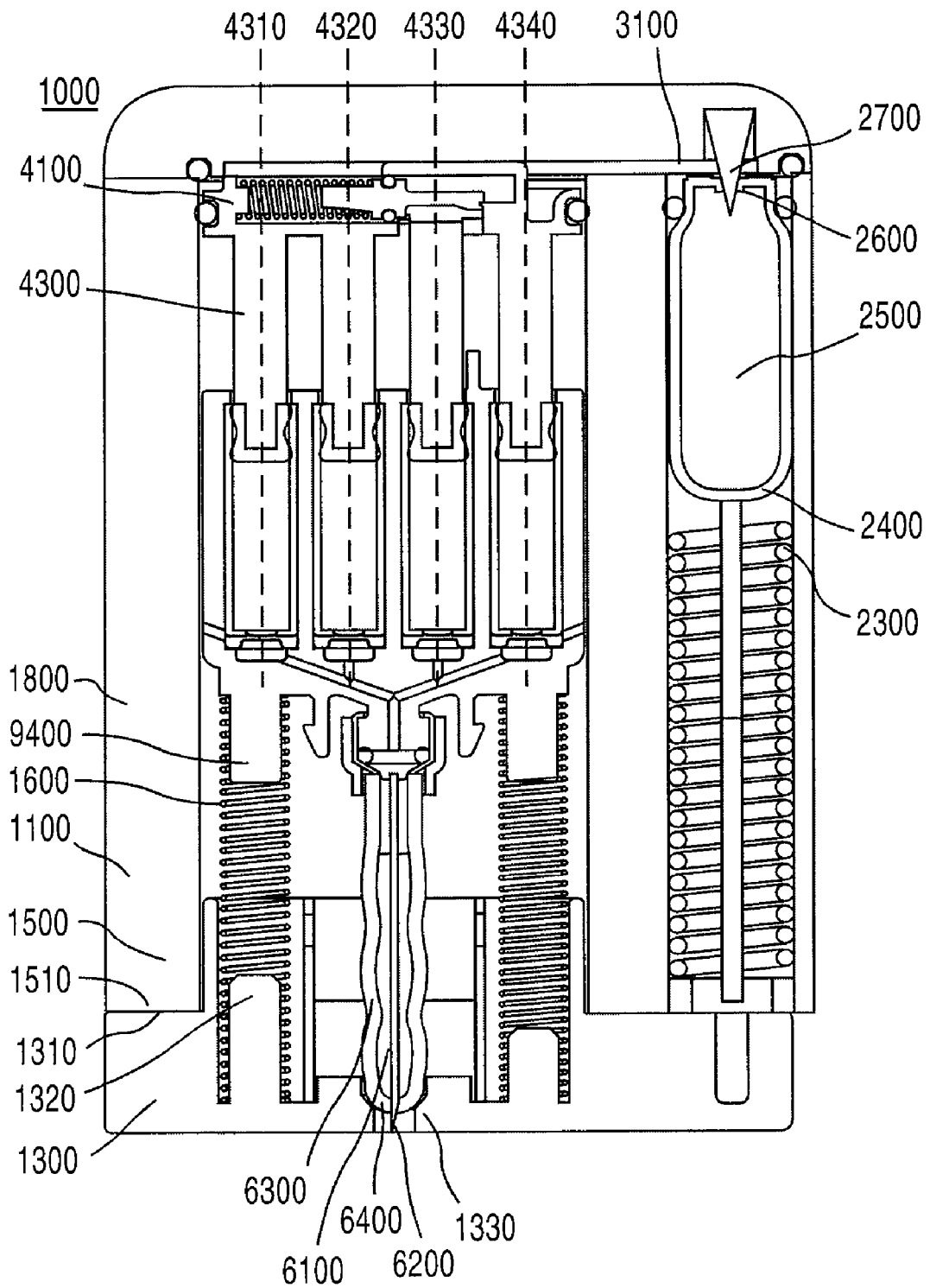
FIG. 5 is a cross-sectional view taken along line A-A of FIG. 3 of a system according to an embodiment of the invention in a second operative position.

Referring to FIG. 5, upon movement of actuation bar 1300 closer to handheld portion 1800, sheath seat 1330 can come in contact with sheath tip 6400, thereby causing sheath 6300 to buckle and/or crumble. As actuator bar 1300 comes in contact with handheld portion 1800, bar stop 1320 can approach medicament carrier stop 9400, while carrier spring 1600 is compressed.

Figure 6:
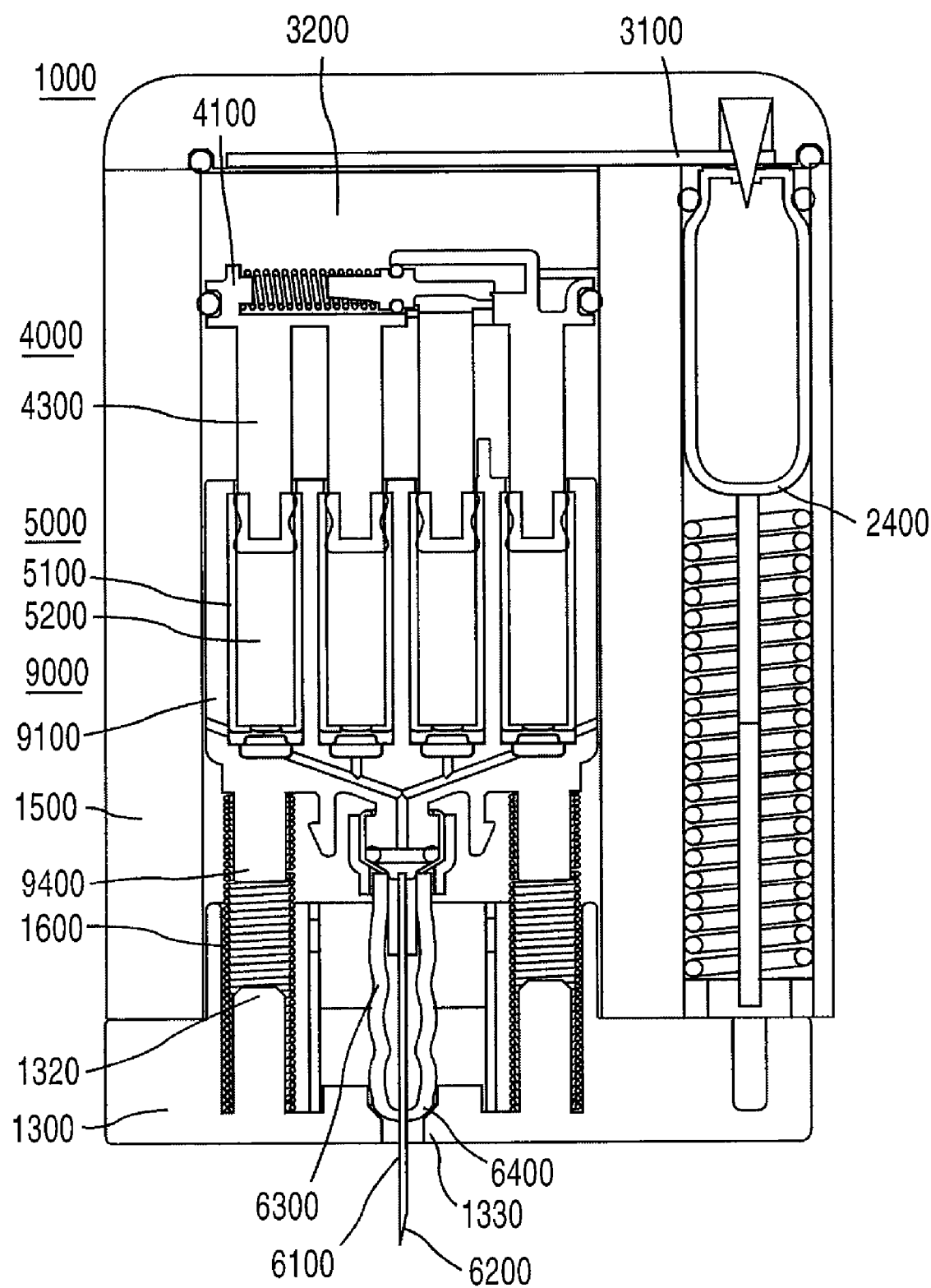
FIG. 6 is a cross-sectional view taken along line A-A of FIG. 3 of a system according to an embodiment of the invention in a third operative position.

Referring to FIG. 6, as at least a portion of contents 2500 of gas container 2400 escapes, it can flow through channel 3100. The gas, which can still be relatively pressurized, can begin to accumulate behind pusher 4100 to form an expanding gas chamber 3200 and to cause medicament actuator 4000, medicament storage assembly 5000, and medicament carrier 9000 to slide together within sleeve 1500. As medicament actuator 4000, medicament storage assembly 5000, and medicament carrier 9000 slide closer to actuator bar 1300, spring 1600 becomes increasingly compressed between bar stop 1320 and medicament carrier stop 9400. As medicament actuator 4000, medicament storage assembly 5000, and medicament carrier 9000 slide closer to actuator bar 1300, needle tip 6200 can extend further from actuator bar 1300 and sheath 6300 can become further compressed and/or deformed. At its ultimate extension point, needle tip 6200 can extend from housing 1100 from approximately 0.25 millimeters to approximately 20 millimeters, including all values and subranges therebetween, such as up to approximately 2 millimeters, greater than approximately 5 millimeters, from approximately 5.13 millimeters to approximately 9.98 millimeters, etc.

Figure 7:
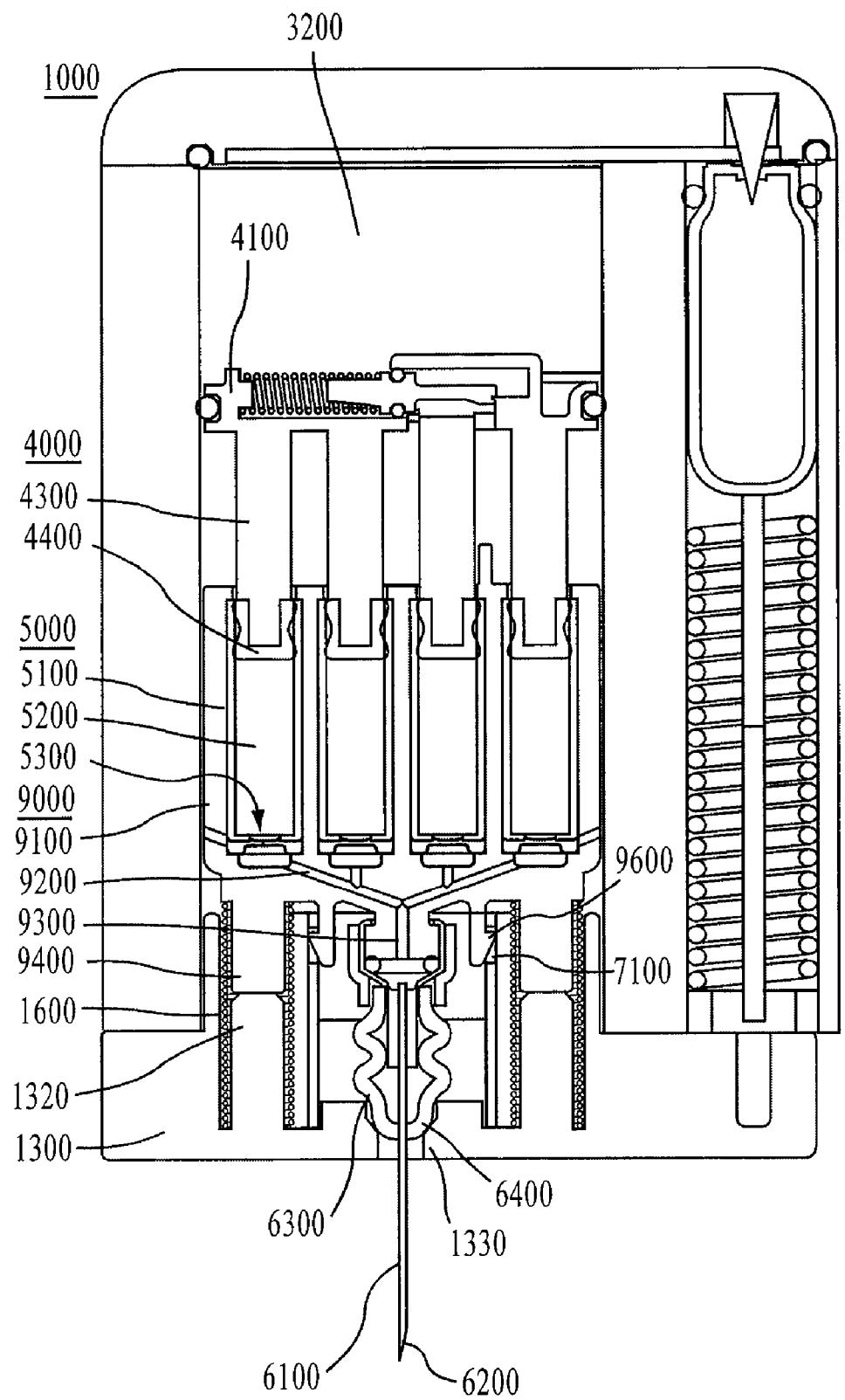
FIG. 7 is a cross-sectional view taken along line A-A of FIG. 3 of a system according to an embodiment of the invention in a fourth operative position.

Referring to FIG. 7, as gas chamber 3200 continues to expand, medicament carrier 9000 can be driven until medicament carrier stop 9400 contacts actuator bar stop 1300 thereby resisting further travel of medicament carrier 9000. At that point, additional expansion of gas chamber 3200 can cause medicament actuator 4000, pusher 4100, plungers 4300, and/or pistons 4400 to initiate travel with respect to medicament storage assembly 5000, thereby generating an expulsion pressure in vials 5100, and/or thereby rupturing frangible seals 5300 and allowing medicament 5200 to enter medicament carrier 9000, and begin flowing through medicament channels 9200, medicament conduit 9300, needle 6100, and/or out needle tip 6200 and into a patient. Alternatively, frangible seals 5300 can be replaced and/or augmented by a frangible seal located at or near where medicament conduit 9300 couples to needle 6100. Frangible seals 5300 can be constructed of a thin, taught, resilient, durable, and/or sealing material potentially having a predetermined yield strength, such as a rubber, such as chromo butyl rubber, and/or of a relatively brittle material potentially having a predetermined yield strength, such as ceramic, certain plastics, such as polystyrene, etc.

As medicament carrier stop 9400 contacts actuator bar stop 1320, medicament carrier hooks 9600 can engage with engagement receivers 7100 in use indicator 7000.

Figure 8:
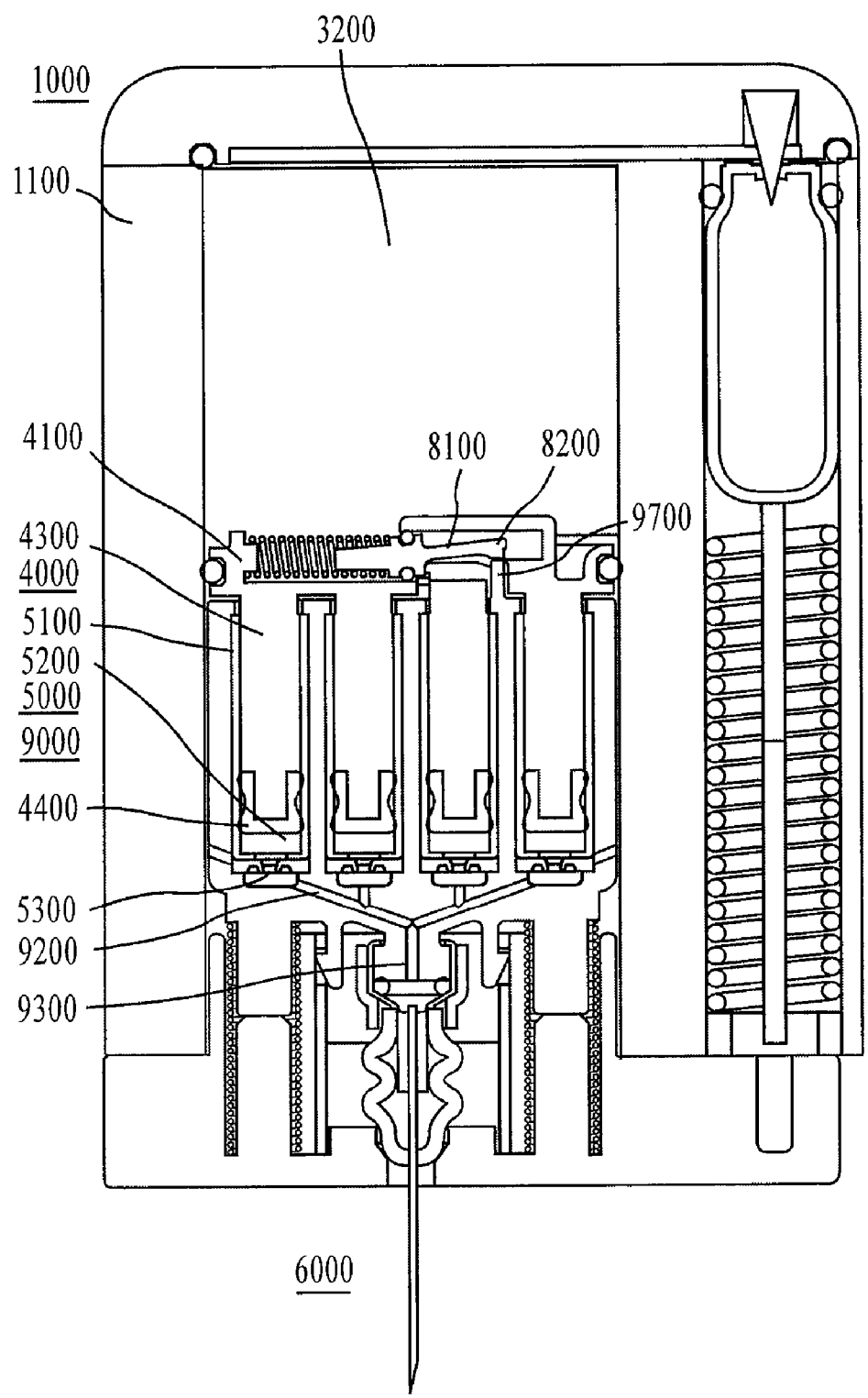
FIG. 8 is a cross-sectional view taken along line A-A of FIG. 3 of a system according to an embodiment of the invention in a fifth operative position.

Referring to FIG. 8, as gas chamber 3200 continues to expand, medicament actuator 4000, pusher 4100, plungers 4300, and/or pistons 4400 can continue moving until they complete their travel within medicament storage assembly 5000, thereby expelling a predetermined dose of medicament 5200 from vials 5100, out of needle assembly 6000, external to housing 1100, and/or into the patient. As gas chamber 3200 reaches its maximum size, medicament actuator 4000, pusher 4100, plungers 4300, and/or pistons 4400 can continue moving until they complete their travel with respect to medicament carrier 9000, thereby causing gas release actuator 9700 to engage with gas relief valve 8200. Engagement of gas release actuator 9700 with gas relief valve 8200 can cause gas within gas chamber 3200 to exit gas chamber 3200, discharge away from pistons 4400, and/or exhaust from system 1000 and/or housing 1100, such as via status indicator 1400 and/or a gas escape port located on housing 1100).

Figure 9:
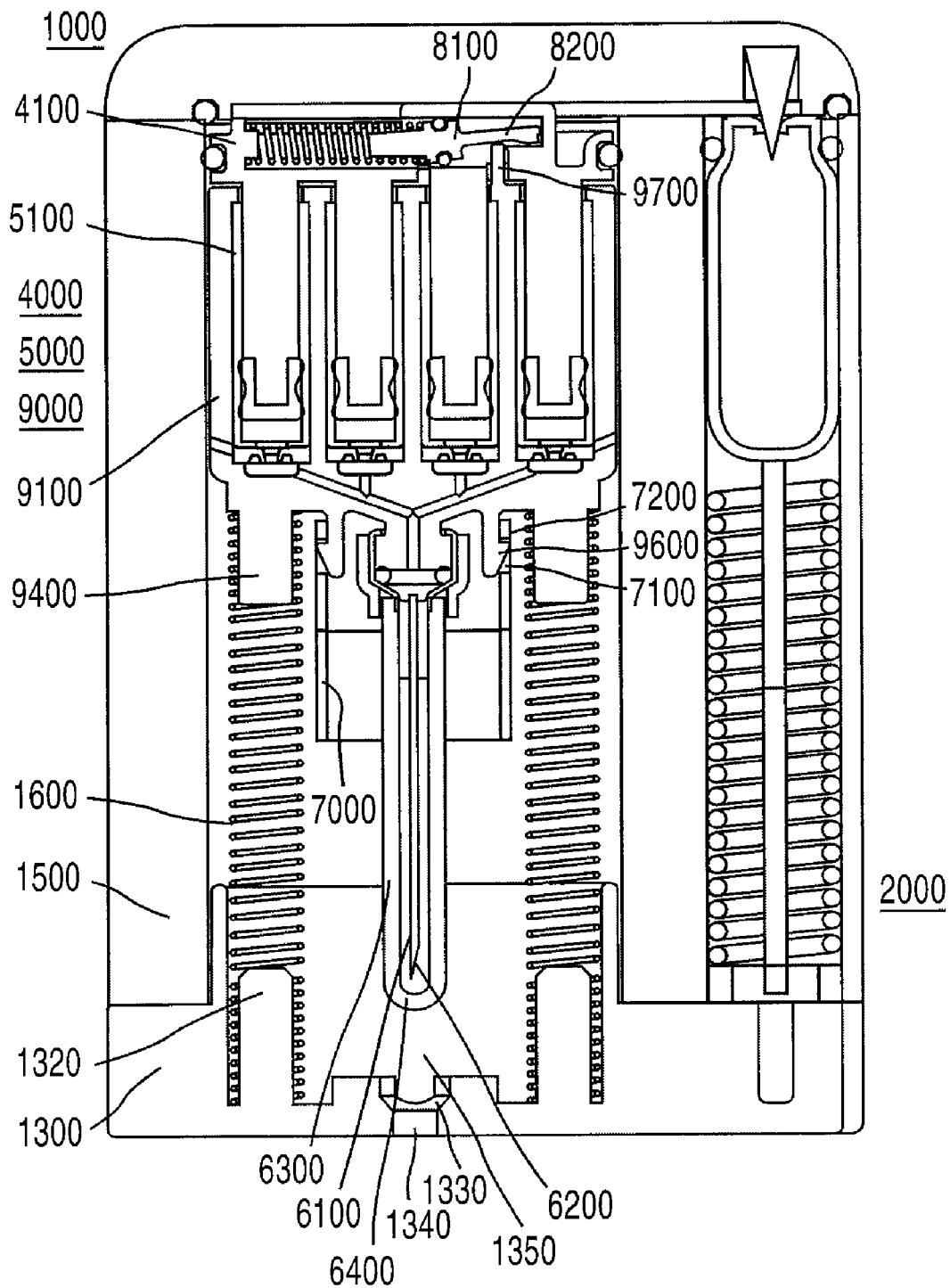
FIG. 9 is a cross-sectional view taken along line A-A of FIG. 3 of a system according to an embodiment of the invention in a sixth operative position.

Referring to FIG. 8 and FIG. 9, as sufficient gas is vented from gas chamber 3200, the pressure applied by the gas in gas chamber 3200 can decrease until the force applied by the gas on medicament actuator 4000 is less than the force of compressed spring 1600. Thus, spring(s) 1600 can begin to expand, thereby moving medicament carrier 9000, vial assembly 5000, and medicament actuator 4000 away from actuator bar 1300 and helping to exhaust gas from gas chamber 3200. As medicament carrier 9000 moves, use indicator 7000 can travel with it, due to the engaged relationship of medicament carrier hooks 9600 and engagement receivers 7100 and/or engagement catches 7200 in use indicator 7000. As use indicator 7000 moves away from actuation bar 1300, sheath 6300 can travel with it, thereby creating a gap between sheath tip 6400 and needle port 1340, and thereby exposing a previously non-visible colored portion 1350 of actuation bar 1300 and/or providing an indication that system 1000 has been used (and likely substantially exhausted of its medicament), thereby discouraging any further attempts to use system 1000.

As medicament carrier 9000 moves away from actuator bar 1300, needle 6100 can retract into sheath 6300 which unbuckles and/or un-deforms towards its original shape. Eventually, needle 6100 can retract completely within the boundaries of housing 1100, thereby tending to prevent accidental needle sticks after the initial injection and/or potentially reducing and/or eliminating a sharps hazard.

In some embodiments, system actuator 2000 can comprise a finger triggered, twistable, pivotable, and/or lever-operated mechanism. For example, system actuator 2000 can comprise a twistable handle that can screw into gas port 2600. In some embodiments, system actuator 2000 can be a finger trigger located on a side of the housing.

Figure 10:
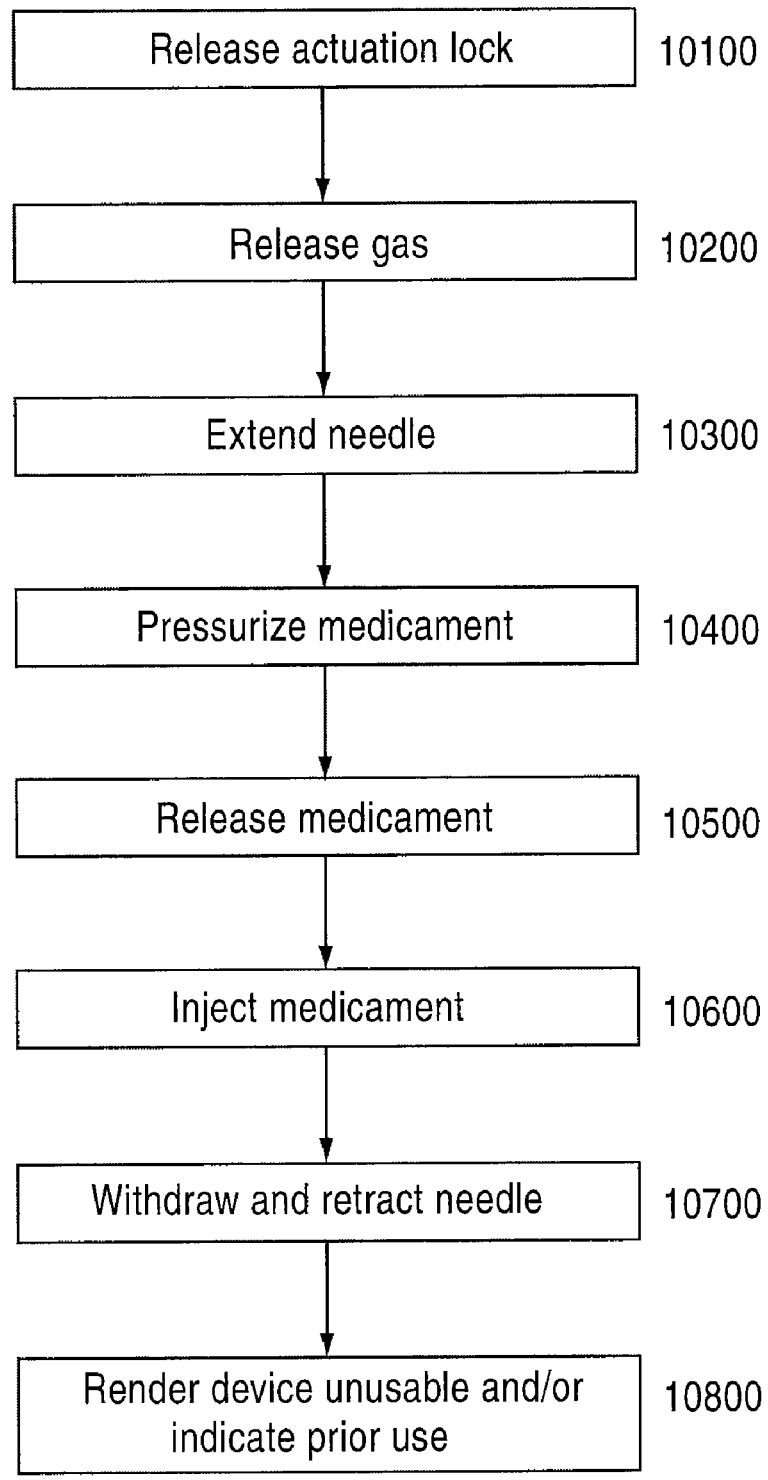
FIG. 10 is a flowchart illustrating a method according to an embodiment of the invention.

FIG. 10 is a flowchart of an embodiment of a method 10000 for operating a medicament delivery apparatus. At activity 10100, an actuation lock for the apparatus is released. At activity 10200, an actuating portion of the contents of a compressed gas container are released. At activity 10300, via pressure provided by the released gas, a needle is extended from the apparatus. At activity 10400, via pressure provided by the released gas, a piston applies pressure to a medicament stored in one of a plurality of vials. At activity 10500, a frangible seal containing the medicament in the vial is burst. At activity 10600, the medicament flows from the vial, through the needle, and into a patient. At activity 10700, once a predetermined dose is expelled and/or injected, the needle is withdrawn from the patient and/or retracted into the pre-use bounds of the apparatus. At activity 10800, the apparatus is rendered unusable for additional injections and/or indicated as previously utilized.

Figure 11:
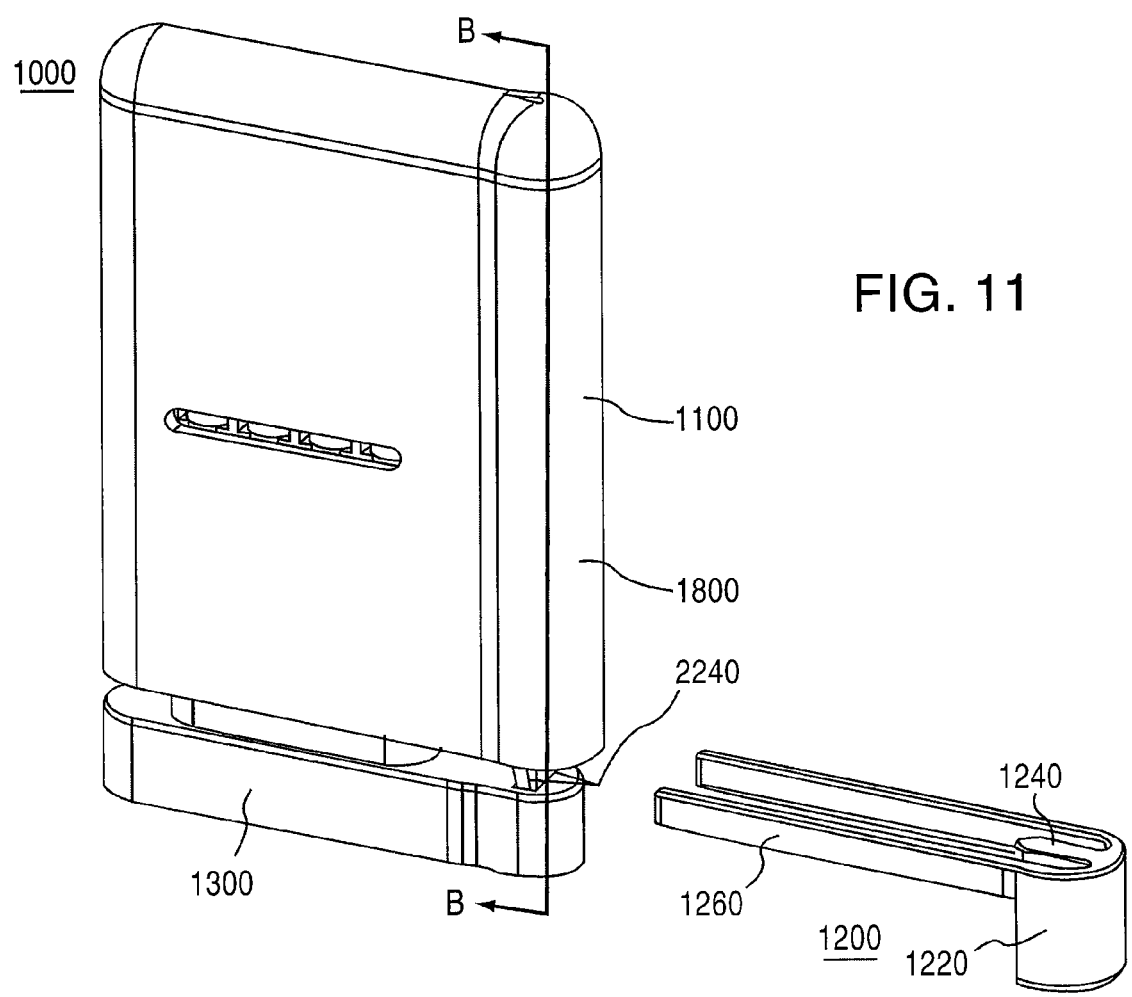
FIG. 11 is a perspective view of a system according to an embodiment of the invention.

FIG. 11 is a perspective view of an embodiment of system 1000, showing actuation guard 1200 removed from housing 1100, so that actuation guard 1200 no longer separates actuator bar 1300 from handheld portion 1800. Actuation guard 1200 can comprise a grippable portion 1220 that can be gripped by a user to pull actuation guard 1200 away from housing 1100, thereby allowing system 1000 to be activated, such as via slapping actuator bar 1300 against a thigh of the user. Actuation guard 1200 can comprise an actuation stick separator portion 1240, that can keep separate actuation stick prongs 2240 when actuation guard 1200 is installed on housing 1100. Actuation guard 1200 can comprise a guard portion 1260 that can separate actuator bar 1300 from handheld portion 1800 when system 1000 is not in use and/or when system 1000 has not been used.

Figure 12:
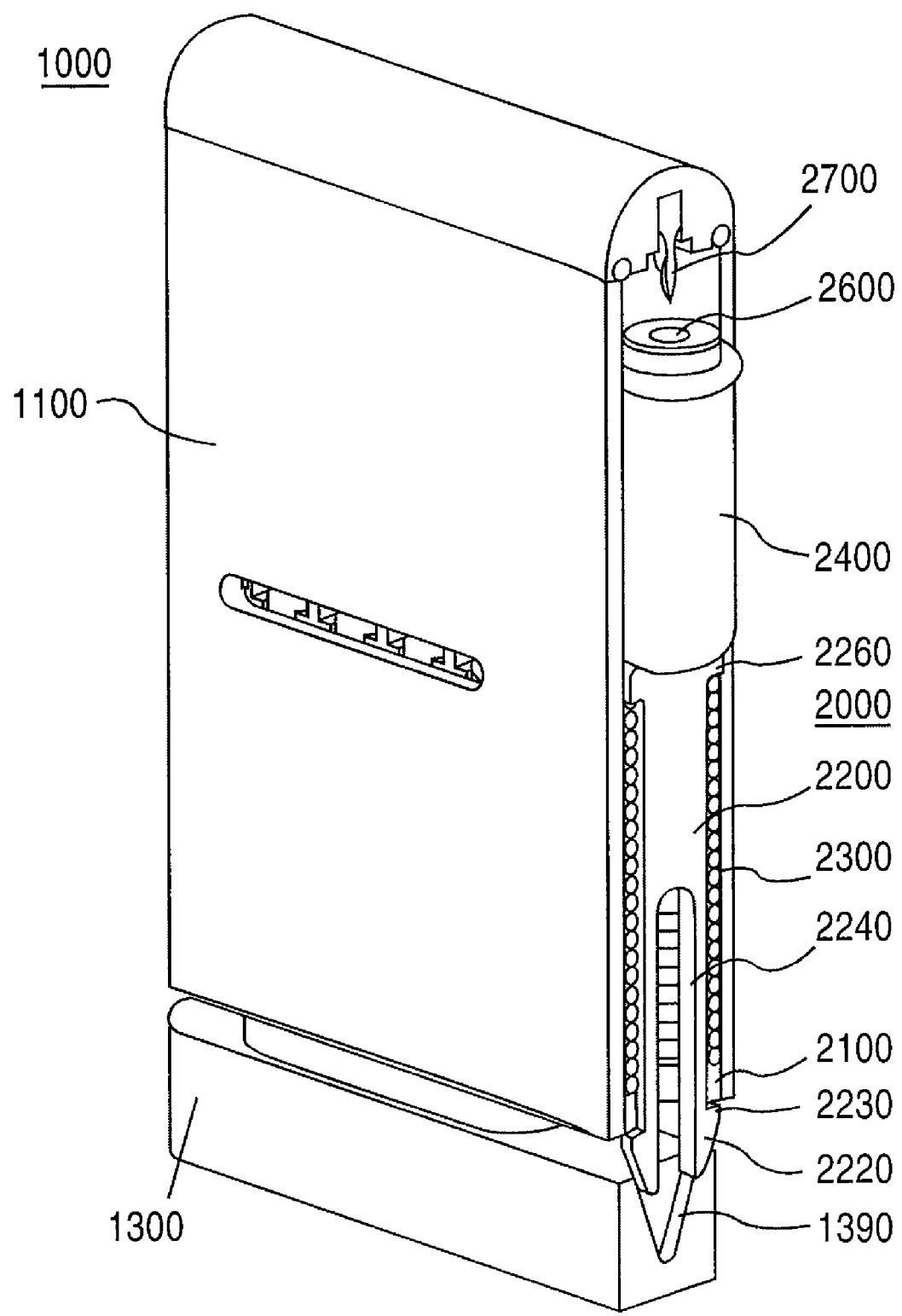
FIG. 12 is a perspective cross-sectional view the system illustrated in FIG. 11 taken along line B-B of FIG. 11.
Figure 13:
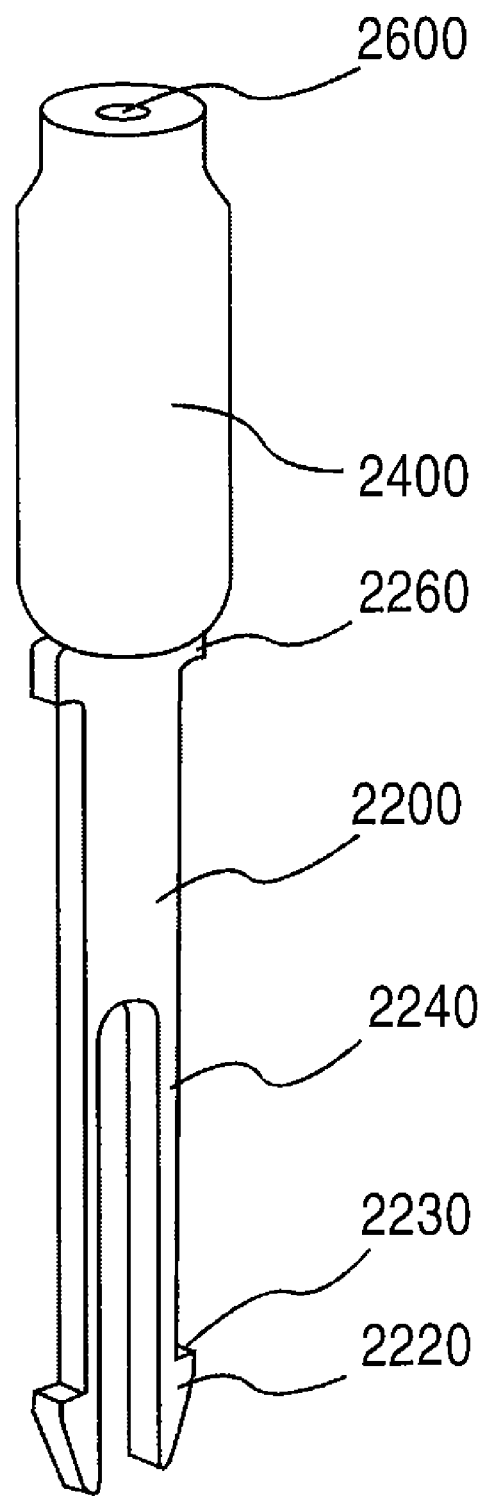
FIG. 13 is a perspective view of an apparatus according to an embodiment of the invention.

FIG. 12 is a perspective cross-sectional view taken along line B-B of FIG. 11, and FIG. 13 is a perspective view of an embodiment of actuation stick 2200. Referring to FIGS. 12 and 13, system 1000 can comprise housing 1100, actuation bar 1300, and system actuator 2000, which can comprise prong squeezer 1390, actuation stick 2200, prong retainer 2100, spring 2300, upper spring retainer 2260, gas container 2400, gas port 2600, and/or puncturer 2700. When actuation bar 1300 is pressed firmly against a user's body, such as via slapping housing actuation bar against the user's thigh, buttocks, and/or arm, prong squeezer 1390 can urge prong tips 2220 of prongs 2240 of actuation stick 2200 toward one another. Note that prong tips 2200 can have a triangular, wedge, angular, and/or frusto-conical shape. As prongs tips 2220 slide along the angled V-groove of prong squeezer 1390, prong catches 2230 can substantially lose contact with prong retainer 2100. This can allow compressed spring 2300 to rapidly urge actuation stick 2200 and gas container 2400 toward puncturer 2700, which can penetrate gas port 2600, thereby allowing gas to escape from gas container 2400. Although any of many different types of gas containers can be utilized, an example of a suitable gas container can be obtained from Leland Limited, Inc. of South Plainfield, N.J.

Figure 14:
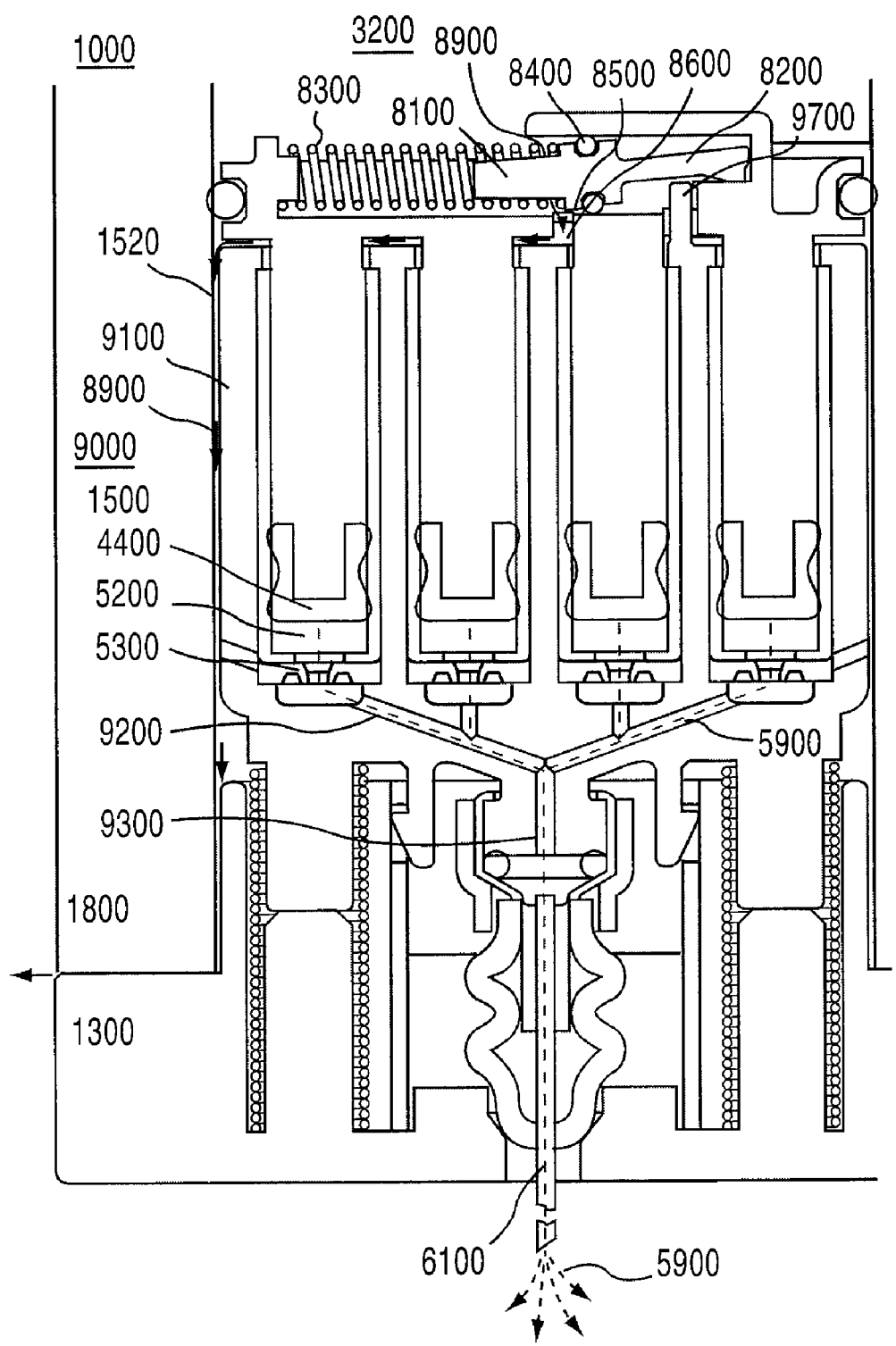
FIG. 14 is a cross-sectional view of a mechanism according to an embodiment of the invention taken along line A-A of FIG. 3.

FIG. 14 is a cross-sectional view of an embodiment of gas venting mechanism 8000 of system 1000 taken along line A-A of FIG. 3. System 1000 can comprise handheld portion 1800, actuator bar 1300, sleeve 1500. As pistons 4440 near the limit of their travels, medicament 5200 can be expelled along medicament path 5900, which can extend past frangible seal 5300, through medicament channels 9200, medicament conduit 9300, and needle 6100, and into the body of a user, such as subcutaneously, intramuscularly, and/or at a depth of from approximately 0.25 millimeters to approximately 20 millimeters, including all values and subranges therebetween, such as up to 2 millimeters, greater than 5 millimeters, etc.

As pistons 4440 near the limit of their travels, engagement of gas release actuator 9700 with gas relief valve 8200 can cause compressed spring 8300 to move valve arm such that o-ring 8400 is urged away from its seat 8500. This movement can reveal a passage 8600, via which gas can exit gas chamber 3200 along gas exhaust path 8900, which can extend between sleeve inner walls 1520 and outer walls 9100 of medicament carrier 9000. Eventually, gas exhaust path 8900 can extend between handheld portion 1800 and actuator bar 1300. Likewise, an alternative embodiment of valve 8200, made of rubber or any other resilient material, can be placed across seat 8500 to provide a seal that, once gas release actuator 9700 interacts with valve 8200, allows valve 8200 to bend or flap upwards away from seat 8500, causing the gas to escape via passage 8600.

Figure 15:
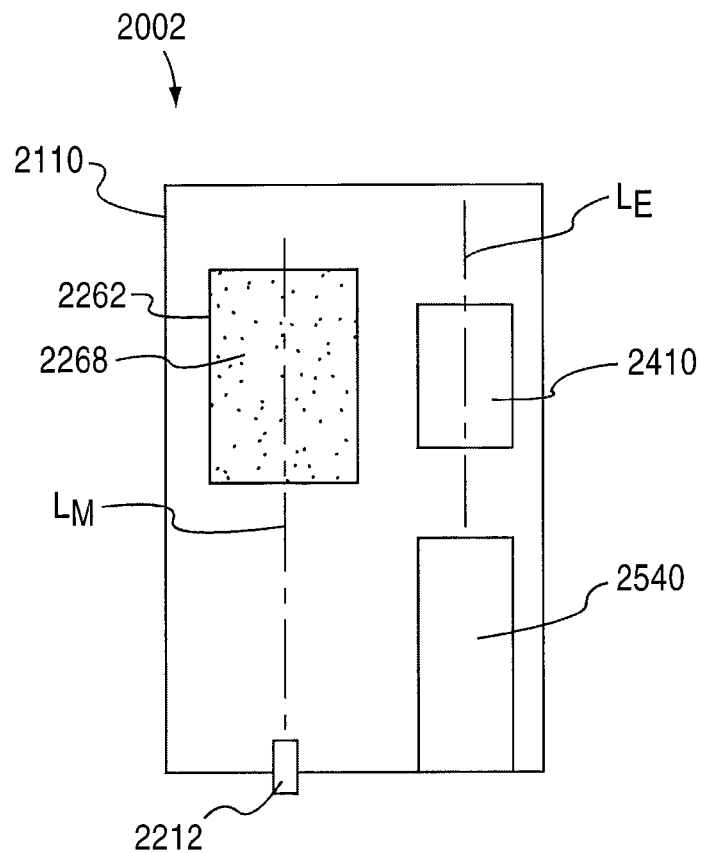
FIGS. 15 and 16 are schematic illustrations of an auto-injector according to an embodiment of the invention in a first configuration and a second configuration, respectively.
Figure 16:
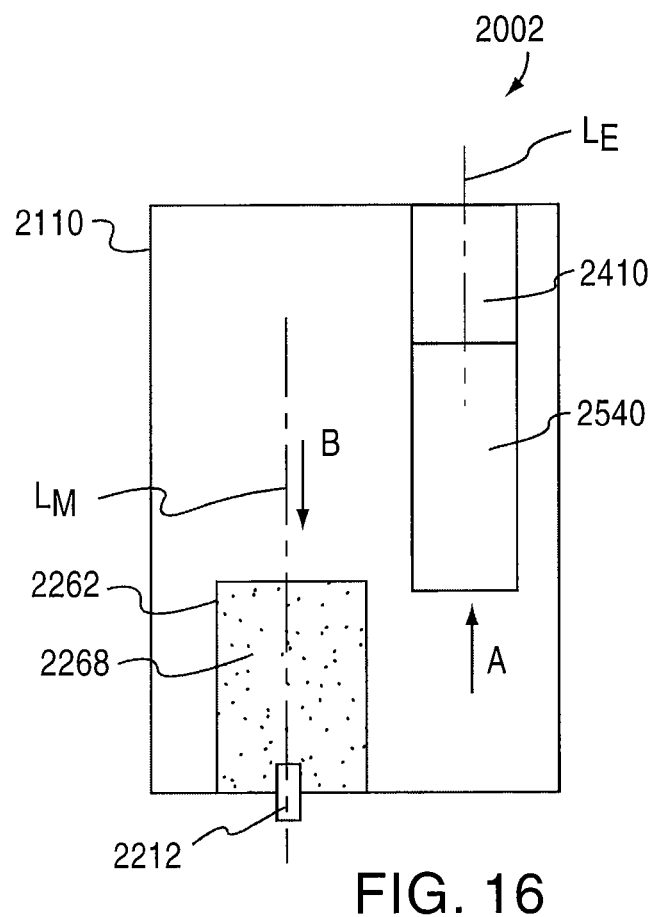

FIGS. 15 and 16 are schematic illustrations of an auto-injector 2002 according to an embodiment of the invention in a first configuration and a second configuration, respectively. The auto-injector 2002 includes a housing 2110 that contains a medicament container 2262, an energy storage member 2410, a release member 2540 and an injection member 2212. The medicament container 2262, which can be, for example, a pre-filled cartridge, a vial, an ampule or the like, is movably disposed within the housing 2110. The medicament container 2262 contains a medicament 2268, such as, for example, epinephrine. As illustrated, the medicament container 2262 can be moved, as indicated by arrow B in FIG. 16, along its longitudinal axis Lm between a first position (FIG. 15) and a second position (FIG. 16). When the medicament container 2262 is in its first (or retracted) position, the medicament container 2262 is spaced apart from the injection member 2212. When the medicament container 2262 is in the second (or advanced) position, the medicament container 2262 is placed in fluid communication with the injection member 2212. In this manner, when the medicament container 2262 is in the second (or advanced) position, the medicament 2268 can be conveyed via the injection member 2212 from the medicament container 2262 into a body of a patient. The injection member 2212 can be, for example, a needle, a nozzle or the like.

The energy storage member 2410, which can be any suitable device for storing energy, such as, for example, a spring, a battery, a compressed gas cylinder or the like, is also movably disposed within the housing 2110. As shown, the energy storage member 2410 defines a longitudinal axis Le that is offset from the longitudinal axis Lm of the medicament container 2262. The energy storage member 2410 can be moved, as indicated by arrow A in FIG. 16, within the housing 2110 along its longitudinal axis Le between a first position (FIG. 15) and a second position (FIG. 16). When the energy storage member 2410 is in its first position, the energy storage member 2410 has a first potential energy. When the energy storage member 2410 is in its second position, the energy storage member 2410 has a second potential energy that is less than the first potential energy. When the energy storage member 2410 moves from its first position to its second position, it converts at least a portion of its first potential energy into kinetic energy to move the medicament container 2262 between its first position and its second position.

Said another way, the movement of the energy storage member 2410 from its first position to its second position results in the production of a force that acts upon the medicament container 2262 to move the medicament container 2262 between its first position and its second position. The non-coaxial relationship between the longitudinal axis Lm of the medicament container 2262 and the longitudinal axis Le of the energy storage member 2410 allows the medicament container 2262 and the energy storage member 2410 to be arranged within the housing 2110 in any number of different configurations. In this manner, the auto-injector 2002 can have any number of different sizes and shapes, such as, for example, a substantially rectangular shape.

The release member 2540 is disposed within the housing 2110 and is configured to selectively deploy the energy storage member 2410 from its first position to its second position. The release member 2540 can be any suitable mechanism for moving the energy storage member 2410, such as, for example, a mechanical linkage, a spring-loaded rod or the like. In this manner, a user can actuate the auto-injector by manipulating a portion of the release member 2540.

Figure 17:
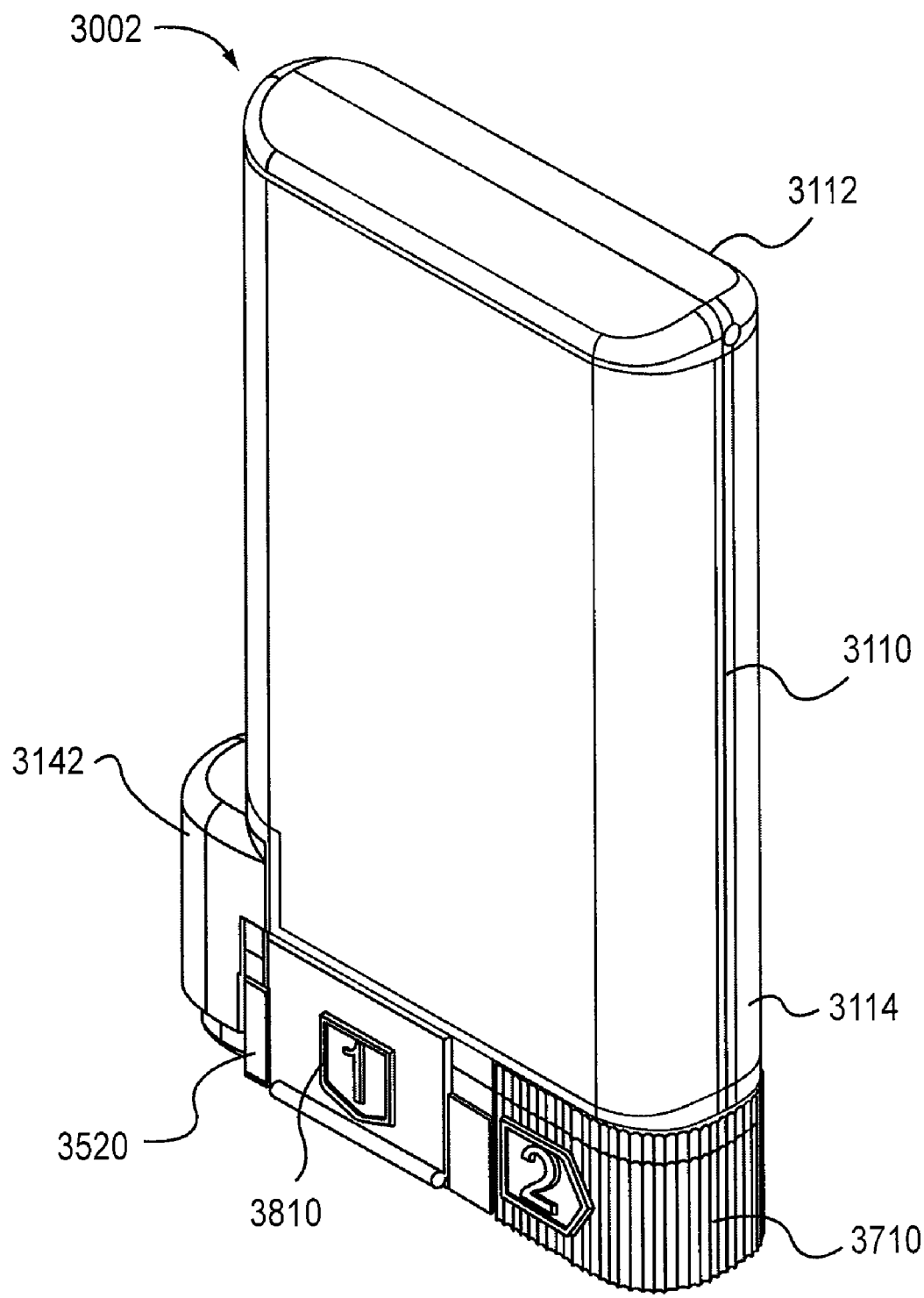
FIG. 17 is a perspective view of an auto-injector according to an embodiment of the invention.

FIG. 17 is a perspective view of an auto-injector 3002 according to an embodiment of the invention in a first configuration. The auto-injector 3002 includes a housing 3110 having a proximal end portion 3112 and a distal end portion 3114. The distal end portion 3114 of the housing 3110 includes a protrusion 3142 to help a user grasp and retain the housing 3110 when using the auto-injector 3002. Said another way, the protrusion 3142 is configured to prevent the auto-injector 3002 from slipping from the user's grasp during use. A base 3520 is movably coupled to the distal end portion 3114 of the housing 3110. A needle guard assembly 3810 is removably coupled to the base 3520. Similarly, a safety lock 3710 is removably coupled to the base 3520. To inject a medicament into the body, the distal end portion 3114 of the housing is oriented towards the user such that the base 3520 is in contact with the portion of the body where the injection is to be made. The base 3520 is then moved towards the proximal end 3112 of the housing 3110 to actuate the auto-injector 3002. The housing 3110 also includes a transparent status window 3118 (see FIG. 36) to allow a user to determine the status of the auto-injector 3002 or the medicament contained therein.

Figure 18:
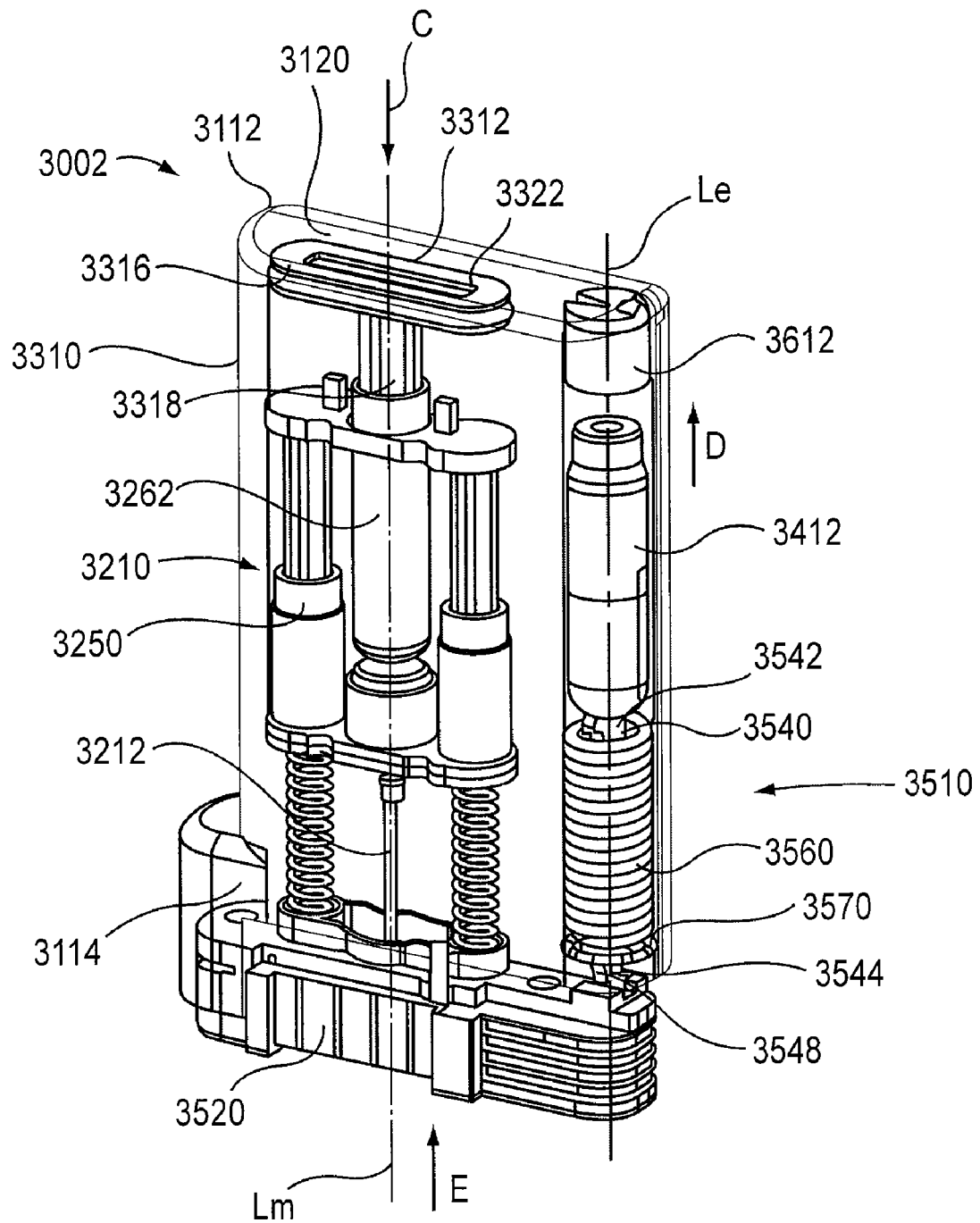
FIG. 18 is a perspective view of the auto-injector illustrated in FIG. 17 in a first configuration, with at least a portion of the auto-injector illustrated in phantom lines for ease of reference.
Figure 19:
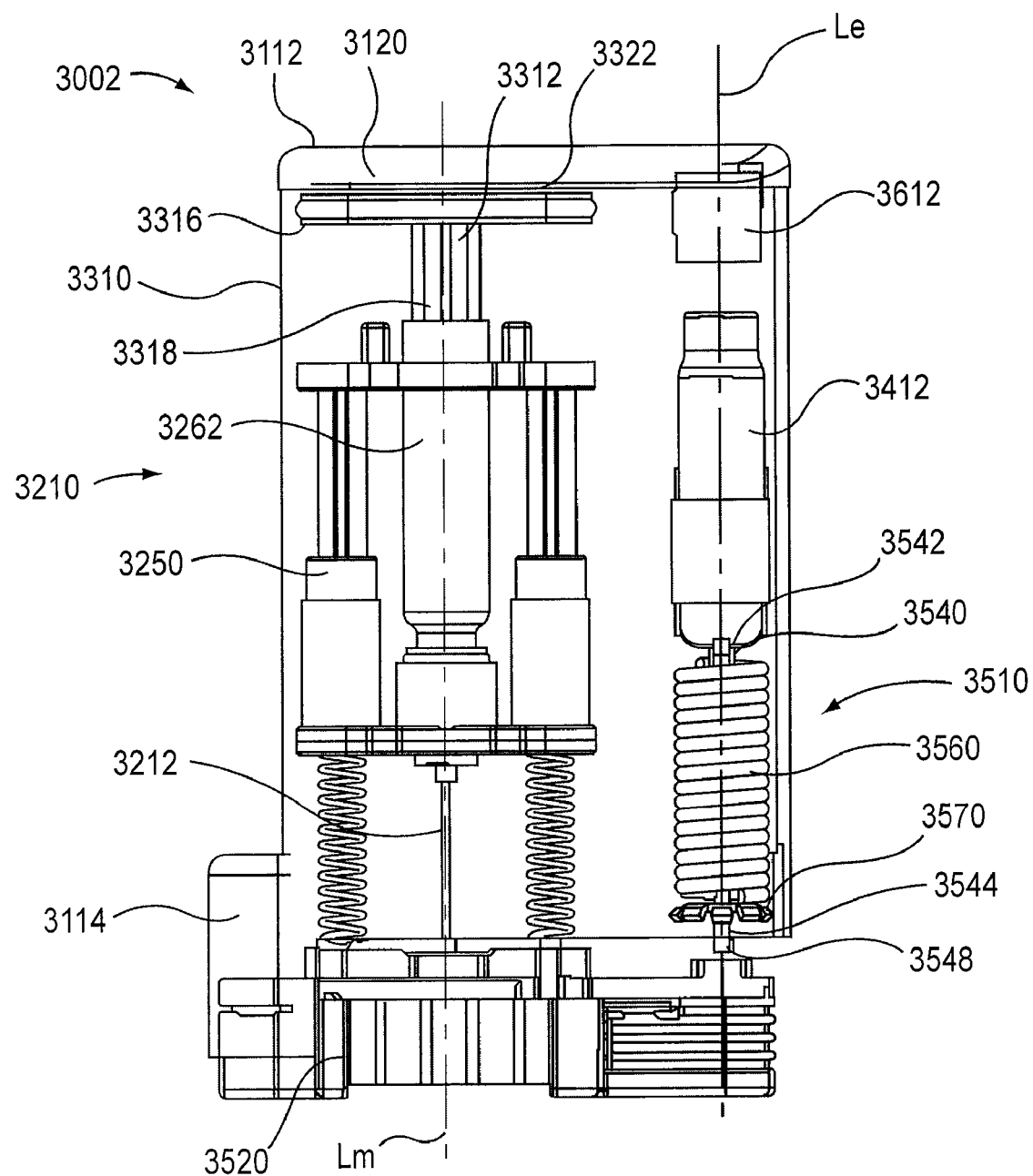
FIG. 19 is a front view of the auto-injector illustrated in FIGS. 17 and 18 in a first configuration.

FIG. 18 is a perspective view of the auto-injector 3002 showing the housing 3110 in phantom lines so that the components contained within the housing 3110 can be more clearly seen. For clarity, FIG. 18 shows the auto-injector 3002 without the needle guard assembly 3810 and the safety lock 3710. Similarly, FIG. 19 is a front view of the auto-injector 3002 showing the housing 3110 in phantom lines. The auto-injector 3002 includes a medicament injector 3210 and a movable member 3312 engaged with the medicament injector 3210, each of which are disposed within the housing 3110. The auto-injector 3002 also includes a system actuator 3510, a compressed gas container 3412 and a gas release mechanism 3612.

The medicament injector 3210 includes a carrier 3250 that is movable within the housing 3110, a medicament container 3262 and a needle 3212. The medicament container 3262 is coupled to the carrier 3250. The needle 3212 is disposed within a needle hub portion 3223 (see FIG. 22) of the carrier to allow the needle 3212 to be placed in fluid communication with the medicament container 3262 during an injection event.

The movable member 3312 includes a proximal end portion 3316 and a distal end portion 3318. The proximal end portion 3316 includes a surface 3322 that, together with the housing 3110, defines a gas chamber 3120. Said another way, the surface 3322 defines a portion of a boundary of the gas chamber 3120. The distal end portion 3318 is disposed within the medicament container 3262. In use, the movable member 3312 moves towards the distal end portion 3114 of the housing 3110, as indicated by arrow C, in response to a force produced by a pressurized gas on the surface 3322 of the movable member 3312. As a result, the movable member 3312 and the medicament injector 3250 are moved towards the distal end portion 3114 of the housing 3110, thereby exposing the needle 3212 from the housing 3110. The movable member 3312 then continues to move within the medicament container 3262 to expel a medicament from the medicament container 3262 through the needle 3212.

The auto-injector 3002 is actuated by the system actuator 3510, which is configured to move the compressed gas container 3412 into contact with the gas release mechanism 3612. The gas release mechanism 3612 punctures a portion of the compressed gas container 3412 to release the pressurized gas contained therein into the gas chamber 3120 defined by the housing 3110.

The system actuator 3510 includes a rod 3540, a spring 3560 and a spring retainer 3570. The rod 3540 has a proximal end portion 3542 and a distal end portion 3544. The proximal end portion 3542 of the rod 3540 is coupled to the compressed gas container 3412. The distal end portion 3544 of the rod 3540 is coupled to the spring retainer 3570 by two projections 3548, which can be moved inwardly towards each other to decouple the rod 3540 from the spring retainer 3570, as discussed below.

The spring 3560 is disposed about the rod 3540 in a compressed state such that the spring 3560 is retained by the proximal end portion 3542 of the rod 3540 and the spring retainer 3570. In this manner, the rod 3540 is spring-loaded such that when the distal end portion 3544 of the rod 3540 is decoupled from the spring retainer 3570, the force of the spring 3560 causes the rod 3540, and therefore the compressed gas container 3412, to move proximally as indicated by arrow D and into contact with the gas release mechanism 3612.

The base 3520 defines an opening 3522 configured to receive a portion of the projections 3548 when the base is moved towards the proximal end 3112 of the housing 3110, as indicated by arrow E. When the projections 3548 are received within the opening 3522, they are moved together causing the distal end portion 3544 of the rod 3540 to be released from the spring retainer 3570.

As shown in FIGS. 18 and 19, the medicament injector 3210 defines a longitudinal axis Lm that is non-coaxial with the longitudinal axis Le defined by the compressed gas container 3412. Accordingly, the medicament injector 3210, the compressed gas container 3412 and the system actuator 3510 are arranged within the housing 3110 such that the housing has a substantially rectangular shape. Moreover, the non-coaxial relationship between the medicament injector 3210 and the compressed gas container 3412 allows the auto-injector 3002 to be actuated by manipulating the base 3520, which is located at the distal end portion 3114 of the housing 3110.

As discussed above, the use and actuation of the auto-injector 3002 includes several discrete operations. First, the auto-injector 3002 is enabled by removing the needle guard 3810 and the safety lock 3710 (see FIGS. 20 and 21). Second, the auto-injector 3002 is actuated by moving the base 3520 proximally towards the housing 3110. Third, when actuated, the compressed gas container 3412 engages the gas release mechanism 3612, which causes the pressurized gas to be released into the gas chamber 3120 (see FIG. 31). Fourth, the pressurized gas produces a force that causes the movable member 3312 and the medicament injector 3210 to move distally within the housing 3110 (see FIG. 37). The movement of the medicament injector 3210 causes the needle 3212 to extend from distal end portion 3114 of the housing 3110 and the base 3520. This operation can be referred to as the "needle insertion" operation. Fifth, when the medicament injector 3210 has completed its movement (i.e., the needle insertion operation is complete), the movable member 3312 continues to move the medicament container 3262 distally within the carrier 3250. The continued movement of the medicament container 3262 places the needle 3212 in fluid communication with the medicament container 3262, thereby allowing the medicament to be injected (see FIG. 43). Sixth, the force from the pressurized gas causes the movable member 3312 to move within the medicament container 3262, thereby expelling the medicament through the needle 3212 (see FIG. 44). This operation can be referred to as the "injection operation." Seventh, upon completion of the injection, the pressurized gas is released from the gas chamber 3120, thereby allowing the medicament injector 3210 and the movable member 3312 to be moved proximally within the housing. This operation can be referred to as the "retraction operation" (see FIG. 45). A detailed description of the components contained in the auto-injector 3002 and how they cooperate to perform each of these operations is discussed below.

Prior to use, the auto-injector 3002 must first be enabled by first removing the needle guard 3810 and then removing the safety lock 3710. As illustrated by arrow G in FIG. 20, the needle guard 3810 is removed by pulling it distally. Similarly, as illustrated by arrow H in FIG. 21, the safety lock 3710 is removed by pulling it substantially normal to the longitudinal axis Le of the compressed gas container 3412. Said another way, the safety lock 3710 is removed by moving it in a direction substantially normal to the direction that the needle guard 3810 is moved. As described in more detail herein, the needle guard 3810 and the safety lock 3710 are cooperatively arranged to prevent the safety lock 3710 from being removed before the needle guard 3810 has been removed. Such an arrangement prevents the auto-injector 3002 from being actuated while the needle guard 3810 is in place.

Figure 22:
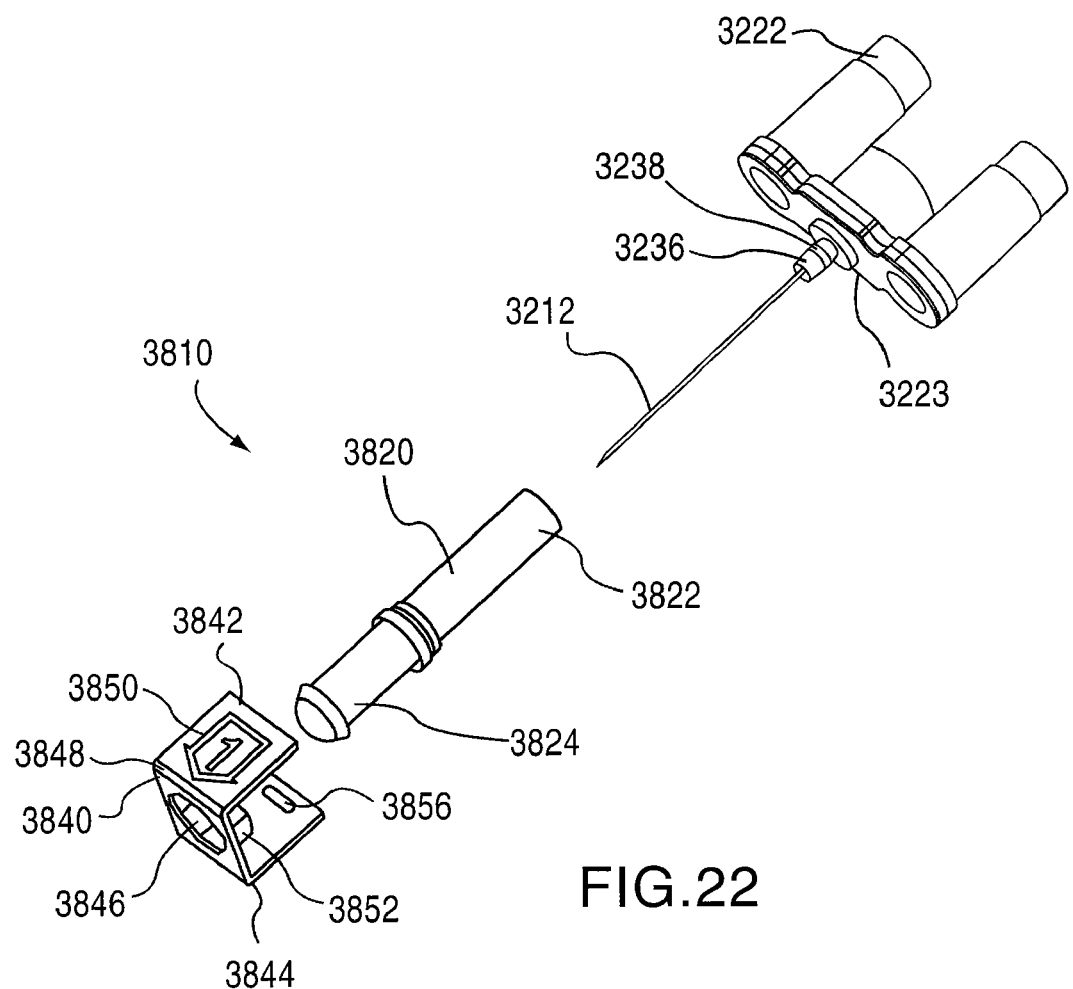
FIG. 22 is an exploded perspective view of the a portion of the auto-injector illustrated in FIG. 20.

As illustrated in FIG. 22, the needle guard 3810 includes a sheath 3820 and a sheath retainer 3840. The sheath 3820 has a proximal end portion 3822 and a distal end portion 3824 and defines an opening 3826 configured to receive a portion of the needle 3212 when the needle guard 3810 is in a first (or installed) position. The sheath 3820 further defines a recessed portion 3828 within the opening 3826 that engages a corresponding protrusion 3238 defined by an outer surface 3236 of the needle hub 3223. In this manner, when the needle guard 3810 is in its first position, the sheath 3820 is removably coupled to the needle hub 3223. In some embodiments, the recessed portion 3828 and the protrusion 3238 form a seal that is resistant to microbial penetration.

Figure 20:
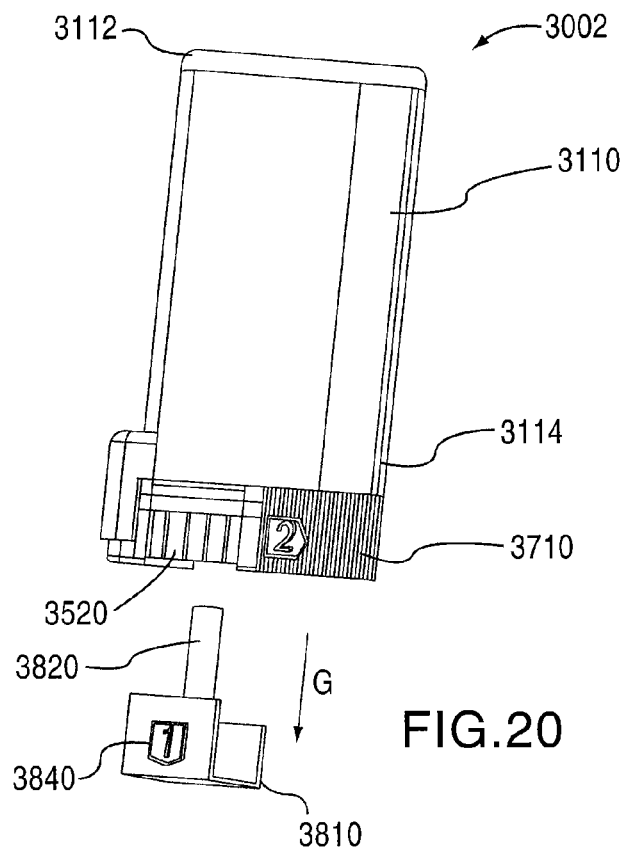
FIG. 20 is a perspective view of the auto-injector illustrated in FIG. 17 showing an assembly according to an embodiment of the invention being removed.

The sheath retainer 3840 has a proximal portion 3842 and a distal portion 3844. The proximal portion 3842 of the sheath retainer 3840 includes a protrusion 3856 that engages a corresponding recess 3526 in the base 3520 (see FIG. 28) to removably couple the sheath retainer 3840 to the base 3520. The distal portion 3844 of the sheath retainer 3840 defines an opening 3846 through which the distal end portion 3824 of the sheath 3820 is disposed. The distal portion 3844 of the sheath retainer 3840 includes a series of retaining tabs 3852 that engage the distal end portion 3824 of the sheath 3820 to couple the sheath 3820 to the sheath retainer 3840. In this manner, when the sheath retainer 3840 is moved distally away from the base 3520 into a second (or removed) position, as shown in FIG. 20, the sheath 3820 is removed from the needle 3412. Moreover, this arrangement allows the sheath 3820 to be disposed about the needle 3412 independently from when the sheath retainer 3840 is coupled to the sheath 3820. As such, the two-piece construction of the needle guard provides flexibility during manufacturing. The distal portion 3844 of the sheath retainer 3840 also includes a protrusion 3848 to aid the user when grasping the needle guard 3810.

Figure 25:
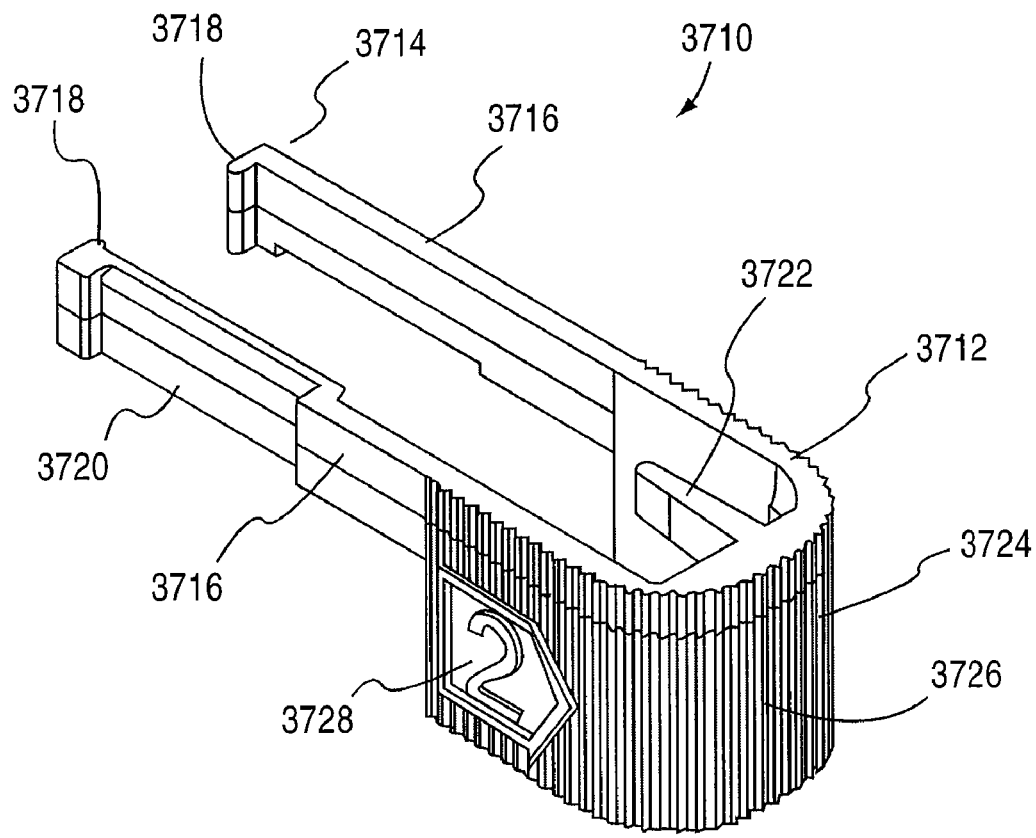
FIG. 25 is a perspective view of a member of the auto-injector illustrated in FIG. 21.

When the needle guard 3810 is in its first position, the sheath retainer 3840 is disposed within a recess 3720 defined by one of the extended portions 3716 of the safety lock 3710 (see FIG. 25). This arrangement prevents the safety lock 3710 from being removed when the needle guard 3810 is in its first position, which in turn, prevents the auto-injector 3002 from being actuated when the needle guard 3810 is in its first position.

Figure 21:
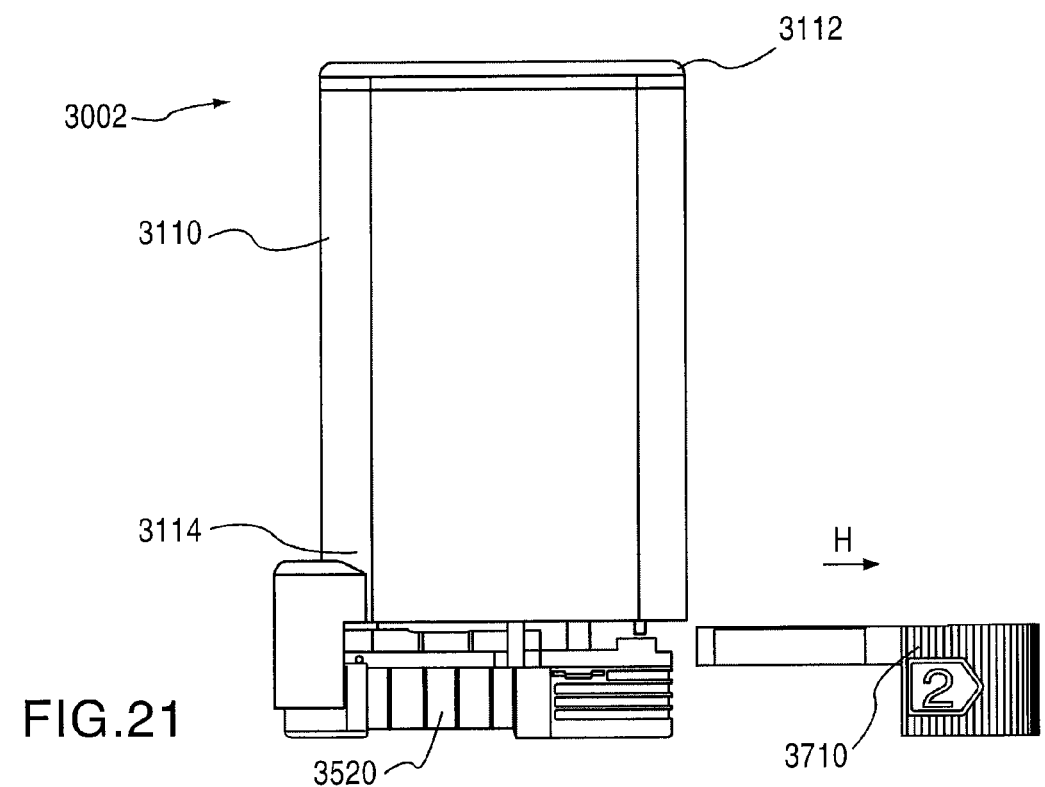
FIG. 21 is a front view of the auto-injector illustrated in FIG. 17 showing a member according to an embodiment of the invention being removed.

The outer surface of the sheath retainer 3840 includes an indicia 3850 to instruct the user in operating the auto-injector 3002. As shown in FIG. 21, the indicia 3850 includes a numeral to indicate the order of operation and an arrow to indicate the direction in which the needle guard 3810 should be moved. In some embodiments, the indicia 3850 can include different colors, detailed instructions or any other suitable indicia to instruct the user. In other embodiments, the indicia 3850 can protrude from the sheath retainer 3840 to aid the user when grasping the needle guard 3810.

In some embodiments, the sheath 3820 can be constructed from any suitable material, such as, for example polypropylene, rubber or any other elastomer. In some embodiments, the sheath 3820 can be constructed from a rigid material to reduce the likelihood of needle sticks during the manufacturing process. In other embodiments, the sheath 3820 can be constructed from a flexible material.

Figure 26:
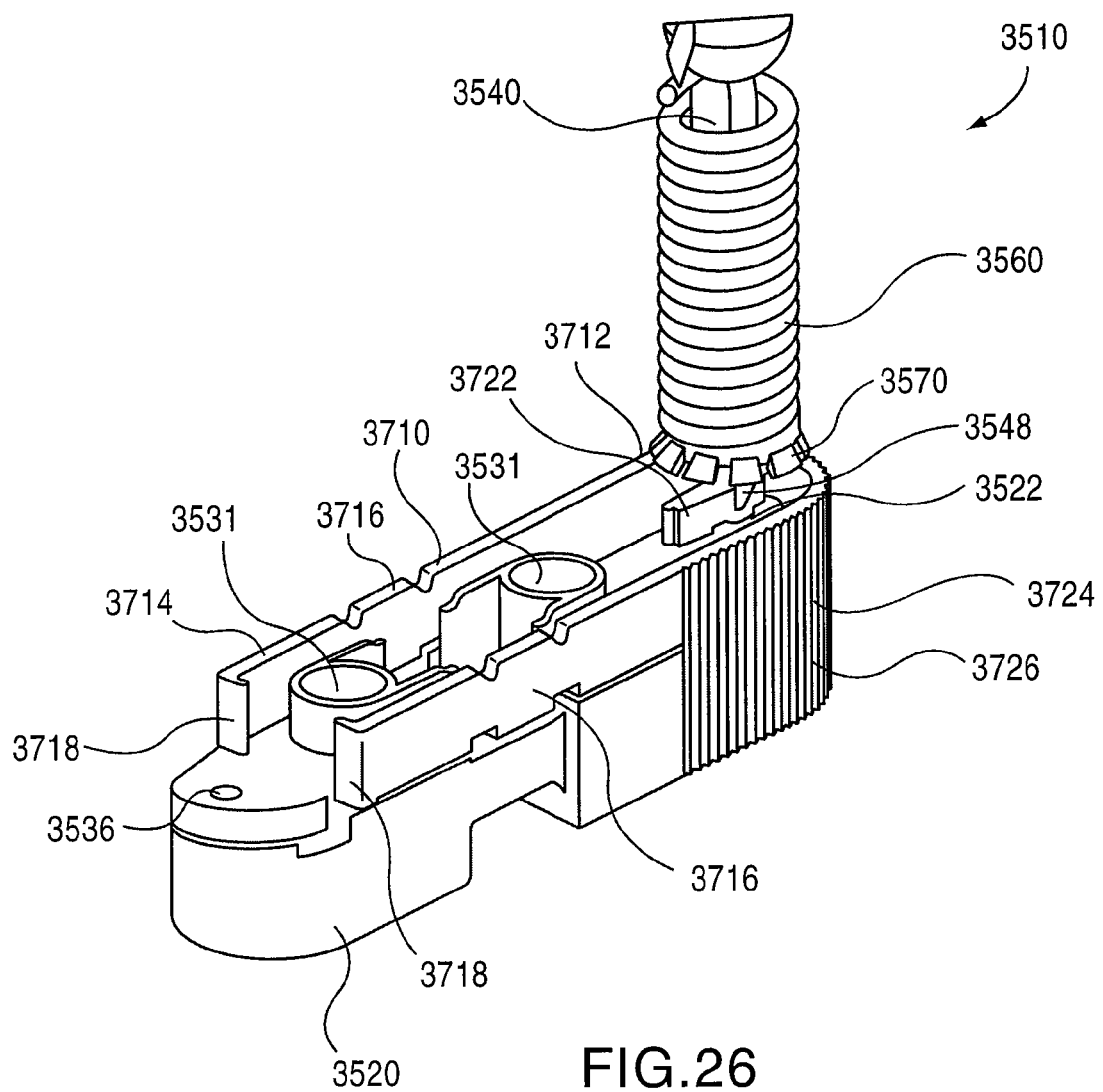
FIG. 26 is a perspective view of a portion of the auto-injector illustrated in FIGS. 17 and 21.

After the needle guard 3810 is removed, the user must then remove the safety lock 3710, as indicated in FIG. 21. As shown in FIG. 25, the safety lock 3710 is a U-shaped member having a first end 3712 and a second end 3714. The second end 3714 of the safety lock 3710 includes two extended portions 3716, each of which includes an inwardly facing protrusion 3718. When the safety lock 3710 is in its first (or locked) position, the extended portions 3716 extend around a portion of the base 3520 to space the base 3520 apart from the distal end portion 3114 of the housing 3110. As shown in FIG. 26, the protrusions 3718 are configured engage a portion of the base 3520 to removably couple the safety lock 3710 in its first position.

One of the extended portions 3716 defines a recess 3720 that receives the sheath retainer 3840 when the needle guard 3810 is in its first position, as discussed above. Although only one extended portion 3716 is shown as including a recess 3720, in some embodiments both extended portions 3716 can include a recess 3720 to receive the sheath retainer 3840. In other embodiments, the safety lock 3710 can be engaged with the needle guard 3810 to prevent movement of the safety lock 3710 when the needle guard 3810 is in place in any suitable manner. For example, in some embodiments, the sheath retainer can include protrusions that are received within corresponding openings defined by the safety lock. In other embodiments, the safety lock can include protrusions that are received within corresponding openings defined by the sheath retainer.

The first end 3712 of the safety lock 3710 includes a locking protrusion 3722 that extends inwardly. As shown in FIG. 26, when the safety lock 3710 is in its first position, the locking protrusion 3722 extends between the projections 3548 of the rod 3540 and obstructs the opening 3522 of the base 3520. In this manner, when the safety lock 3710 is in its first position, the base 3520 cannot be moved proximally to allow the projections 3548 to be received within the opening 3522. The arrangement of the locking protrusion 3722 also prevents the projections 3548 from being moved inwardly towards each other. Accordingly, when the safety lock 3710 is in its first position, the auto-injector 3002 cannot be actuated.

The outer surface 3724 of the first end 3712 of the safety lock 3710 includes a series of ridges 3726 to allow the user to more easily grip the safety lock 3710. The outer surface 3724 of the first end 3712 of the safety lock 3710 also includes an indicia 3728 to instruct the user in operating the auto-injector 3002. As shown in FIG. 25, the indicia 3728 includes a numeral to indicate the order of operation and an arrow to indicate the direction in which the safety lock 3710 should be moved. In some embodiments, the indicia 3728 can include different colors, detailed instructions or any other suitable indicia to instruct the user. In other embodiments, the indicia 3728 can protrude from the safety lock 3710 to aid the user when grasping the safety lock 3710.

Figure 27:
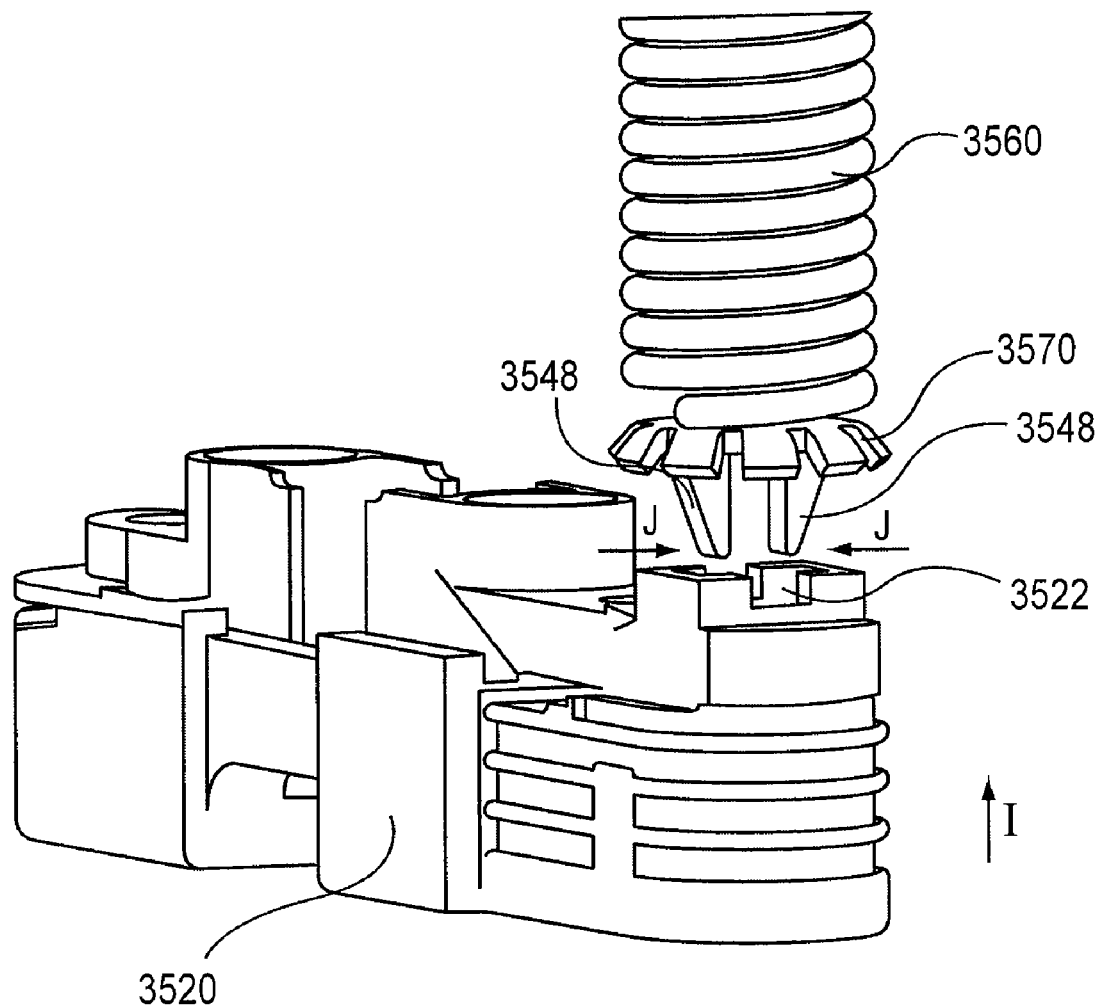
FIG. 27 is a perspective view of a portion of the auto-injector illustrated in FIGS. 17 and 26.
Figure 28:
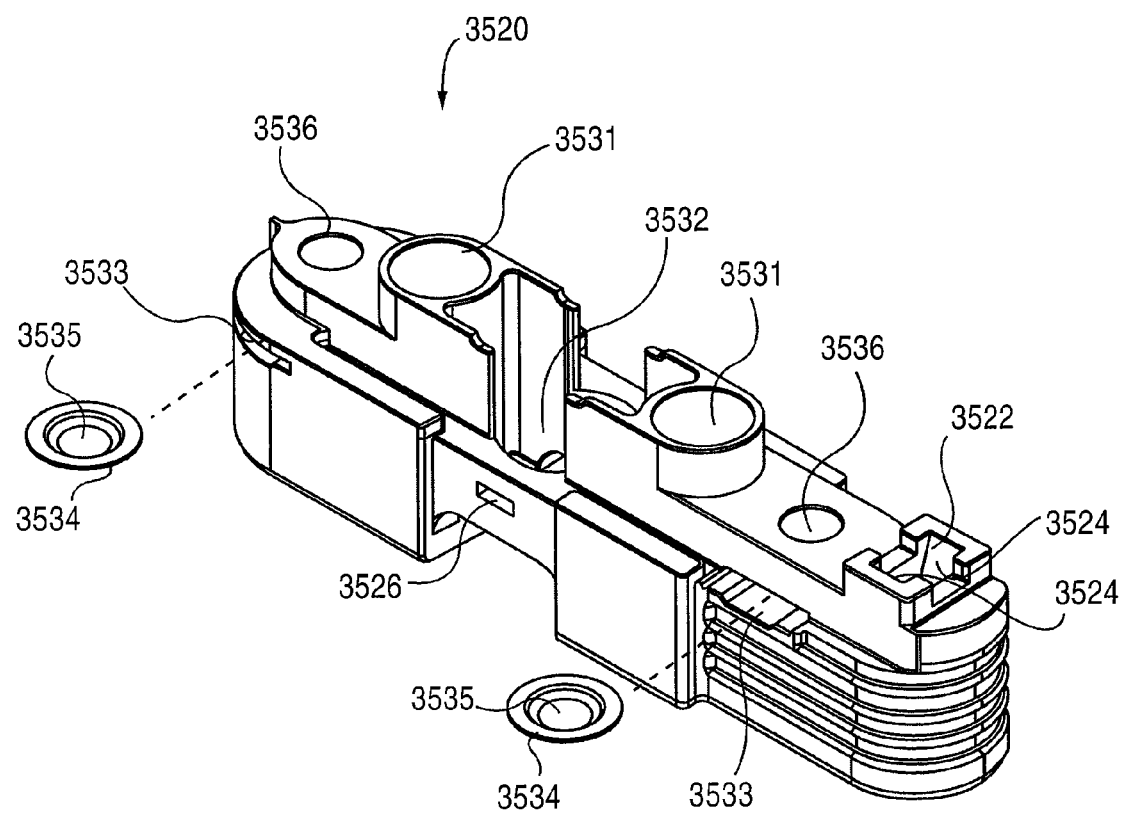
FIG. 28 is a partially exploded perspective view of a base of the auto-injector illustrated in FIG. 26.
Figure 36:
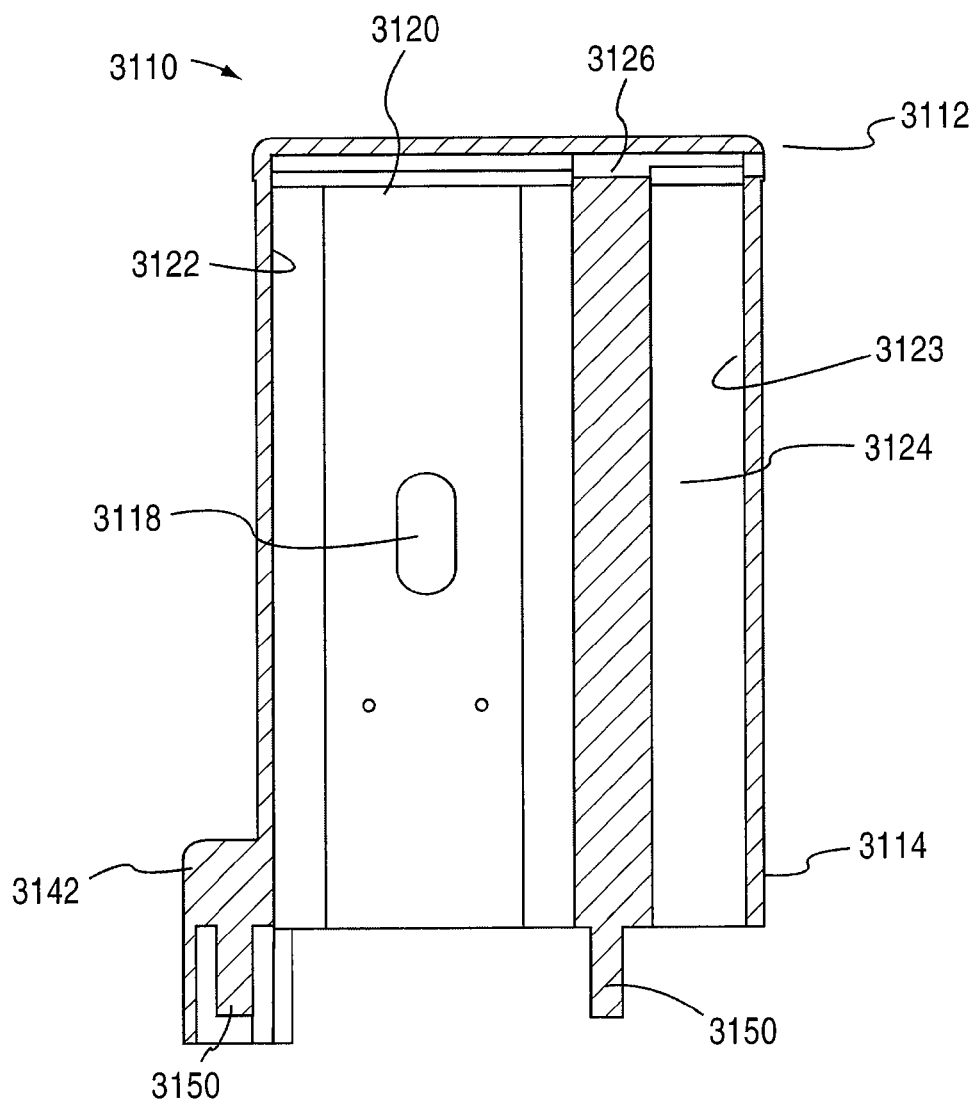
FIG. 36 is a cross-sectional view of the housing taken along line 36-36 in FIG. 35.

After being enabled, the auto-injector 3002 can then be actuated by moving the base 3520 proximally towards the housing 3110, as indicated by arrow I in FIG. 27. As shown in FIGS. 28 and 36, the base 3520 defines two openings 3536 that receive corresponding attachment protrusions 3150 disposed on the distal end portion 3114 of the housing 3110. In this manner, the movement and/or alignment of the base 3520 relative to the housing 3110 is guided by the attachment protrusions 3150 and the openings 3536 (see FIG. 36).

Each attachment protrusion 3150 is secured within its corresponding opening 3536 by a lock washer 3534. The lock washers 3534 each define an opening 3535 that receives a portion of the attachment protrusion 3150. The lock washers 3534 are disposed within slots 3533 defined by the base 3520 so that the openings 3535 are aligned with the attachment protrusions 3150. The openings 3535 are configured to allow the lock washers 3534 to move proximally relative to the attachment protrusions 3150, but to prevent movement of the lock washers 3534 distally relative to the attachment protrusions 3150. In this manner, when the attachment protrusions 3150 are disposed within the openings 3535 of the lock washers 3534, the base 3520 becomes fixedly coupled to the housing 3110. Moreover, after the base 3520 is moved proximally relative to the housing 3110, the lock washers 3534 prevent the base 3520 from returning to its initial position. Said another way, the arrangement of the lock washers 3534 prevents the base 3520 from being "kicked back" after the auto-injector 3002 has been actuated.

The base 3520 also defines a needle opening 3532, a recess 3526 and two retraction spring pockets 3531. The needle opening 3532 receives a portion of the needle guard 3810 when the needle guard is in its first position. Additionally, when the auto-injector is in its third configuration (see FIG. 37), the needle 3212 extends through the needle opening 3532. As described above, the recess 3526 receives the corresponding protrusion 3856 on the sheath retainer 3840 to removably couple the needle guard 3810 to the base 3520. As will be described in more detail herein, the retraction spring pockets 3531 receive a portion of the retraction springs 3350.

As shown in FIG. 28, the base 3520 includes two opposing tapered surfaces 3524 that define an opening 3522 configured to receive a corresponding tapered surface 3550 of the projections 3548 when the base is moved proximally towards the housing 3110. When the projections 3548 are received within the tapered opening 3522, they are moved together as indicated by arrows J in FIG. 27. The inward movement of the projections 3548 causes the rod 3540 to become disengaged from the spring retainer 3570, thereby allowing the rod 3540 to be moved proximally along its longitudinal axis as the spring 3560 expands. A more detailed description of the components included in the system actuator 3510 is provided below with reference to FIGS. 29 and 30.

The system actuator 3510 includes a rod 3540, a spring 3560 disposed about the rod 3540 and a spring retainer 3570. As described in more detail herein, the spring retainer 3570 retains both the spring 3560 and the rod 3540. The spring retainer 3570 includes a first surface 3572, a second surface 3574 and a series of outwardly extending engagement tabs 3576. The spring retainer 3570 is disposed within the gas container opening 3124 defined by the housing 3110 (see FIG. 36) such that the engagement tabs 3576 engage the interior surface 3123 of the housing 3110 to produce an interference fit. In this manner, the spring retainer 3570 is fixedly disposed within the housing 3110.

The rod 3540 has a proximal end portion 3542 and a distal end portion 3544. The distal end portion 3544 of the rod 3540 includes two extensions 3552 disposed apart from each other to define an opening 3554 therebetween. Each extension 3552 includes a projection 3548 having a tapered surface 3550 and an engagement surface 3549. When the rod 3540 is in its first (or engaged) position, the engagement surfaces 3549 engage the second surface 3574 of the spring retainer 3570 to prevent the rod 3540 from moving proximally along its longitudinal axis. As described above, when the base 3520 is moved proximally towards the housing 3110, the tapered surfaces 3550 of the projections 3548 cooperate with the corresponding tapered surfaces 3524 of the base 3520 to move the extensions 3552 inwardly towards each other. The inward motion of the extensions 3552 causes the engagement surfaces 3549 to become disengaged from the second surface 3574 of the spring retainer 3570, thereby allowing the rod 3540 to move between its first position to a second (or actuated) position.

The proximal end portion 3542 of the rod 3540 includes a retention portion 3545 having a first surface 3547 and a second surface 3546. The first surface 3547 of the retention portion 3545 engages the distal portion 3416 of the compressed gas container 3412. The second surface 3546 of the retention portion 3545 engages a proximal end 3562 of the spring 3560. Similarly, the first surface 3572 of the spring retainer 3570 engages a distal end 3564 of the spring 3560. In this manner, when the rod 3540 is in its first position, the spring 3560 can be compressed between the spring retainer 3570 and the retention portion 3545 of the rod 3540. Accordingly, when the rod 3540 is disengaged from the spring retainer 3570, the force imparted by the spring 3560 on the retention portion 3545 of the rod 3540 causes the rod 3540 to move proximally into its second position.

The proximal end portion 3542 of the rod 3540 is coupled to the compressed gas container 3412 by a connector 3580, which is secured to the distal end portion 3416 of the compressed gas container 3412 by a securing member 3588. The connector 3580 includes a proximal end portion 3582 and a distal end portion 3584. The distal end portion 3584 of the connector 3580 is disposed within the opening 3554 defined between the extensions 3552. In this manner, the connector 3580 is retained by the proximal end portion 3542 of the rod 3540. As will be described in more detail, the distal end portion 3584 of the connector 3580 includes locking tabs 3587.

The proximal end portion 3582 of the connector 3580 includes engagement portions 3586 that engage the distal end portion 3416 of the compressed gas container 3412. The engagement portions 3586 are coupled to the compressed gas container 3412 by the securing member 3588, which can be, for example, a shrink wrap, an elastic band or the like. In other embodiments, the engagement portions 3586 can produce an interference fit with the compressed gas container 3412, thereby eliminating the need for a securing member 3588.

Figure 31:
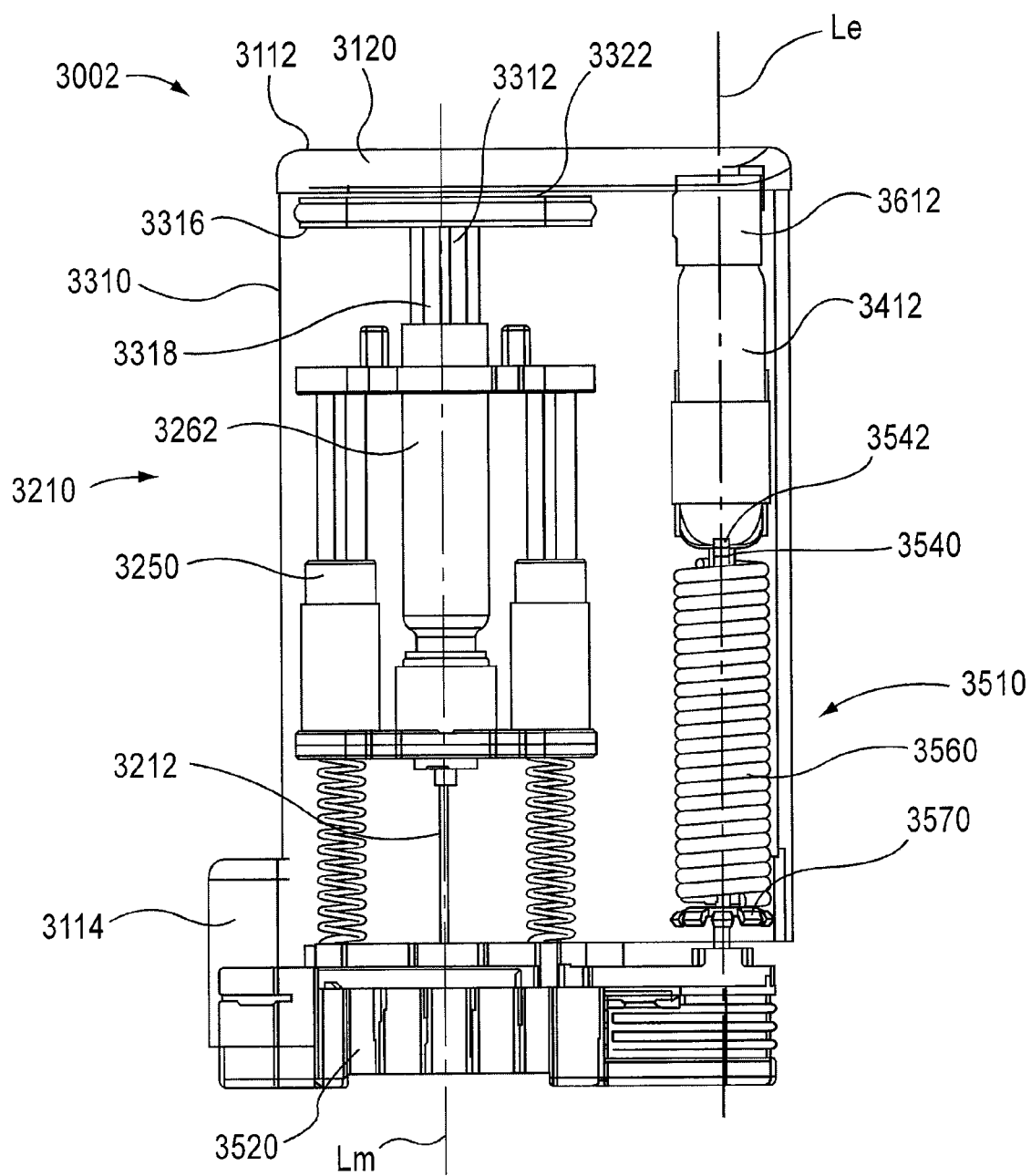
FIG. 31 is a front view of the auto-injector illustrated in FIG. 19 in a second configuration.

Because the rod 3540 is coupled to the compressed gas container 3412, when the rod 3540 is moved from its first (engaged) position to its second (actuated) position, the compressed gas container 3412 is moved proximally within the housing 3110 into engagement with the gas release mechanism 3612. FIG. 31 shows the auto-injector in a second configuration, in which the compressed gas container 3412 is engaged with the gas release mechanism 3612. When in the second configuration, the compressed gas contained within the compressed gas container 3412 is released to actuate the medicament injector 3210. A more detailed description of the gas release process is provided below with reference to FIGS. 32 through 36.

Figure 32:
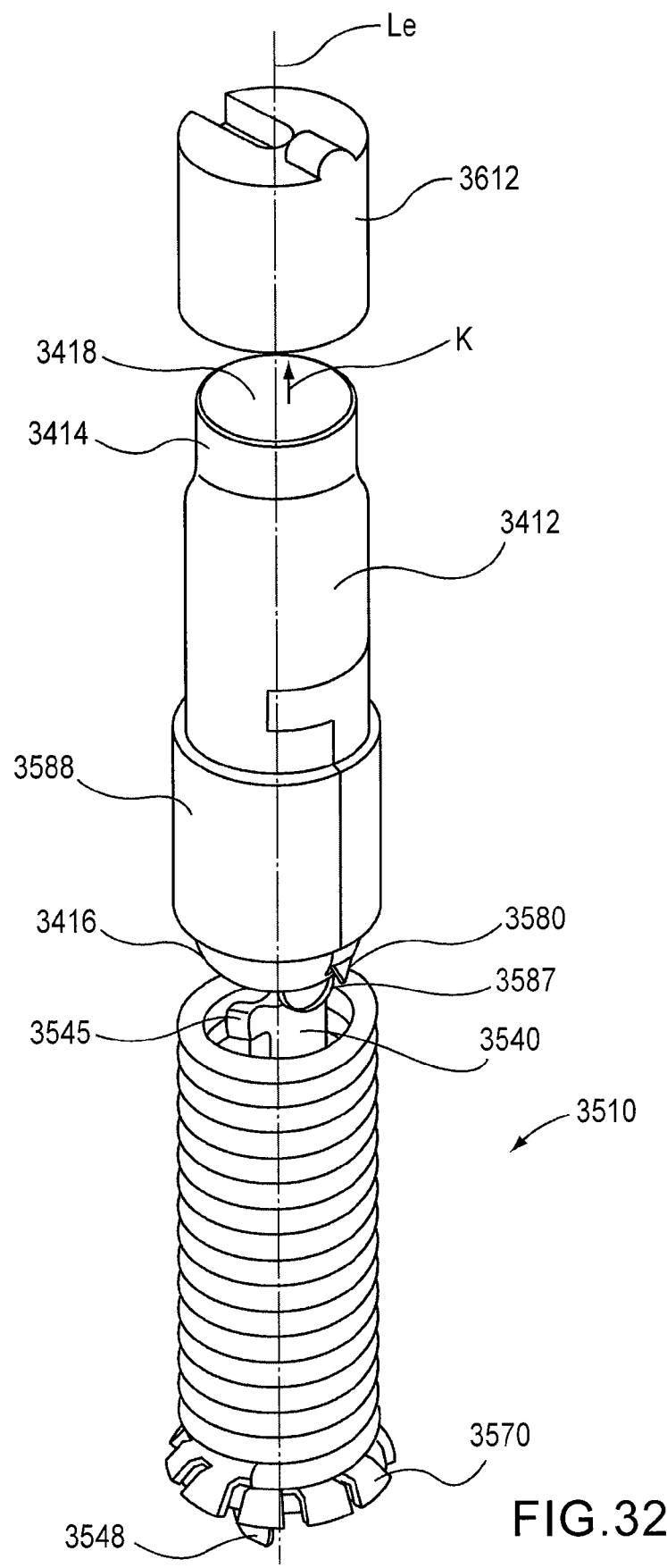
FIG. 32 is a perspective view of a portion of the auto-injector shown in FIG. 31.

FIG. 32 shows an exploded view of the system actuator 3510, the compressed gas container 3412 and the gas release mechanism 3612, each of which are disposed within the gas container opening 3124 defined by the housing 3110 (see FIG. 36). As shown, the compressed gas container 3412, the system actuator 3510 and the gas release mechanism 3612 are arranged substantially coaxial with each other. As previously discussed, when the auto-injector 3002 is actuated, the compressed gas container 3412 is moved proximally within the gas container opening 3124 defined by the housing 3110, as indicated by the arrow K in FIG. 32, until the proximal end 3414 of the compressed gas container 3412 engages the gas release mechanism 3612.

Figure 33:
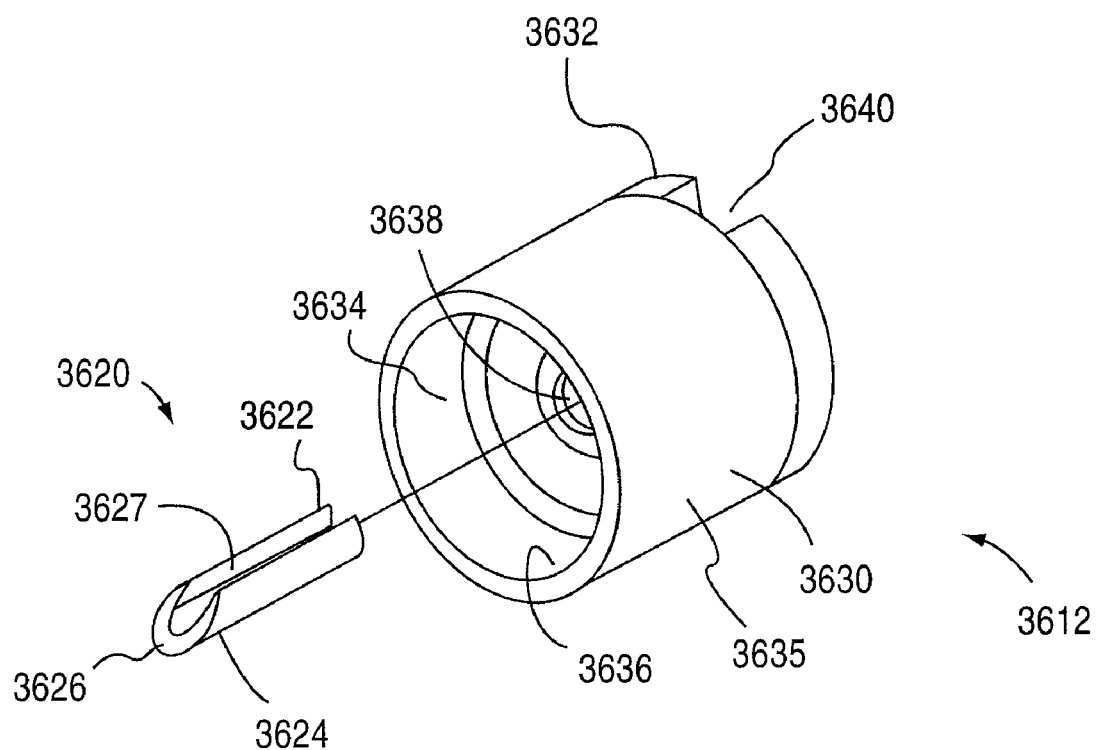
FIGS. 33 and 34 are perspective views of a portion of the auto-injector shown in FIG. 32.
Figure 34:
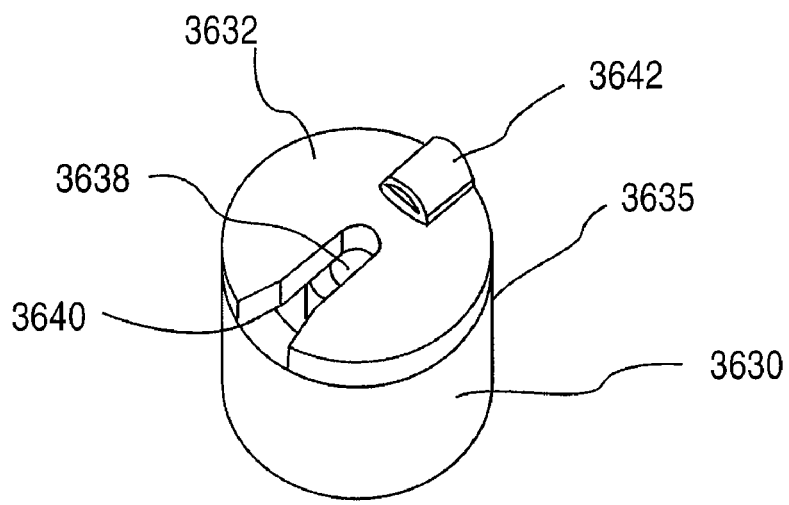
Figure 35:
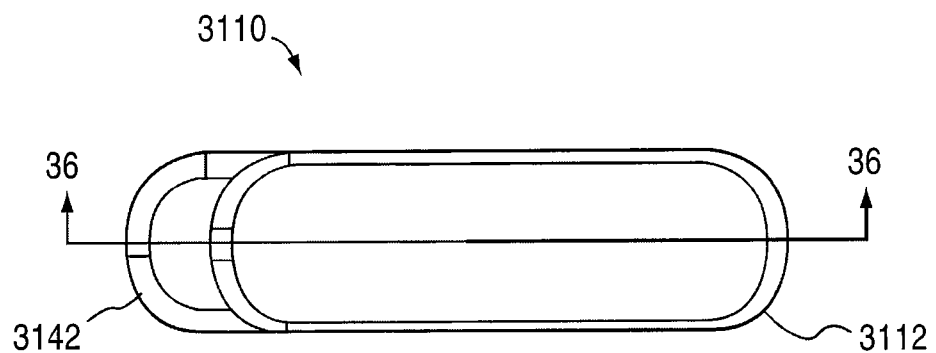
FIG. 35 is a top view of the housing of the auto-injector shown in FIG. 31.

As shown in FIGS. 33 and 34, the gas release mechanism 3612 includes a cap 3630 and a puncturing element 3620 coupled to and disposed within the cap 3630. The puncturing element has a proximal end 3622 and a distal end 3624. The distal end 3624 of the puncturing element 3620 defines a sharp point 3626 configured to puncture the proximal end 3414 of the compressed gas container 3412. The puncturing element 3620 defines an opening 3627 extending from its distal end 3624 to its proximal end 3622.

The cap 3630 has a proximal end 3632, an outer surface 3635 and an inner surface 3636. The inner surface 3636 of the cap 3630 defines an opening 3634 that receives the proximal end 3414 of the compressed gas container 3412 when the auto-injector 3002 is in its second configuration. The proximal end 3632 of the cap 3630 defines an opening 3638 therethrough and a channel 3640 in fluid communication with the opening 3638. The opening 3638 receives the proximal end 3622 of the puncturing element 3620 to couple the puncturing element 3620 to the cap 3630. The puncturing element 3620 is disposed within the cap 3630 such that when the compressed gas container 3412 is moved into the opening 3634, the distal end 3624 of the puncturing element 3620 punctures the proximal end 3414 of the compressed gas container 3412.

The cap 3630 is disposed within the gas container opening 3124 such that the outer surface 3635 of the cap 3630 engages the inner surface 3123 of the housing 3110. In some embodiments, the outer surface 3635 of the cap 3630 can be sized to produce an interference fit with the inner surface 3123 of the housing 3110. In other embodiments, the cap 3630 can be fixedly coupled within the gas container opening 3124 using an adhesive or any other suitable attachment mechanism.

The cap 3630 is oriented within the gas container opening 3124 so that the channel 3640 is aligned with and in fluid communication with the gas passageway 3126 defined by the housing 3110. Moreover, when oriented in this manner, the protrusion 3642 on the proximal end 3632 of the cap 3630 obstructs a portion of the gas passageway 3126, which can be manufactured as a through-hole, to fluidically isolate the gas passageway 3126 from an area outside of the housing 3110. After the proximal end 3414 of the compressed gas container 3412 has been punctured, pressurized gas flows from the compressed gas container 3412 into the gas passageway 3126 through the opening 3627 defined by the puncturing element 3620 and the channel 3640 defined by the proximal end 3632 of the cap 3630.

The inner surface 3636 of the cap 3630 is configured to hermetically seal the proximal end 3414 of the compressed gas container 3412 within the opening 3638. This arrangement prevents pressurized gas from leaking around the compressed gas container 3412 to an area outside of the housing 3110 after the proximal end 3414 of the compressed gas container 3412 has been punctured. In some embodiments, the inner surface 3636 is sized to produce an interference fit with the compressed gas container 3412. In other embodiments, the cap 3630 includes a separate sealing member, such as, for example, an o-ring, to seal the proximal end 3414 of the compressed gas container 3412 within the opening 3638.

Figure 29:
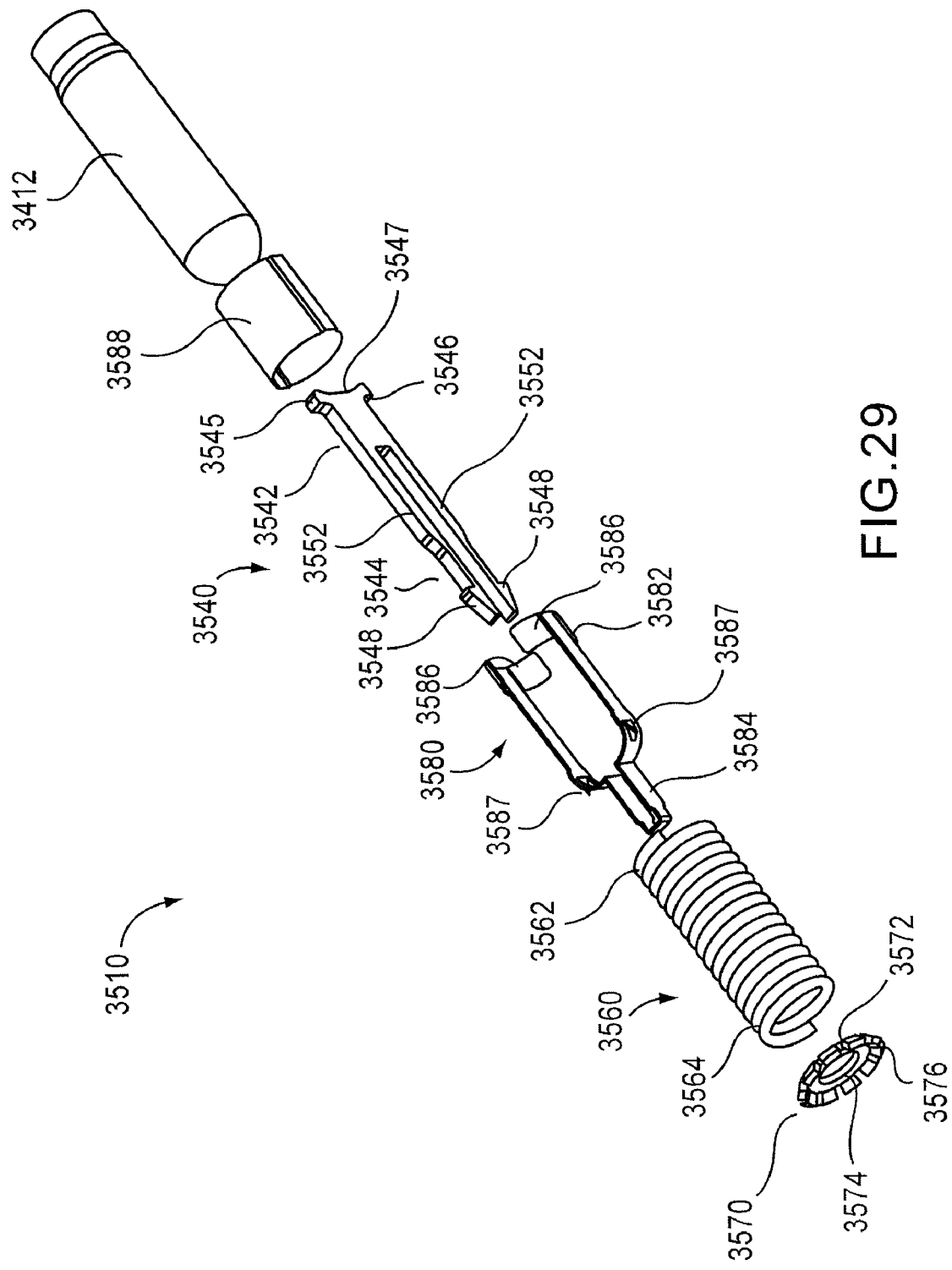
FIG. 29 is an exploded perspective view of a portion of the auto-injector shown in FIG. 21.
Figure 30:
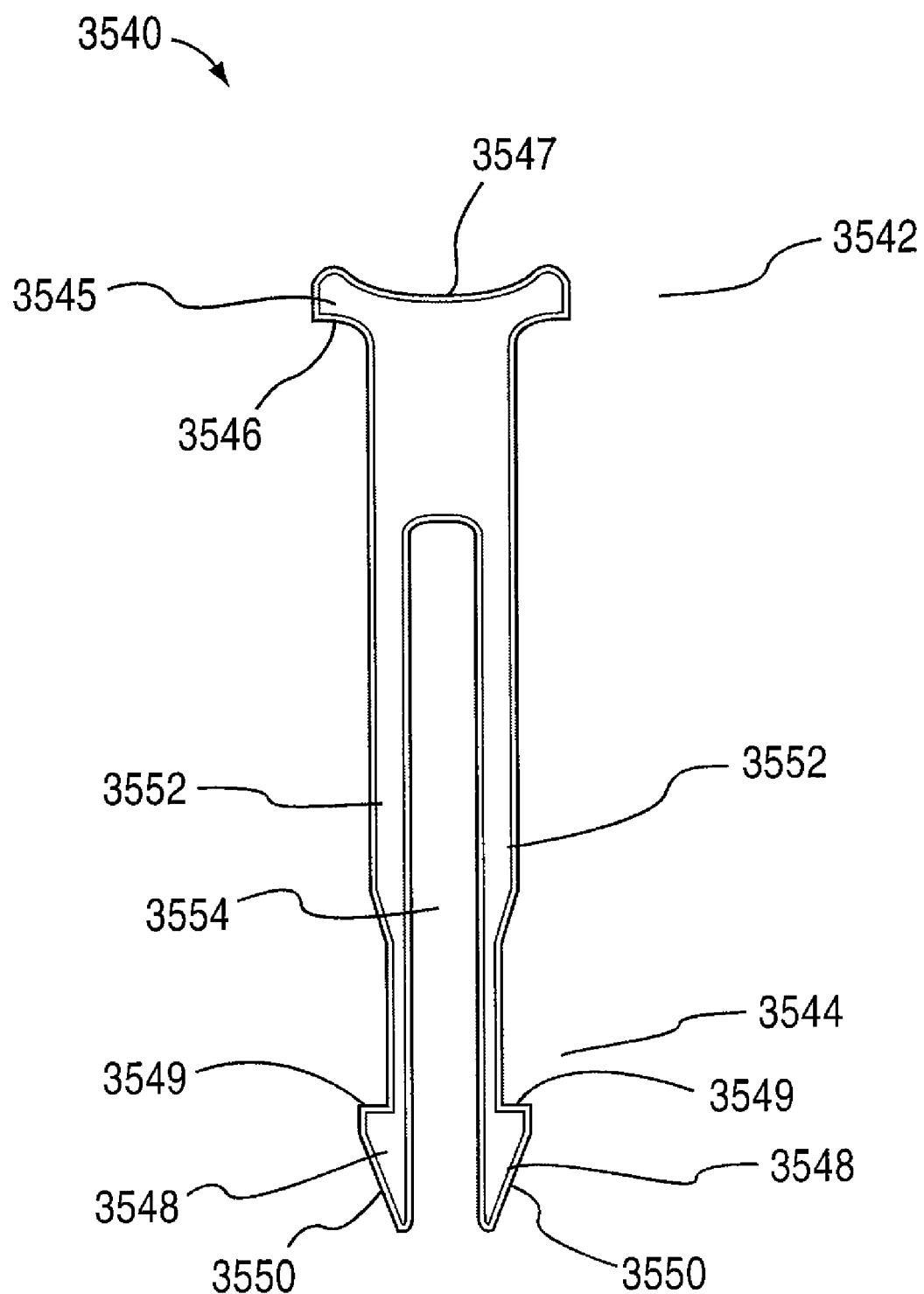
FIG. 30 is a front view of a component of the auto-injector shown in FIG. 29.

After the compressed gas container 3412 is moved into engagement with the gas release mechanism 3612, the position of the compressed gas container 3412 within the gas container opening 3124 is maintained by the locking tabs 3587 on the connector 3580. As shown in FIG. 29, each locking tab 3587 includes a pointed portion that is angled outwardly from the connector 3580. This arrangement allows the connector 3580 to move proximally within the gas container opening 3124 of the housing 3110, but prevents the connector 3580 from moving distally within the gas container opening 3124 of the housing 3110. Said another way, the arrangement of the locking tabs 3587 prevents the compressed gas container 3412 from being "kicked back" when exposed to the force produced by the pressurized gas as the pressurized gas is released.

Figure 37:
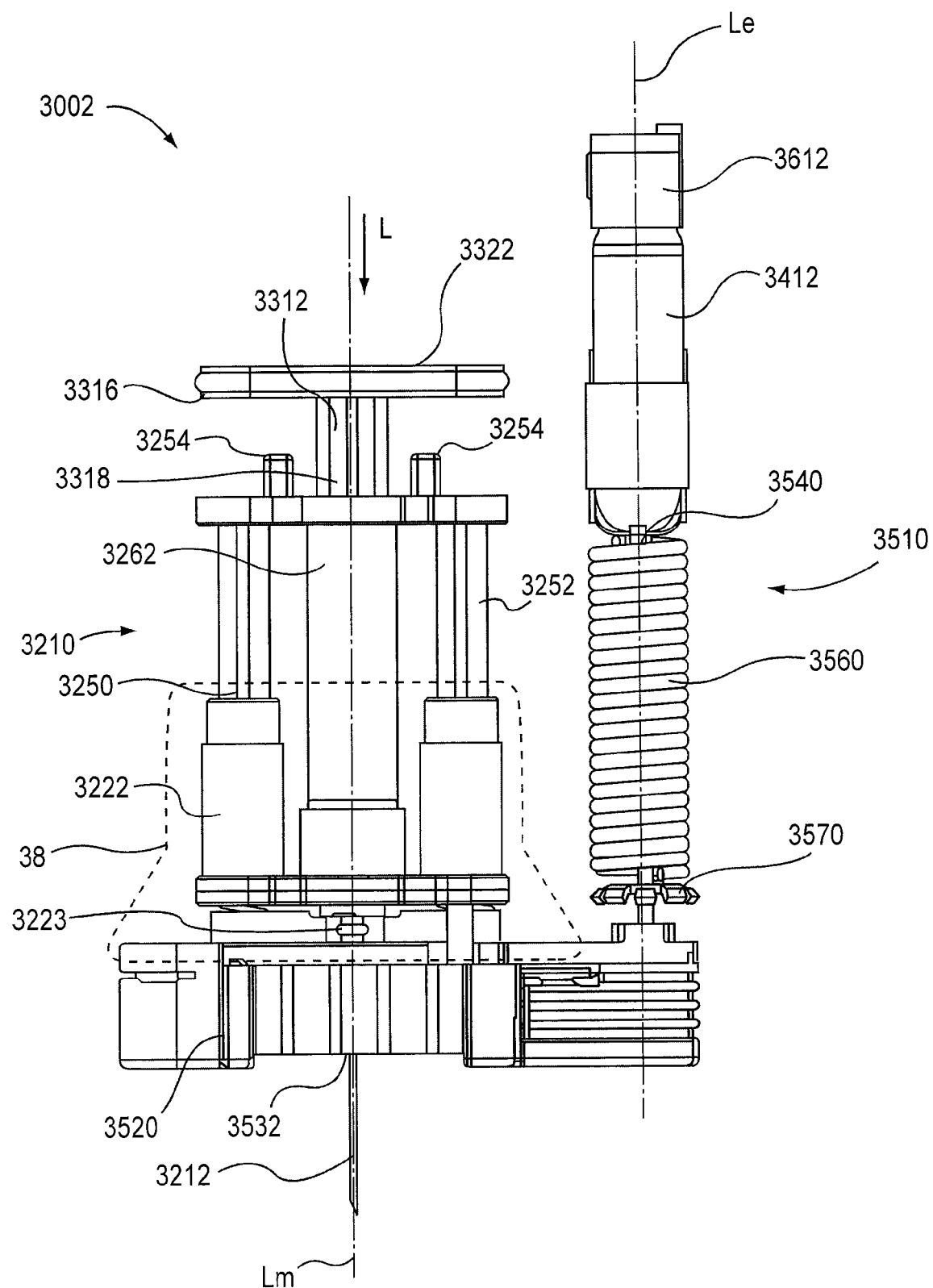
FIG. 37 is front view of the auto-injector illustrated in FIGS. 19 and 31 in a third configuration.
Figure 38:
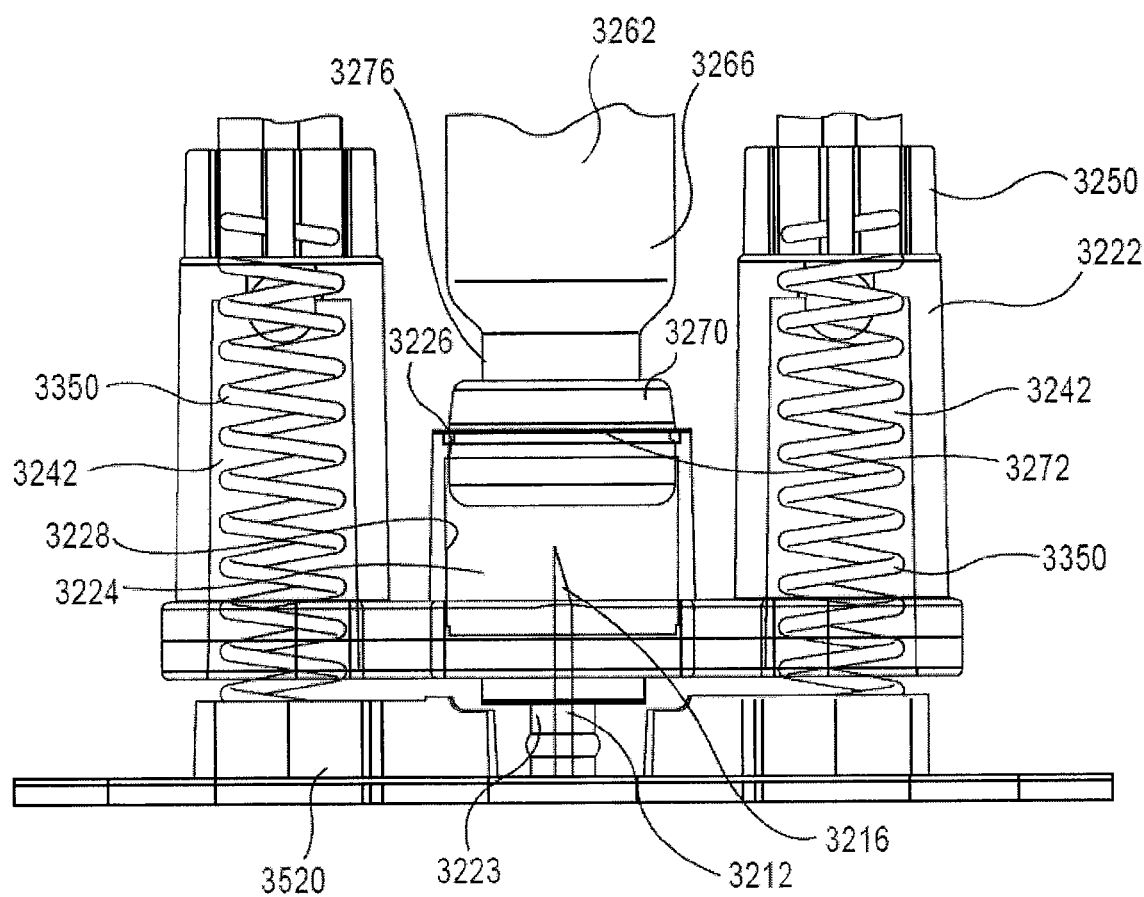
FIG. 38 is a front view of the portion of the auto-injector labeled as 38 in FIG. 37.

As previously discussed, the pressurized gas released from the compressed gas container 3412 produces a force on the boundary of the gas chamber 3120, including the surface 3322 of the movable member 3312. This force causes the movable member 3312 and the medicament injector 3210 move together distally within the housing 3110, as shown by arrow L, placing the auto-injector 3002 in a third configuration, as shown in FIG. 37. When in the third configuration, the distal end 3214 of the needle 3212 is disposed through the opening 3532 defined by the base 3520 to an area outside of the auto-injector 3002. Moreover, as shown in FIG. 38, when the auto-injector 3002 is in the third configuration, the proximal end 3216 of the needle 3212 remains spaced apart from the distal end 3266 of the medicament container 3210, ensuring that the needle 3212 remains fluidically isolated from the medicament container 3210. In this manner, the needle 3212 can be inserted into a patient as the auto-injector 3002 moves between its second configuration (FIG. 31) and its third configuration (FIG. 37) without injecting the medicament until after insertion is completed. A more detailed description of the medicament injector 3210 and the movable member 3312 is provided below with reference to FIGS. 37 through 42.

Figure 39:
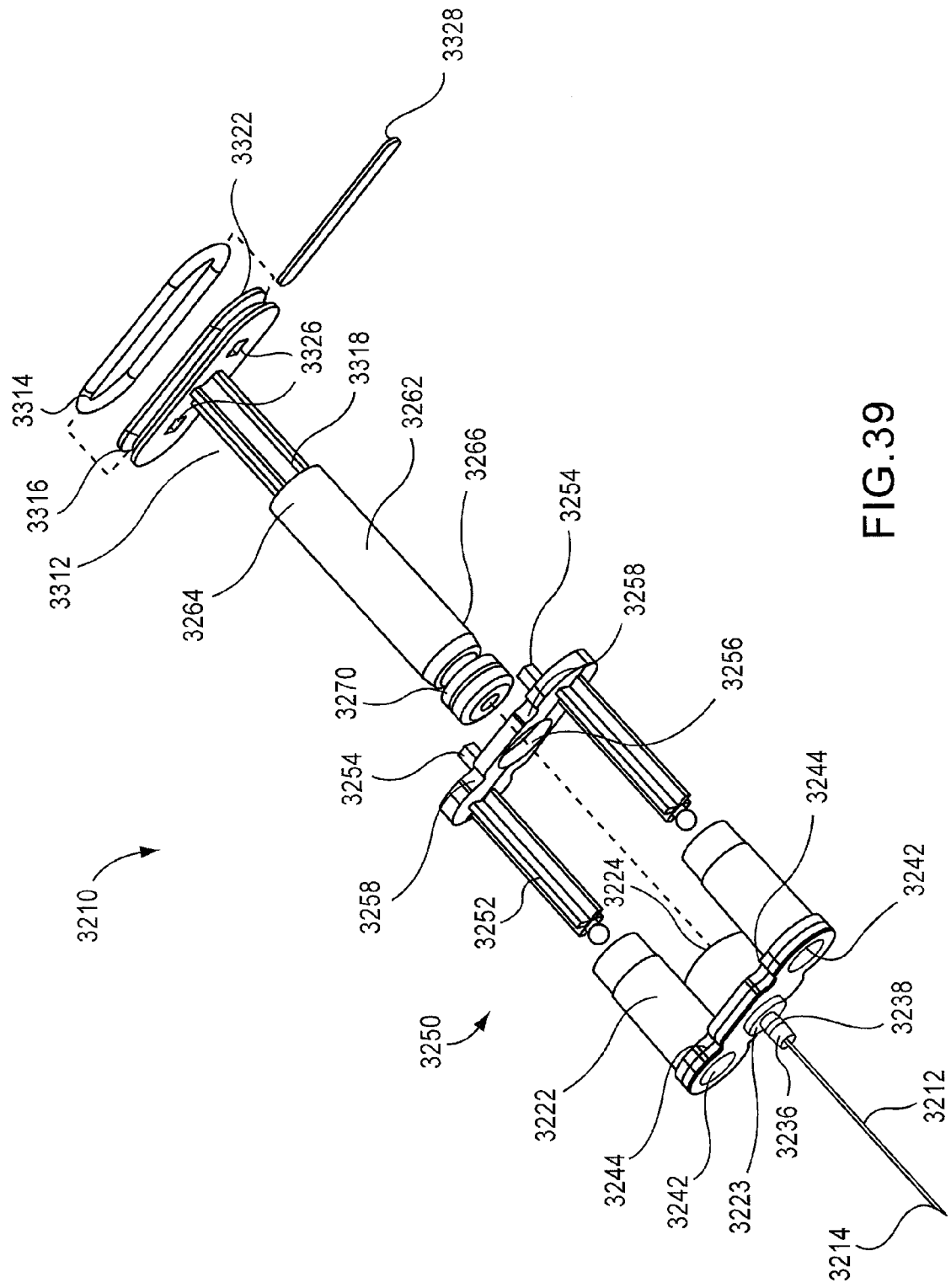
FIG. 39 is a perspective view of a portion of the auto-injector shown in FIG. 37.
Figure 40:
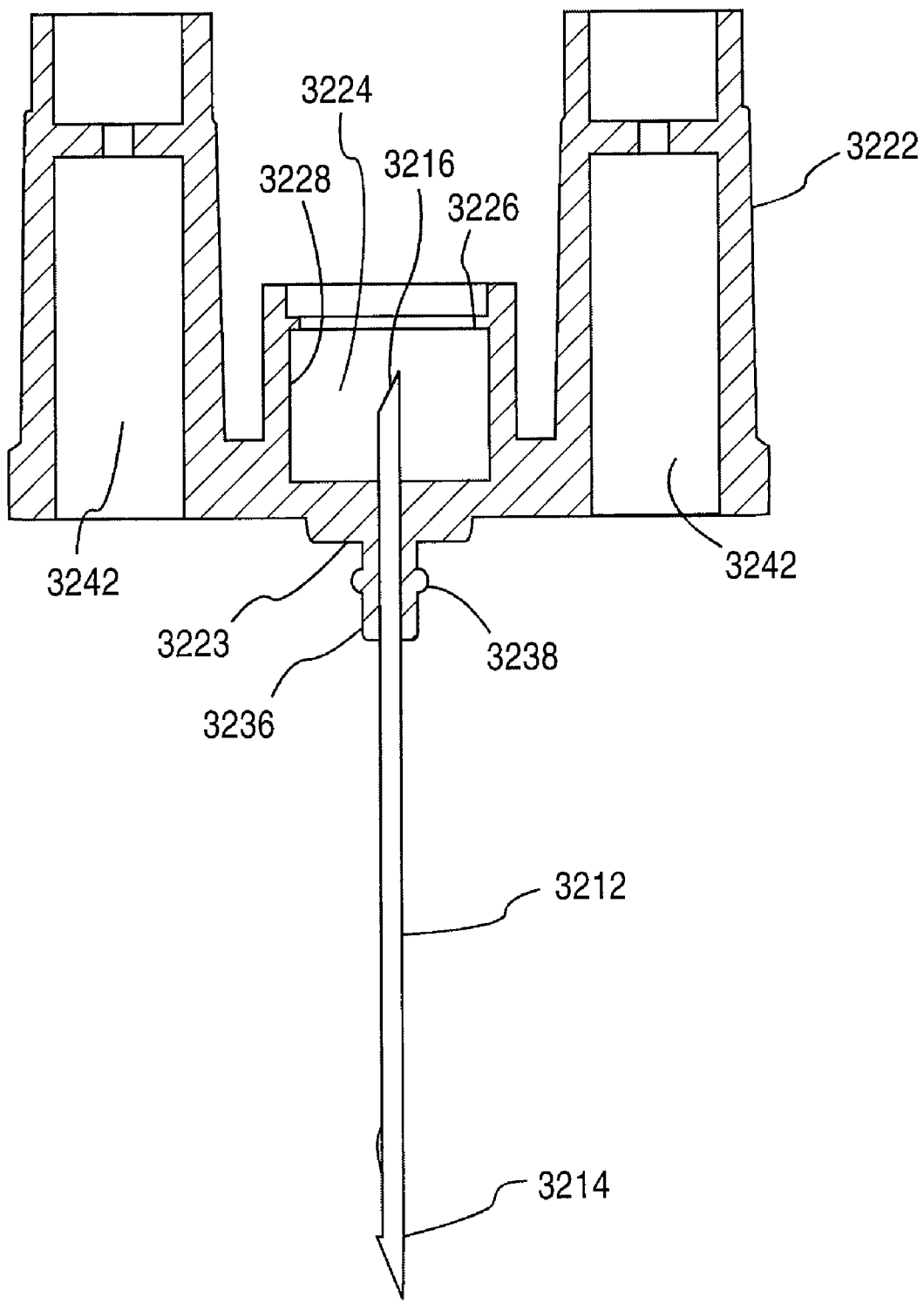
FIG. 40 is a cross-sectional view of a portion of the auto-injector as shown in FIG. 37.

As previously described, the medicament injector 3210 includes a carrier 3250, a medicament container 3262 and a needle 3212. The carrier 3250 has a lower portion 3222 and an upper portion 3252. The lower portion 3222 of the carrier 3250 includes a needle hub 3223, which contains the needle 3212. The lower portion 3222 of the carrier 3250 also defines an opening 3224 configured to receive a distal portion 3266 the medicament container 3262. As shown in FIG. 39, the needle 3212 is coupled to the needle hub 3223 such that the proximal end 3216 of the needle 3212 is disposed within the opening 3224 and the distal end 3214 of the needle 3212 extends distally outside of the needle hub 3223.

The inner surface 3228 of the lower portion 3222 defining the opening 3224 includes a protrusion 3226. The protrusion 3226 is configured to engage a corresponding recess 3272 defined by a sealing cap 3270 disposed at the distal portion 3266 of the medicament container 3262 (see FIG. 42) to secure the medicament container 3262 within the opening 3224 such that the proximal end 3216 of the needle 3212 is spaced apart from the distal end 3266 of the medicament container 3210. The protrusion 3226 and the recess 3272 are configured such that the protrusion 3226 will become disengaged from the recess 3272 when the force applied exceeds a predetermined value. Said another way, the protrusion 3226 and the recess 3272 collectively form a removable snap-fit that allows the medicament container 3262 to be moved within the opening 3224 when the force applied to the medicament container 3262 exceeds a predetermined value. This arrangement ensures that the needle 3212 remains fluidically isolated from the medicament container 3262 during the insertion operation.

Figure 23:
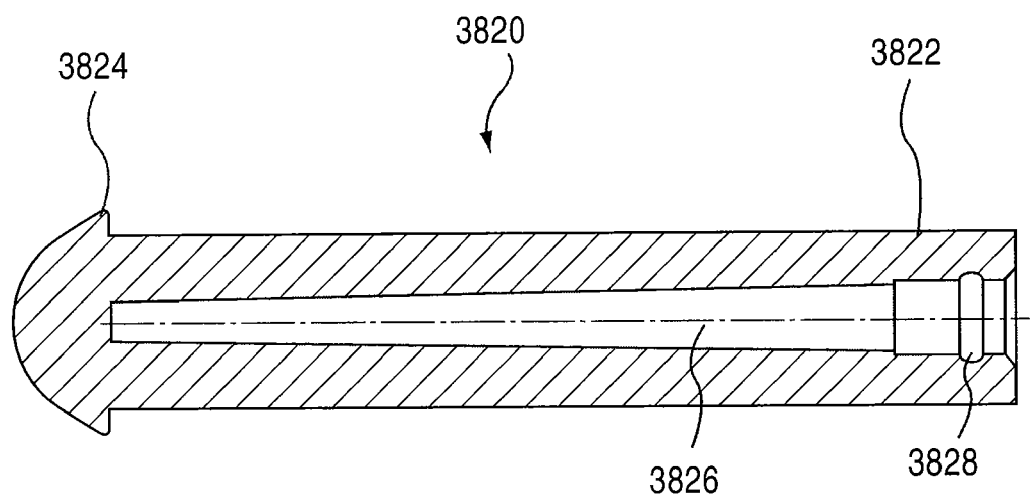
FIG. 23 is a cross-sectional view of a component illustrated in FIG. 21.
Figure 24:
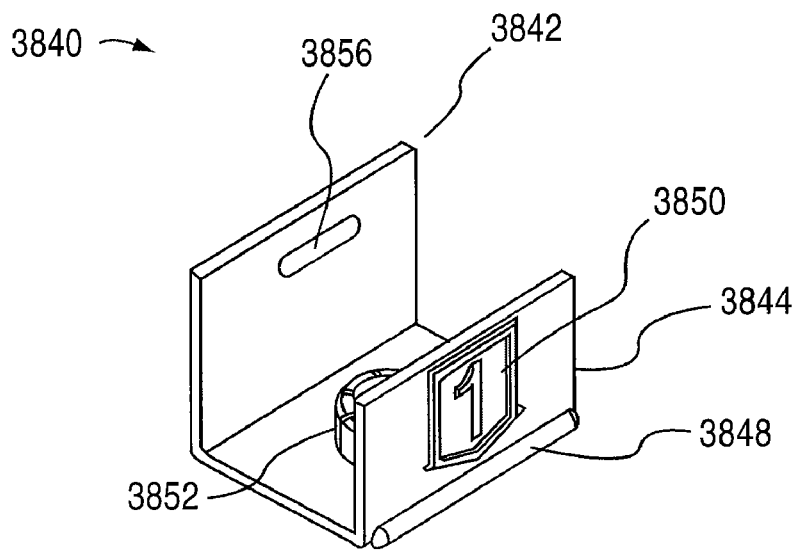
FIG. 24 is a perspective view of a component illustrated in FIG. 21.

The outer surface 3236 of the lower portion 3222 includes a protrusion 3238. As previously described, the protrusion 3238 is configured to engage a corresponding recess portion 3828 within the opening 3826 of the sheath 3820 (see FIG. 23) to removably couple the sheath 3820 to the needle hub 3223.

The lower portion 3222 of the carrier 3250 also defines two retraction spring pockets 3242 each receiving the proximal end 3352 of a retraction spring 3350. As previously discussed, the distal end 3354 of each retraction spring 3350 is retained within the retraction spring pockets 3531 defined by the base 3520. As shown in FIG. 38, when the carrier 3250 moves distally within the housing 3110, the retraction springs 3350 are compressed and therefore bias the carrier 3250 towards the proximal portion 3112 of the housing 3110.

The upper portion 3252 of the carrier 3250 defines an opening 3256 configured to receive a proximal portion 3264 of the medicament container 3262 and includes two valve actuators 3254. As described in more detail herein, the valve actuators 3254 are configured to engage a gas relief valve 3328 to allow the pressurized gas contained within the gas chamber 3120 to escape when the injection event is complete.

The upper portion 3252 of the carrier 3250 defines four gas relief passageways 3258. Similarly, the lower portion 3222 of the carrier 3250 defines four gas relief passageways 3244. When the pressurized gas is released from the gas chamber 3120, the gas relief passageways 3258, 3244 provide a fluid path to allow the pressurized gas to flow from the gas chamber 3120 to an area outside of the housing 3110.

Figure 42:
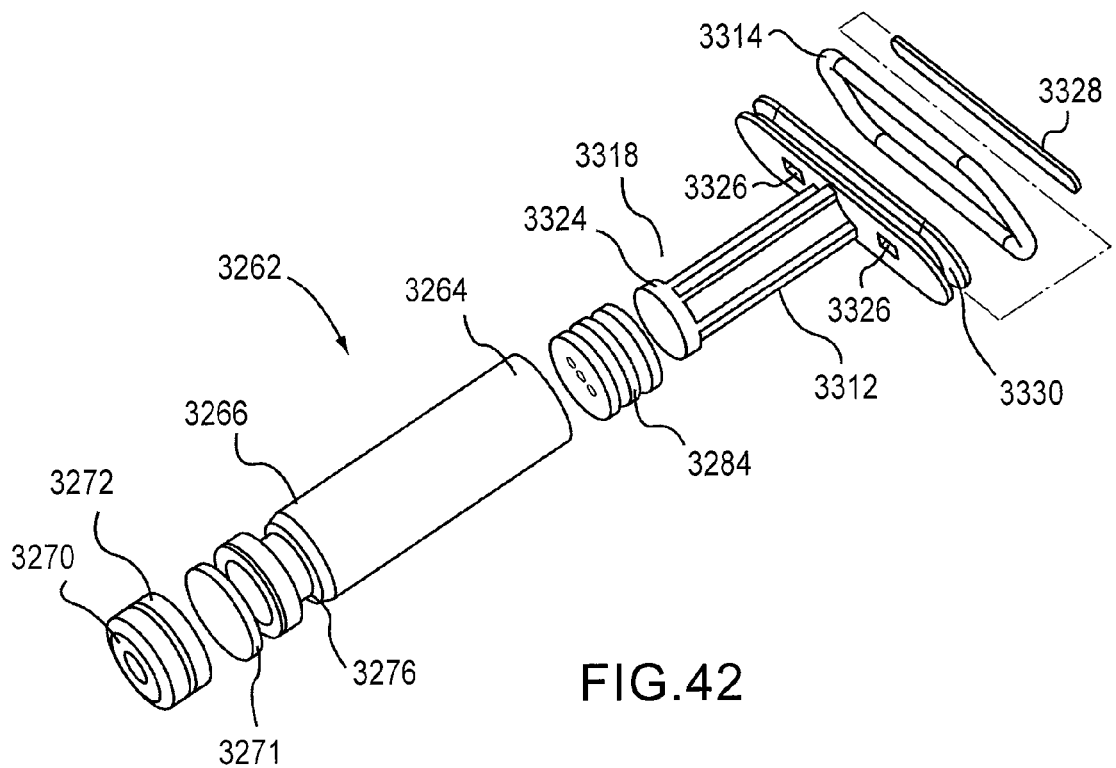
FIG. 42 is an exploded perspective view of a portion the auto-injector as shown in FIG. 37.

As described above, the movable member 3312 includes a proximal end portion 3316 and a distal end portion 3318. The distal end portion 3318 includes a piston 3324 disposed within the proximal portion 3264 of the medicament container 3262, such that the piston engages a plunger 3284 contained within the medicament container 3262, as shown in FIG. 42.

Figure 41:
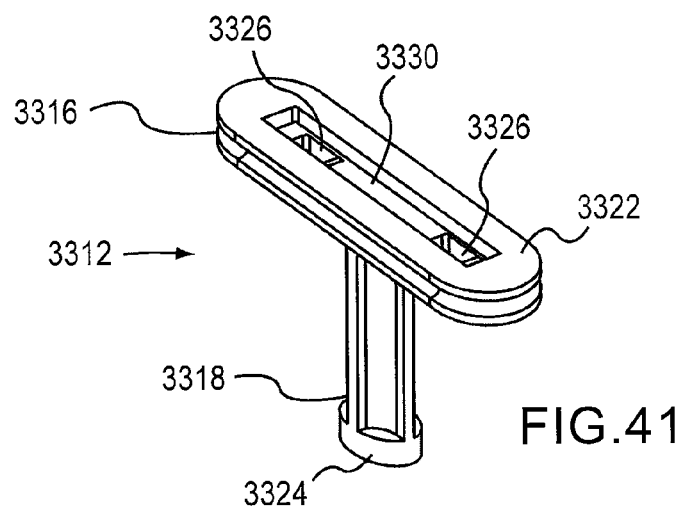
FIG. 41 is a perspective view of a portion of the auto-injector as shown in FIG. 37.

The proximal end portion 3316 includes a surface 3322 that defines a portion of a boundary of the gas chamber 3120. As shown in FIG. 41, the proximal end portion 3316 defines two openings 3326 therethrough, each of which are in fluid communication between the gas chamber 3120 and the interior of the housing 3110 outside the gas chamber 3120. The proximal end portion 3316 further defines a slot 3330 that receives a gas relief valve 3328, which can be, for example, a flexible rubber member. The gas relief valve 3328 is positioned within the slot 3330 and adjacent the openings 3326 to selectively allow fluid communication between the gas chamber 3120 and the area outside the gas chamber 3120 through the openings 3326. The operation of the gas relief valve 3328 is discussed in more detail herein.

The proximal end portion 3316 of the movable member 3312 also includes a seal 3314 that engages a portion the inner surface 3122 of the housing 3110 (see FIG. 36) to fluidically isolate the gas chamber 3120. Although the seal 3314 is shown as being an o-ring seal, in some embodiments, the seal need not be a separate component, but can rather be a portion of the proximal end portion 3316 of the movable member 3312.

Figure 43:
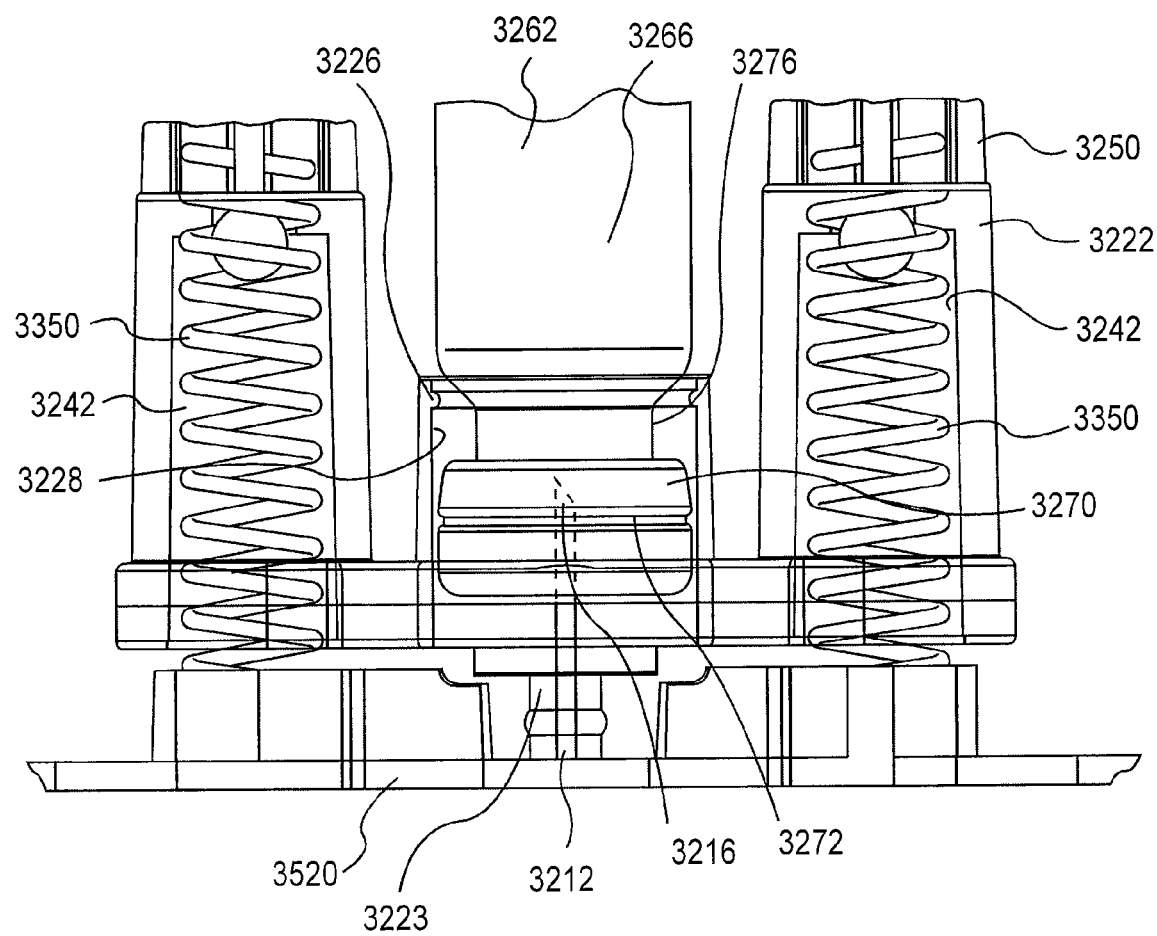
FIG. 43 is front view of the auto-injector illustrated in FIGS. 19, 31 and 38 in a fourth configuration.

When the needle insertion operation is completed, the lower portion 3222 of the carrier 3250 engages the base 3520, preventing further distal movement of the carrier 3250 within the housing. Because the distal motion of the carrier 3250 is opposed, the force exerted by the pressurized gas on the surface 3322 of the movable member 3312 increases until the protrusion 3226 of the lower portion 3222 of the carrier 3250 and the recess 3272 defined by sealing cap 3270 of the medicament container 3262 become disengaged. Accordingly, the medicament container 3262 to moves distally relative to the carrier 3250, placing the auto-injector 3002 in a fourth configuration, as shown in FIG. 43. When moving between the third configuration (FIG. 38) and the fourth configuration (FIG. 43), the proximal end 3216 of the needle 3212 pierces the sealing cap 3270 and the liner 3271 disposed at the distal portion 3266 of the medicament container 3262. As such, when in the fourth configuration, the proximal end 3216 of the needle 3212 is in fluid communication with the medicament container 3262, thereby allowing the medicament to be injected.

Figure 44:
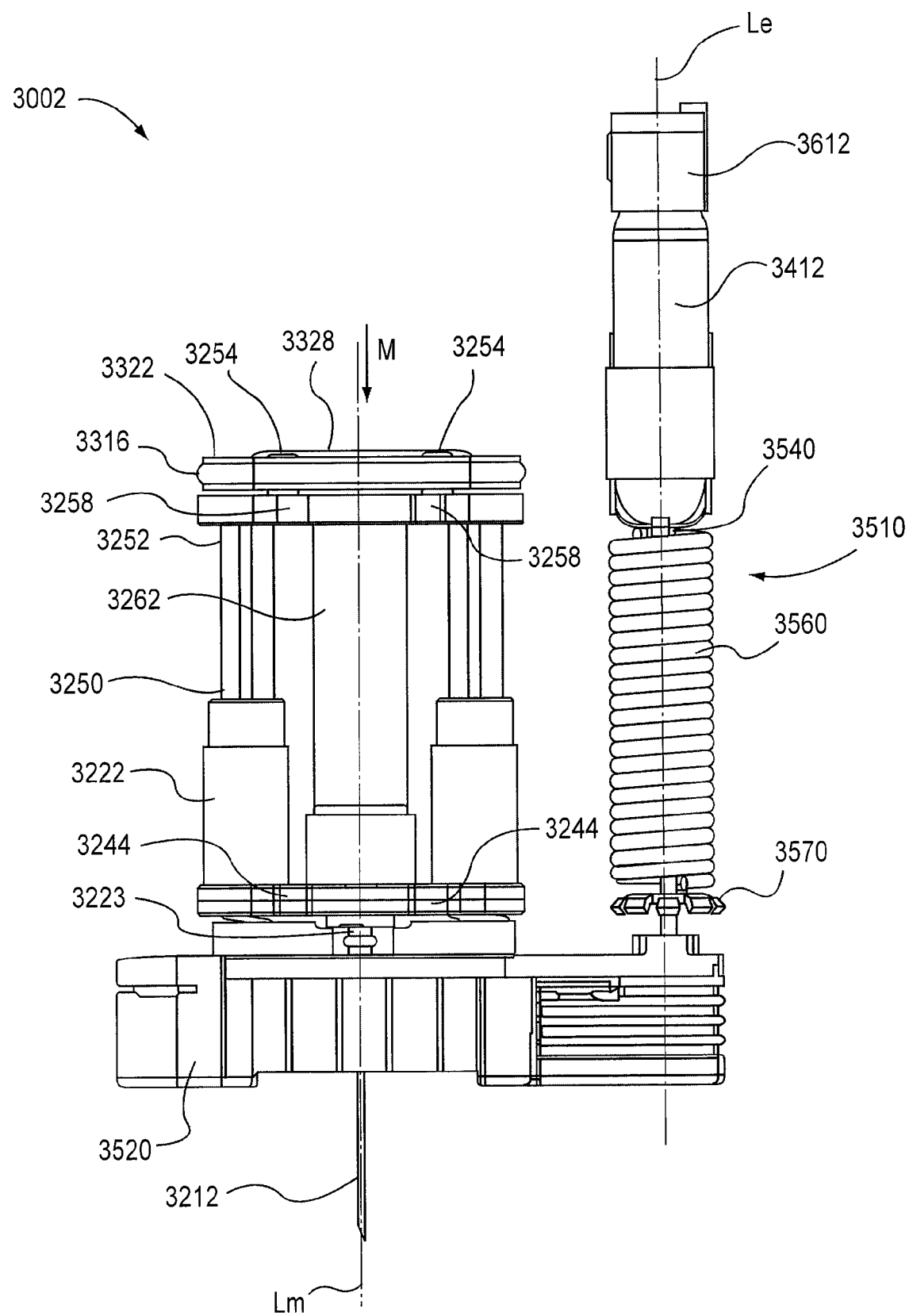
FIG. 44 is a front view of a portion of the auto-injector illustrated in FIGS. 19, 31, 38 and 43 in a fifth configuration.

Once the needle 3212 is in fluid communication with the medicament container 3262, the force from the pressurized gas causes the piston 3324 of the movable member 3312 to move the plunger 3284 within the medicament container 3262, as shown by arrow M, thereby expelling the medicament through the needle 3212. The piston 3324 and the plunger 3284 move a predetermined distance within the medicament container 3262, placing the auto-injector 3002 in a fifth configuration, as shown in FIG. 44. When the auto-injector 3002 is in the fifth configuration, the injection of medicament is complete.

When the auto-injector 3002 is in its fifth configuration, proximal portion 3316 of the movable member 3312 is in contact with the upper portion 3252 of the carrier 3250, thereby preventing further movement of the piston 3324 within the medicament container 3262. In this manner, the distance through which the piston 3324 travels, and therefore the amount of medicament injected, can be controlled.

Additionally, when the auto-injector 3002 is in its fifth configuration, the valve actuators 3254 are disposed within the openings 3326 such that the valve actuators 3254 displace the gas relief valve 3328. Accordingly, the pressurized gas contained within the gas chamber 3120 can flow from the gas chamber 3120 to the area within the housing 3310 outside of the gas chamber 3310. As previously discussed, the gas relief passageways 3258, 3244 provide a fluid path to allow the pressurized gas to flow from the gas chamber 3120, through the opening 3532 defined by the base 3520 and to an area outside of the housing 3110.

Figure 45:
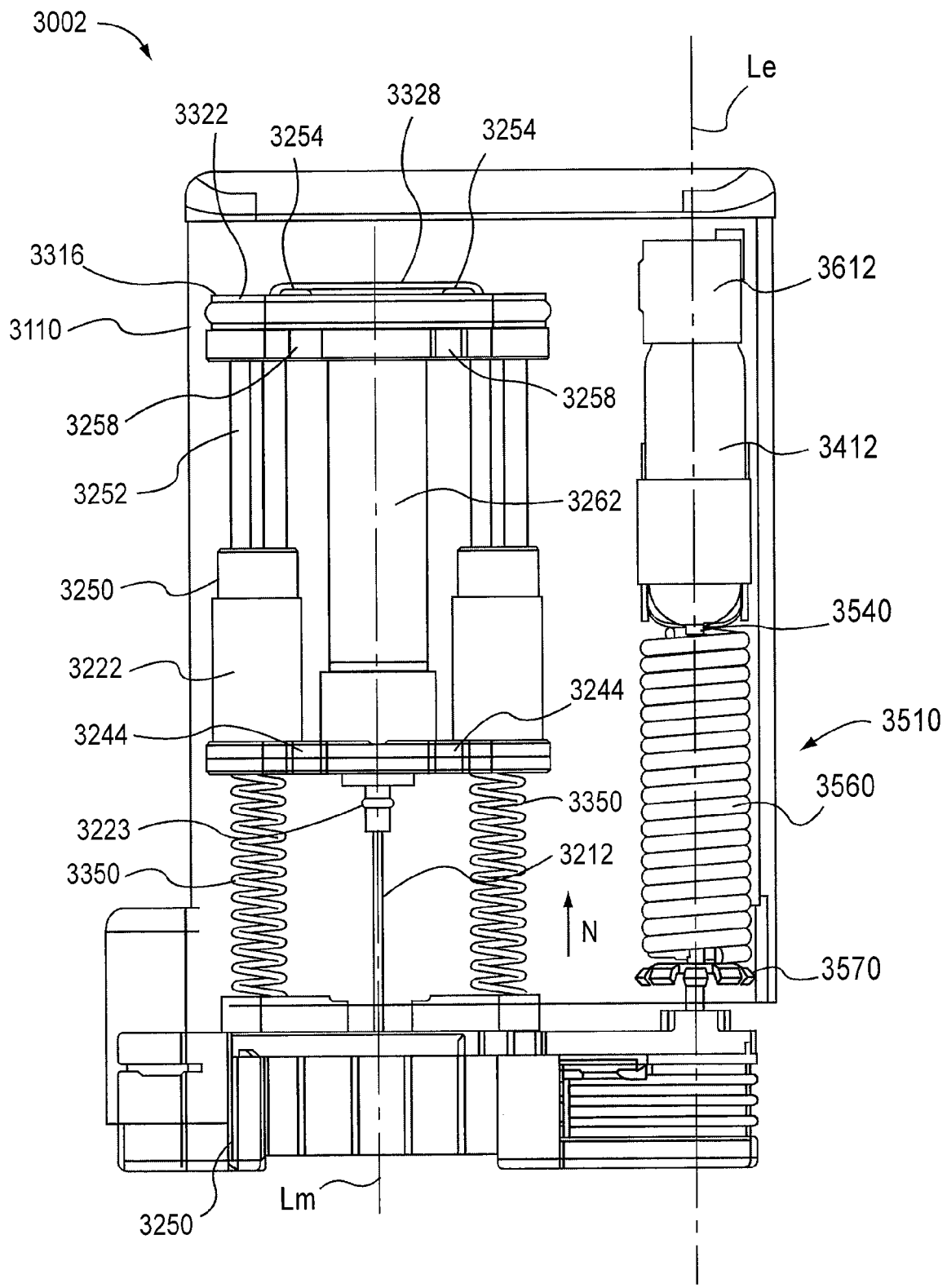
FIG. 45 is a front view of the auto-injector illustrated in FIGS. 19, 31, 38, 43 and 44 in a sixth configuration.

When the pressurized gas flows out of the gas chamber 3120, the pressure exerted on the surface 3322 of the movable member 3312 decreases. Accordingly, the force exerted by the retraction springs 3350 is sufficient to move the medicament injector 3210 and the movable member 3312 proximally within the housing 3110, as shown by arrow N, into a sixth (or retracted) configuration as shown in FIG. 45. Because the medicament injector 3210 and the movable member 3312 move together, the valve actuators 3254 remain disposed within the openings 3326 as the auto-injector 3002 moves into the sixth configuration. In this manner, the gas relief valve 3328 remains displaced and the openings 3326 remain in fluid communication with the gas chamber 3120 and the area within the housing 3310 outside of the gas chamber 3310 independent of the position of the movable member 3312. Such an arrangement ensures that all of the pressurized gas flows out of the gas chamber 3120, thereby ensuring that the medicament injector 3210 and the movable member 3312 return to the sixth configuration and do not oscillate between the sixth configuration and the fifth configuration, which could lead to the needle 3212 not being fully retracted into the housing 3110.

Although the auto-injector 3002 has been shown and described having a housing 3110 having a substantially rectangular shape, in some embodiments, an auto-injector can have a housing having any shape. In some embodiments, for example, an auto-injector can have a substantially cylindrical shape. In other embodiments, for example, the auto-injector can have an irregular and/or asymmetrical shape.

Figure 46:
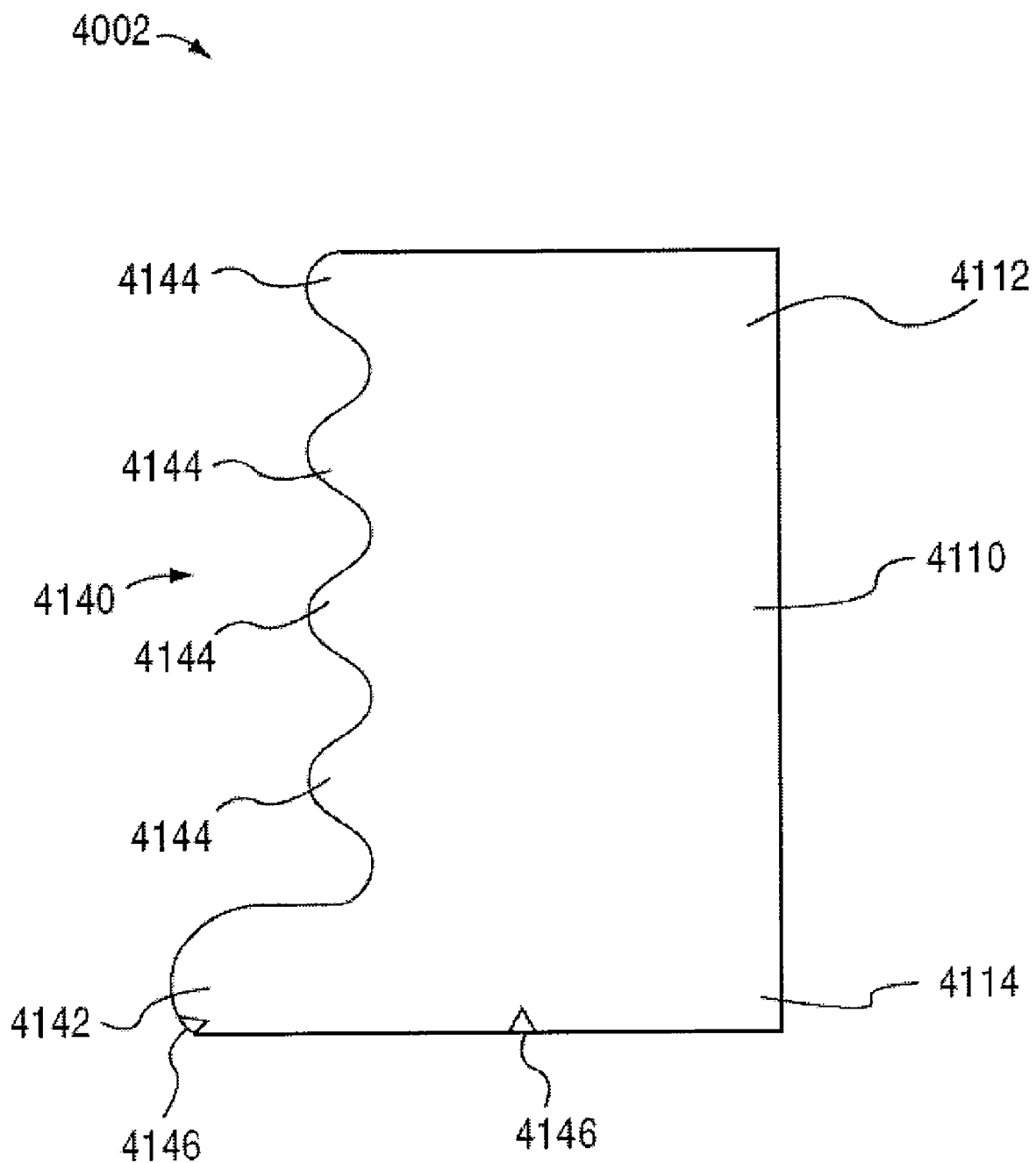
FIG. 46 is a front view of an auto-injector according to an embodiment of the invention.

Although the auto-injector 3002 has been shown and described as including a protrusion 3142 disposed at the distal end portion 3114 of the housing 3110 to help a user grasp and retain the housing 3110, in some embodiments, a protrusion can be disposed anywhere along the housing. In other embodiments, a protrusion can symmetrically surround the distal portion of the housing. In yet other embodiments, the housing of an auto-injector can include a gripping portion configured to help a user grasp and retain the housing. The gripping portion can include, for example, a textured surface, a contoured surface, a surface having an adhesive that forms a tacky surface to adhere to the user's hand or the like. For example, FIG. 46 shows an auto-injector 4002 according to an embodiment of the invention having a housing 4110. The housing 4110 includes a proximal end portion 4112, a distal end portion 4114 and a gripping portion 4140. The distal end portion 4114 of the housing 4110 includes a protrusion 4142 to prevent the user's hand from slipping off of the distal end portion 4114 of the housing 4110 when using the auto-injector 4002. Similarly, the gripping portion 4140 includes a series of contours 4144 that engage the user's fingers to help the user grasp and retain the housing 4110 when the auto-injector 4002 is in use.

The distal end portion 4114 of the housing 4110 also includes two alignment marks 4146 to guide the user when placing the auto-injector 4002 against the body. Although the alignment marks 4146 are shown as markings on the housing 4110, in other embodiments, the alignment marks can include protrusions, openings or the like.

Certain components of the auto-injector 3002 are shown and described as being coupled together via protrusions and mating recesses. The protrusions and/or recesses can be disposed on any of the components to be coupled together and need not be limited to only a certain component. For example, the base 3520 is shown as defining two openings 3536 that receive corresponding attachment protrusions 3150 on the distal end portion 3114 of the housing 3110. In some embodiments, however, the protrusions can be disposed on the base and the mating recesses can be defined by the distal end portion of the housing. In other embodiments, two or more components can be coupled together in any suitable way, which need not include protrusions and mating recesses. For example, in some embodiments, two or more components can be coupled together via mating shoulders, clips, adhesive and the like.

Similarly, although certain components of the auto-injector 3002 are shown and described as being constructed from multiple separate components, in some embodiments, such components can be monolithically constructed. For example, the carrier 3250 is shown and described as including an upper portion 3252 and a lower portion 3222 that are constructed separately and then coupled together. In other embodiments, a carrier can be constructed monolithically.

Although the base 3520 of the auto-injector 3002 has been shown and described covering almost the entire distal end portion 3114 of the housing 3110, in some embodiments, a base configured to actuate the auto-injector can be disposed about only a portion of the distal end of the housing. For example, in some embodiments, an auto-injector can include a button extending from the distal end portion of the housing configured to engage and release the system actuator.

Although the rod 3540 is shown and described as being an elongated member that is released by being elastically deformed, in some embodiments, a rod can be of any suitable shape and in any suitable orientation within the housing. Moreover, in some embodiments, a rod can be released by being plastically deformed. For example, in some embodiments, a rod can be disposed along an axis that is offset from the longitudinal axis of the energy storage member. In some embodiments, the rod can be configured to break upon actuation.

Although the gas release mechanism 3612 is shown and described as including a puncturing element 3620 to puncture a portion of the compressed gas container 3262, the gas release mechanism 3612 need not include a puncturing element 3620. For example, in some embodiments, the gas release mechanism can include an actuator configured to actuate a valve that controls the flow of gas out of the compressed gas container. For example, in some embodiments, a compressed gas container can include a spring loaded check ball and the gas release mechanism can include an actuator configured to engage and depress the check ball to release pressurized gas from the compressed gas container.

Although the distance through which the piston 3324 travels, and therefore the amount of medicament injected, is shown and described as being controlled by configuring the movable member 3312 such that it is in contact with the upper portion 3252 of the carrier 3250 when the auto-injector 3002 is in its fifth configuration, in other embodiments, any suitable method of controlling the piston travel can be employed. For example, in some embodiments, piston travel can be limited by including a protrusion within the medicament container, such as a necked portion, that limits the motion of the piston within the medicament container. In other embodiments, the housing can include a protrusion to limit the motion of the movable member. In yet other embodiments, the valve actuator can be configured to actuate the gas relief valve when the piston has moved a predetermined distance within the medicament container. In yet other embodiments, a combination of each of the above methods for controlling the piston travel can be employed.

Although the auto-injector 3002 is shown and described as having six different configurations that are different from each other, in some embodiments, certain configuration of an auto-injector can be the same as another configuration. For example, in some embodiments, a "pre-actuation configuration" can be the same as a "retracted" configuration. In other embodiments, any of the functions described above can be accomplished when an auto-injector is moved between any number of different configurations.

Although the auto-injector 3002 is shown and described as including a compressed gas cylinder 3412, in other embodiments an auto-injector can include any suitable energy storage member. For example, in some embodiments, an auto-injector can include a mechanical energy storage member, such as a spring, an electrical energy storage member, such as a battery or a capacitor, a chemical energy storage member, such as a container containing two substances that can react to produce energy, a magnetic energy storage member or the like. Similarly, although the auto-injector 3002 is shown and described as including a gas release mechanism 3612, in other embodiments an auto-injector can include any suitable energy release mechanism. Such energy release mechanism can include, for example, an electrical circuit, a mechanical spring retainer, a fluid control valve or the like.

Figure 47:
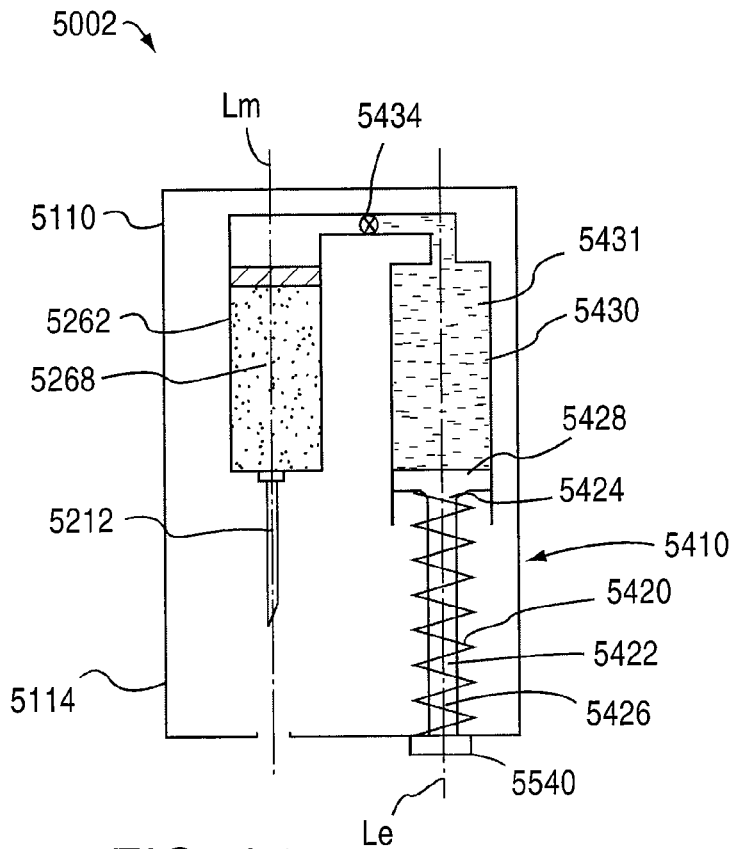
FIG. 47 is a schematic illustration of an auto-injector according to an embodiment of the invention.

For example, FIG. 47 shows a schematic illustration of an auto-injector 5002 that includes a mechanical energy storage member 5410. The auto-injector 5002 includes a housing 5110 that contains a medicament container 5262, an energy storage member 5410, a release member 5540. The medicament container 5262 is movably disposed within the housing 5110 and includes a needle 5212 through which a medicament 5268 can be injected. As illustrated, the medicament container 5262 can be moved along its longitudinal axis Lm between a first position (FIG. 47) and a second position (not shown), in which the needle 5212 extends from the housing 5110.

The energy storage member 5410 includes a spring 5420 that is disposed about a rod 5422. The rod 5422 has a proximal end 5424 and a distal end 5426. The proximal end 5424 of the rod 5422 includes a plunger 5428 that retains the spring 5420 such that the spring 5420 can be compressed when the auto-injector 5002 is in a first configuration. The plunger is also disposed within a working fluid chamber 5430. The working fluid chamber 5430 can be, for example, a hydraulic cylinder filled with a hydraulic fluid. The distal end 5426 of the rod 5422 engages the release member 5540, as discussed below.

In use, the spring 5420 can be moved within the housing 5110 along its longitudinal axis Le between a first position and a second position. When the spring 5420 moves between its first position to its second position, the plunger 5428 moves proximally within the working fluid chamber 5430, causing the working fluid 5431 to be forced through a valve 5434 and into contact with the medicament container 5262. Through the kinetic energy produced by the spring 5420, the working fluid 5431 produces a force that acts upon the medicament container 5262 to move the medicament container 5262 between its first position and its second position.

The arrangement of a mechanical energy storage member, such as a spring, and a fluidic circuit allows the direction and/or magnitude of the force produced by the energy storage member to be changed. In this manner, as shown in FIG. 47, the longitudinal axis Le of the energy storage member can be offset from the longitudinal axis Lm of the medicament container 5262, thereby allowing the medicament container 5262 and the energy storage member 5410 to be arranged within the housing 5110 in any number of different configurations.

The release member 5540 is disposed adjacent a distal end portion 5114 of the housing 5110 and is configured to selectively deploy the spring 5420 from its first position to its second position. The release member 5540 can be any suitable mechanism of the types described above for moving the spring 5420. In this manner, a user can actuate the auto-injector by manipulating the distal end portion 5114 of the housing 5110.

Figure 48:
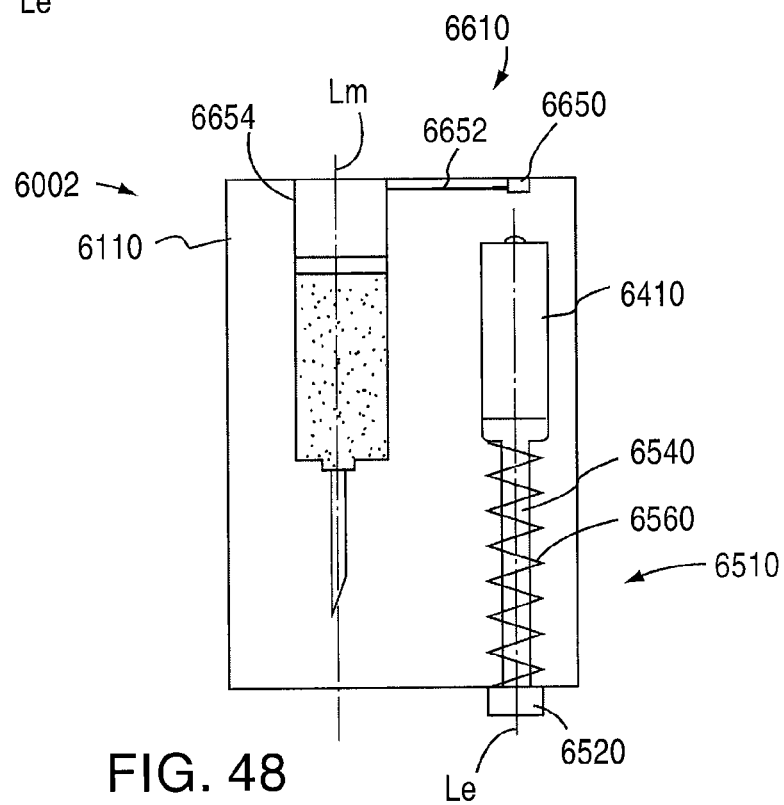
FIG. 48 is a schematic illustration of an auto-injector according to an embodiment of the invention.

FIG. 48 shows a schematic illustration of an auto-injector 6002 that includes an electrical energy storage member 6410, such as, for example a battery. The auto-injector 6002 includes a housing 6110 that contains a medicament container 6262, an energy storage member 6410, a system actuator 6510 and an energy release mechanism 6610. The medicament container 6262 is movably disposed within the housing 6110 and includes a needle 6212 through which a medicament 6268 can be injected. As illustrated, the medicament container 6262 can be moved along its longitudinal axis Lm between a first position (FIG. 48) and a second position (not shown), in which the needle 6212 extends from the housing 6110.

The energy storage member 6410 is also movably disposed within the housing 6110 along its longitudinal axis Le, which is offset from the longitudinal axis Lm of the medicament container 6262. When the energy storage member 6410 is in its first position (FIG. 48), it is spaced apart from the electrical contact 6650 of the energy release mechanism 6610. When the energy storage member 6410 is in its second position, it is in contact with the electrical contact 6650, thereby allowing current to flow from the energy storage member 6410 to an actuator 6654 via a circuit 6652. The actuator 6654 converts the electrical energy into a force that acts upon the medicament container 6262 to move the medicament container 6262 between its first position and its second position.

The system actuator 6510 includes a release member 6540 coupled to the energy storage member 6410, a spring 6560 and an actuator button 6520. The spring 6560 is disposed about the release member 6540 in a compressed configuration. The release member 6540 is removably coupled to the actuator button 6520, which is disposed at the distal end of the housing 6110. When the actuator button 6520 is manipulated, the release member 6540 is de-coupled from the actuator button 6520, thereby allowing the force from the spring 6560 to move the release member 6540. In this manner, the energy storage member 6410 is moved proximally within the housing 6110 into its second configuration. In some embodiments, the components included in the system actuator 6510 can be electrically coupled to the energy storage member 6410.

Figure 49:
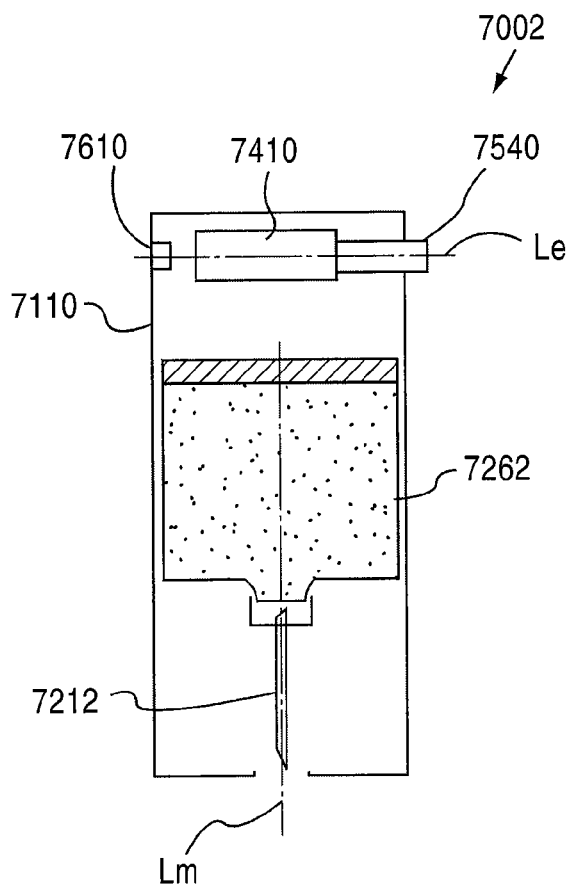
FIGS. 49 and 50 are schematic illustrations of an auto-injector according to an embodiment of the invention in a first configuration and a second configuration, respectively.
Figure 50:
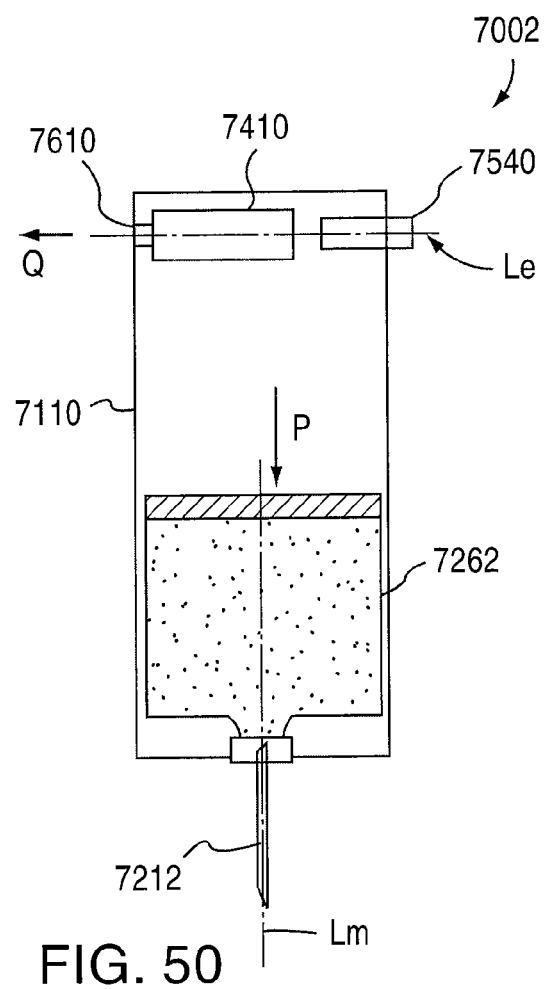

Although the auto-injectors shown and described include a medicament container and an energy storage member that are substantially parallel, in some embodiments, the medicament container and the energy storage member can be angularly offset from each other. For example, FIGS. 49 and 50 are schematic illustrations of an auto-injector 7002 in a first configuration and a second configuration, respectively. Similar to the auto-injectors described above, the auto-injector 7002 includes a housing 7110 that contains a medicament container 7262, an energy storage member 7410, a release member 7540 and an energy release mechanism 7610. The medicament container 7262, which includes a needle 7212, is disposed within the housing such that it can be moved along its longitudinal axis Lm as indicated by arrow P between a first position (FIG. 49) and a second position (FIG. 50).

The energy storage member 7410 is also movably disposed within the housing 7110 along its longitudinal axis Le, as shown by arrow Q. As shown, the longitudinal axis Le is substantially perpendicular to the longitudinal axis Lm of the medicament container 7262. When the energy storage member 7410 is in its first position (FIG. 49), it is spaced apart from the energy release mechanism 7610. When the energy storage member 7410 is in its second position (FIG. 50), it is in contact with the energy release mechanism 7610, thereby releasing energy to produce a force on the medicament container 7262 in a manner as described above.

As described above, the release member 7540 can be any suitable mechanism configured to selectively deploy the energy storage member 7410 from its first position to its second position.

Figure 51:
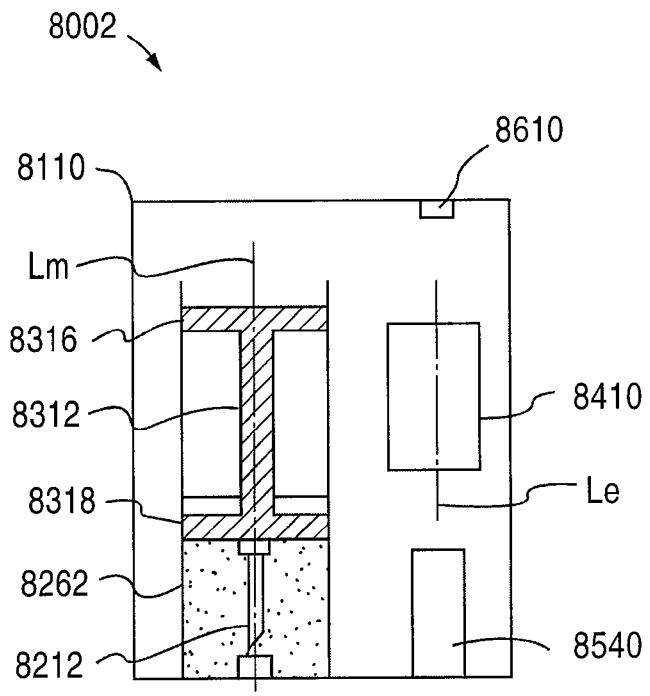
FIGS. 51 and 52 are schematic illustrations of an auto-injector according to an embodiment of the invention in a first configuration and a second configuration, respectively.
Figure 52:
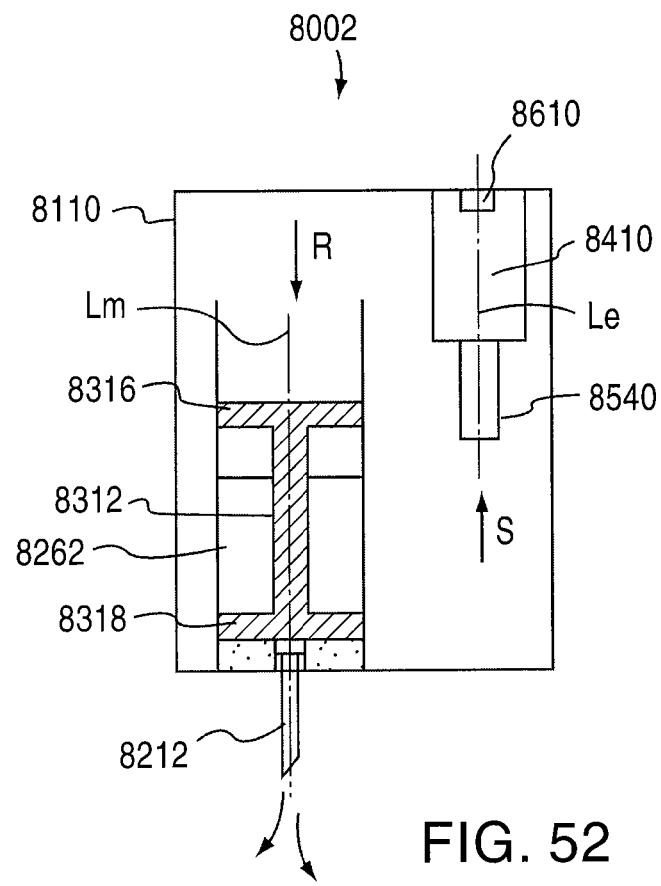

Although the auto-injectors shown and described above include a medicament container configured to move within the housing, in some embodiments, an auto-injector can be configured to move a needle within a stationary medicament container. For example, FIGS. 51 and 52 are schematic illustrations of an auto-injector 8002 in a first configuration and a second configuration, respectively. The auto-injector 8002 includes a housing 8110 that contains a medicament container 8262, a movable member 8312, an energy storage member 8410, an energy release mechanism 8610 and a release member 8540. The medicament container 8262 is fixedly disposed within the housing and defines a longitudinal axis Lm.

The movable member 8312 includes a proximal end 8316 and a distal end 8318. The distal end 8318 of the movable member 8312 is disposed within and movable within the medicament container 8262 along the longitudinal axis Lm, as shown by the arrow R. A needle 8212 is coupled to the distal end 8318 of the movable member 8312.

The energy storage member 8410 is also movably disposed within the housing 8110 along its longitudinal axis Le, as shown by arrow S. As shown, the longitudinal axis Le is offset from the longitudinal axis Lm of the medicament container 8262. When the energy storage member 8410 is in its first position (FIG. 51), it is spaced apart from the energy release mechanism 8610. When the energy storage member 8410 is in its second position (FIG. 52), it is in contact with the energy release mechanism 8610, thereby producing a force on the proximal end 8316 of the movable member 8312. The force causes the movable member 8312 to be moved within the medicament container 8262. In this manner, the needle 8212 is extended through the housing 8110 as the medicament is being injected.

As described above, the release member 8540 can be any suitable mechanism configured to selectively deploy the energy storage member 8410 from its first position to its second position.

Figure 53:
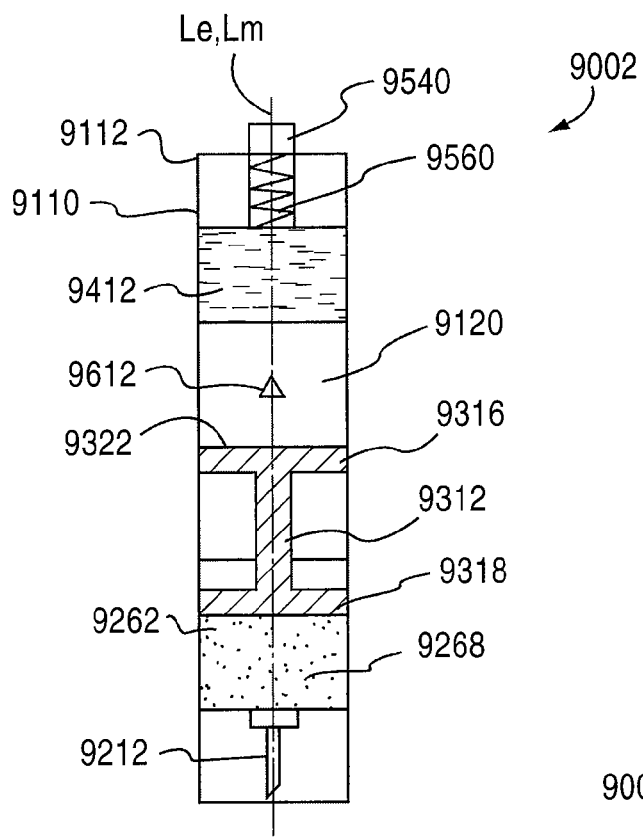
FIGS. 53-55 are schematic illustrations of an auto-injector according to an embodiment of the invention in a first configuration, a second configuration and a third configuration, respectively.
Figure 54:
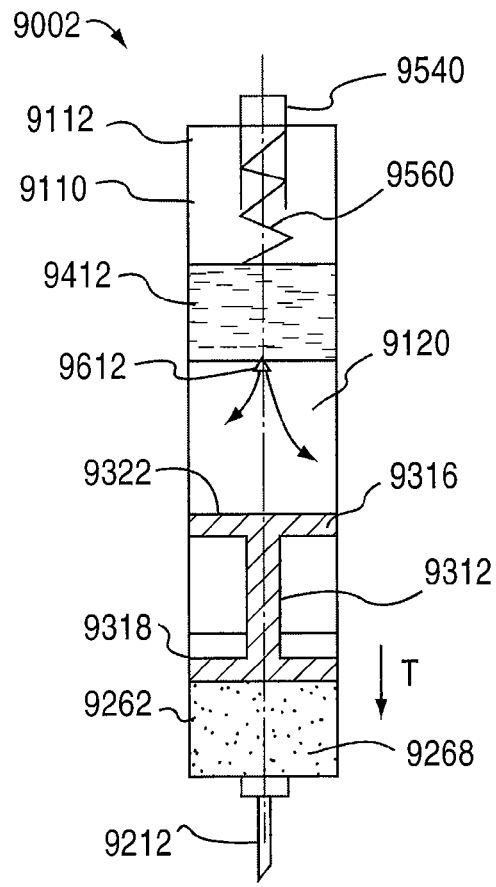
Figure 55:
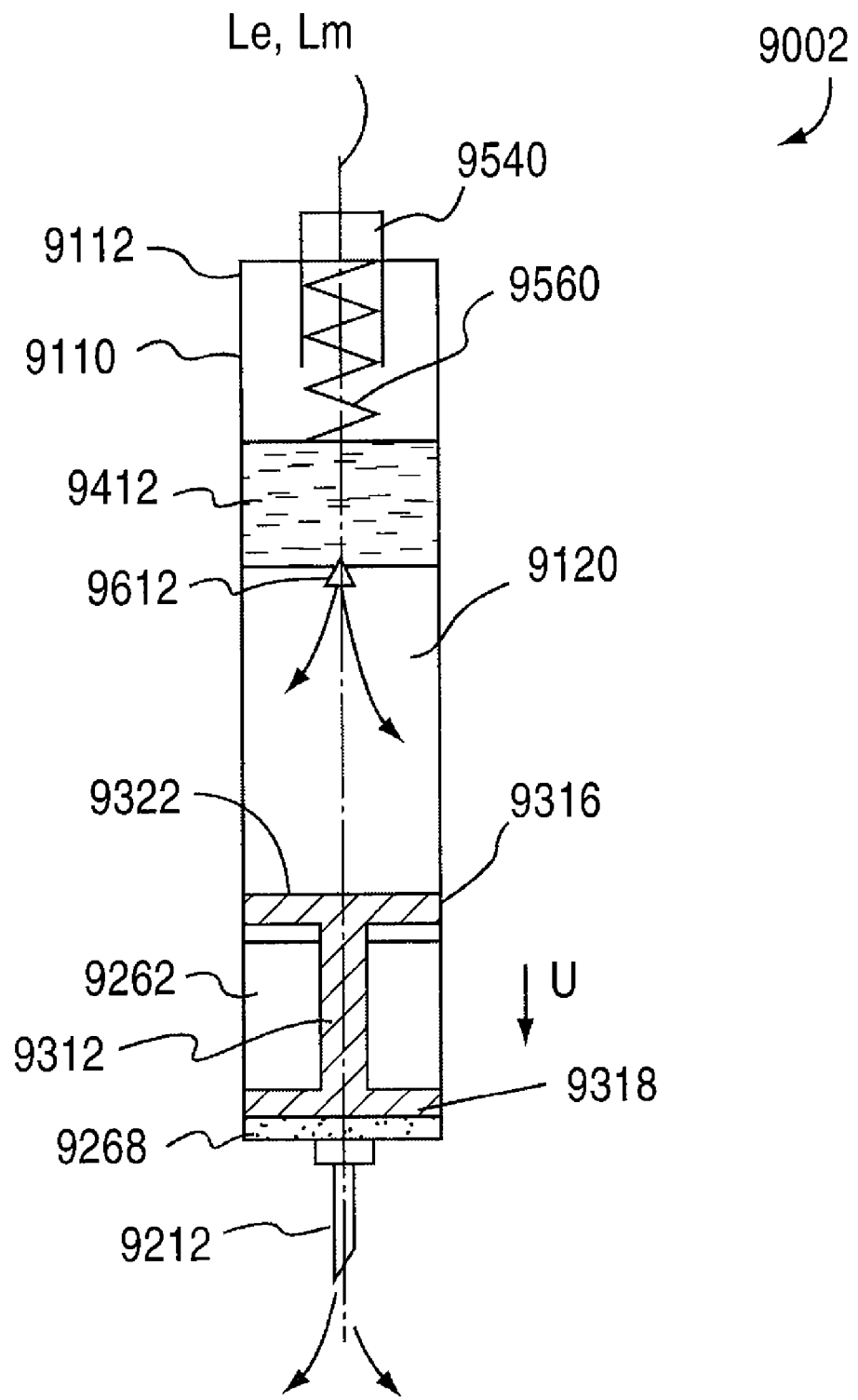

Although the auto-injector 3002 is shown and described as including a compressed gas container 3412 disposed non-coaxially with a medicament container 3262, in some embodiments, an auto-injector can include a compressed gas container that is coaxial with a medicament container. For example, FIGS. 53-55 are schematic illustrations of an auto-injector 9002 in a first configuration, a second configuration, and a third configuration, respectively. The auto-injector 9002 includes a housing 9110 that contains a medicament container 9262, a movable member 9312, a compressed gas container 9412 and a puncturer 9612. The medicament container 9262 is movably disposed within the housing 9110 and includes a needle 9212 through which a medicament 9268 can be injected. As illustrated, the medicament container 9262 can be moved along its longitudinal axis Lm between the first configuration (FIG. 53) and the second configuration (FIG. 54).

The compressed gas container 9412 is also movably disposed within the housing 9110 along its longitudinal axis Le, which is coaxial with the longitudinal axis Lm of the medicament container 9262. A biasing member 9560, such as, for example, a spring, is engaged with the compressed gas container 9412 to bias the compressed gas container 9412 distally towards the puncturer 9612. As shown in FIG. 53, when the auto-injector 9002 is in the first configuration, a retainer 9540 retains the compressed gas container 9412 in the proximal portion 9112 of the housing spaced apart from the puncturer 9612.

The movable member 9312 includes a proximal end portion 9316 and a distal end portion 9318. The proximal end portion 9316 includes a surface 9322 that, together with the housing 9110, defines a gas chamber 9120. The distal end portion 9318 is disposed within the medicament container 9262. The movable member 9312 is configured to move the medicament container 9262 within the housing 9110 and inject the medicament 9268.

In use, the auto-injector 9002 is actuated by manipulating the proximal portion 9112 of the housing 9110 to move the retainer 9540, thereby allowing the compressed gas container 9412 to be moved distally until it engages the puncturer 9612, as shown in FIG. 54. As described above, the puncturer 9612 punctures a portion of the compressed gas container 9412 thereby releasing the pressurized gas contained therein into the gas chamber 9120. The pressurized gas produces a force on the movable member 9312, which causes the movable member 9312 and the medicament container 9262 to move distally into the second configuration, as shown by the arrow T in FIG. 54. When in the second configuration, the needle 9212 is extended outside of the housing 9110. The movable member 9312 then continues to move distally within the medicament container 9262, as shown by the arrow U in FIG. 55. In this manner, the medicament is injected through the needle 9212.

Figure 56:
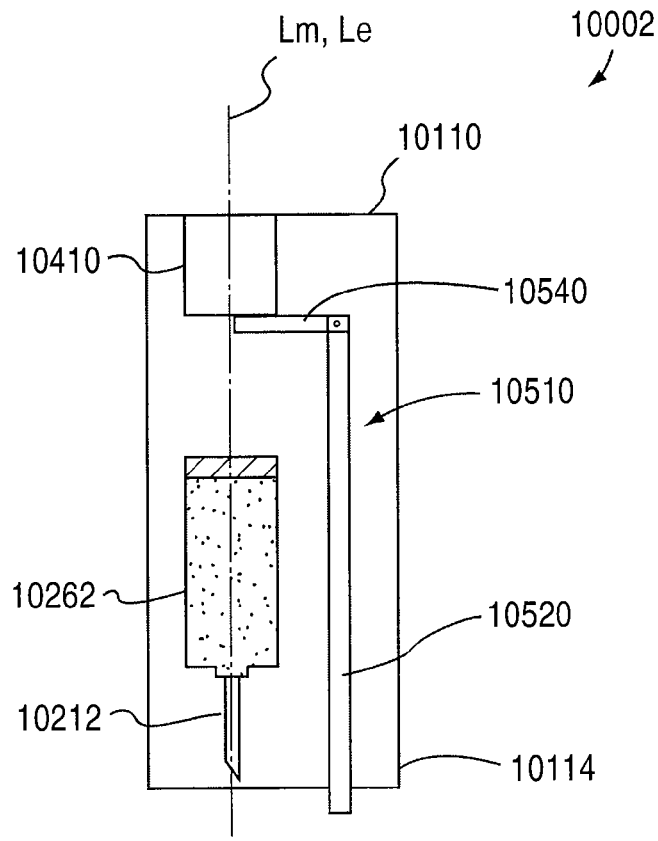
FIGS. 56 and 57 are schematic illustrations of an auto-injector according to an embodiment of the invention in a first configuration and a second configuration, respectively.
Figure 57:
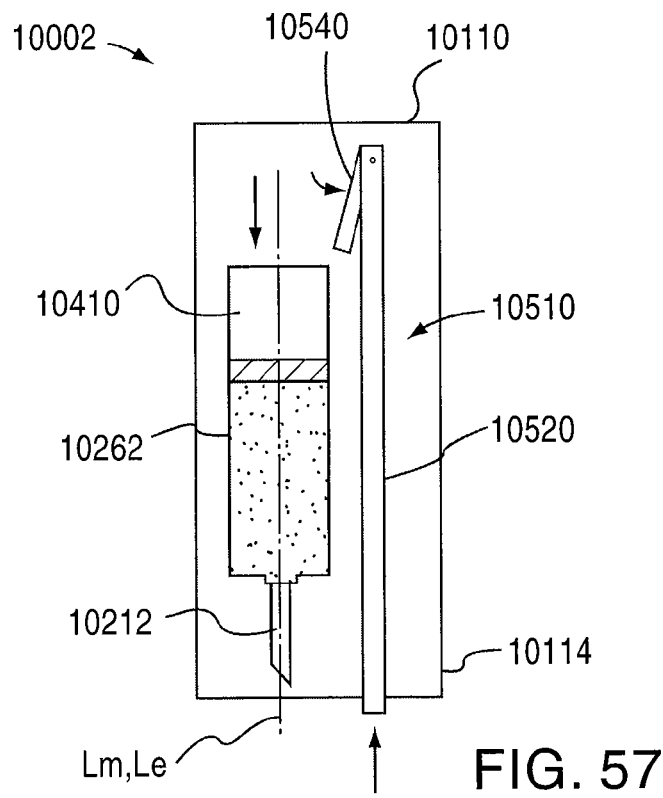

Although the auto-injectors are shown and described as being actuated from the distal end and including an energy storage member 3412 disposed non-coaxially with a medicament container 3262, in some embodiments, an auto-injector can be actuated from its distal end and include an energy storage member that is coaxial with a medicament container. For example, FIGS. 56 and 57 are schematic illustrations of an auto-injector 10002 in a first and a second configuration, respectively. The auto-injector 10002 includes a housing 10110 that contains a medicament container 10262, an energy storage member 10410 and a system actuator 10510.

The medicament container 10262 defines a longitudinal axis Lm that is coaxial with a longitudinal axis of the energy storage member 10410. The medicament container 10262 includes a needle 10212 through which a medicament can be injected. The medicament container 10262 is movable within the housing along its longitudinal axis Lm between a first position (FIGS. 56 and 57) and a second position (not shown), in which the needle 10212 extends outside of the housing 10110. As described above, the medicament container 10262 is moved by a force produced by the energy storage member 10410.

The energy storage member 10410 is also movably disposed within the housing 10110 along its longitudinal axis Le, as shown by arrow V in FIG. 57. When the energy storage member 10410 moves between a first position (FIG. 56) and a second position (FIG. 57), it produces a force on the medicament container 10262.

The system actuator 10510 includes a release member 10540 and an actuator button 10520. The release member 10540 is configured to selectively deploy the energy storage member 10410 from its first position to its second position. The release member 10540 can be, for example, a spring-loaded rod, a retainer or the like. The actuator button 10520 is coupled to the release member 10540 such that when the actuator button 10520 is manipulated, the release member 10540 can deploy the energy storage member 10410 from its first position to its second position. A portion of the actuator button 10520 extends outside of the distal end portion 10114 of the housing 10110 such that the user can actuate the auto-injector 10002 by manipulating the distal end portion 10114 of the housing 10110.

Figure 58:
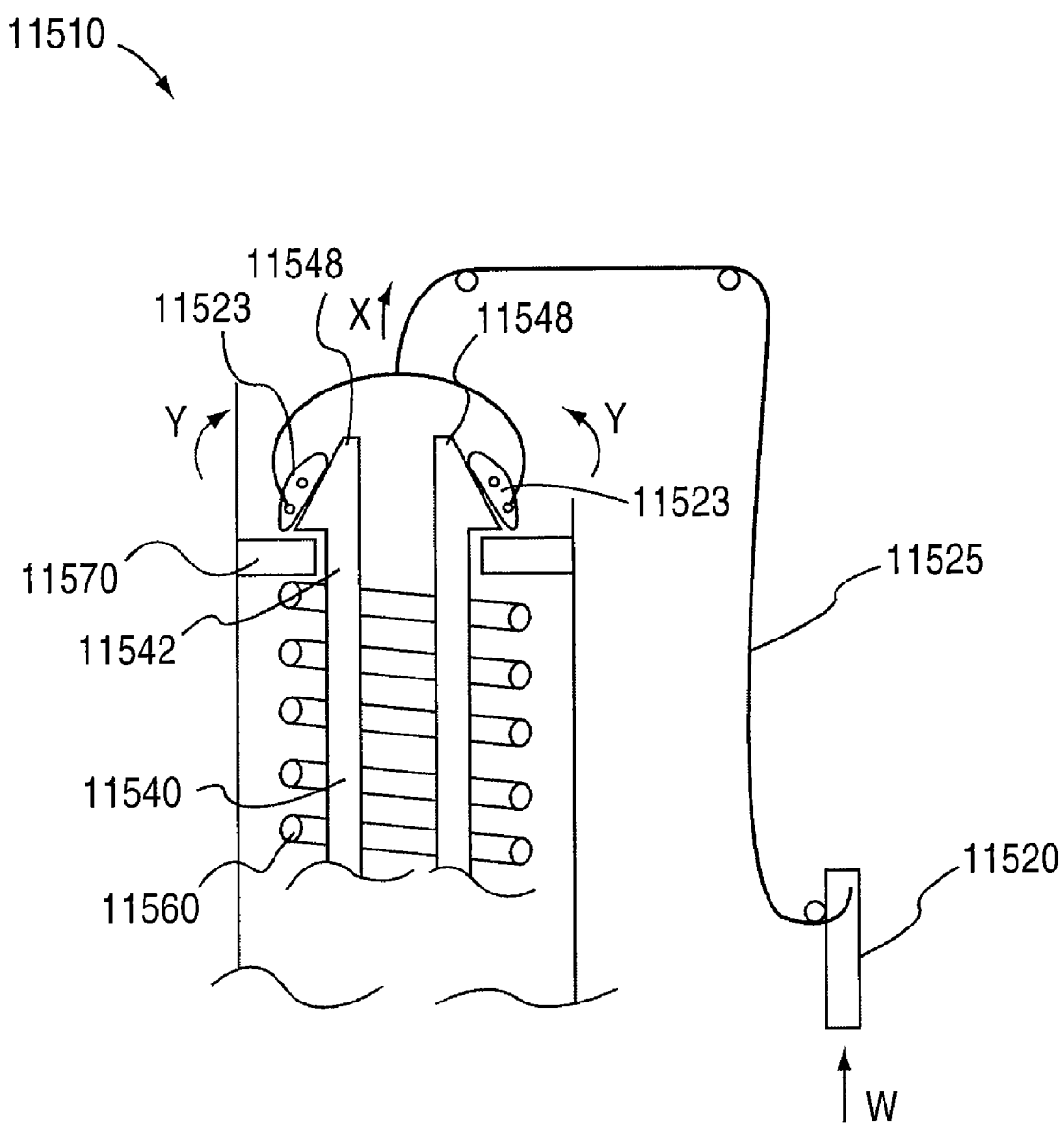
FIG. 58 is a front view of a portion of an auto-injector according to an embodiment of the invention.

FIG. 58 shows a portion of a distally actuated system actuator 11510 according to an embodiment of the invention. Similar to the system actuators shown and described above, the system actuator 11510 is configured to selectively move an energy storage member (not shown) into contact with an energy release mechanism (not shown). The system actuator 11510 includes a rod 11540, a spring 11560 and a spring retainer 11570. A proximal portion 11542 of the rod 11540 is coupled to the spring retainer 11570 by two projections 11548, which can be moved inwardly towards each other to decouple the rod 11540 from the spring retainer 11570, as previously discussed.

The spring 11560 is disposed about the rod 11540 in a compressed state such that the spring 11560 is retained by a distal end portion (not shown) of the rod 11540 and the spring retainer 11570. In this manner, the rod 11540 is spring-loaded, similar to the rod 3540 discussed above.

The system actuator 11510 also includes an actuator button 11520 that is coupled via a flexible member 11525 to a pair of pivoting members 11523. A portion of the actuator button 11520 extends outside of the distal end portion of the housing (not shown). In use, the user can actuate the auto-injector by manipulating the distal end portion of the housing, for example, by pressing the actuator button 11520 inwardly as indicated by the arrow W. The inward movement of the actuator button 11520 causes the flexible member 11525, which can be, for example, a thin cable, to move as indicated by the arrow X. The movement of the flexible member 11525 causes the pivoting members 11523 pivot as indicated by the arrows Y, which then causes the projections 11548 to move together, thereby releasing the rod 11540 from the spring retainer 11570.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although various embodiments have been described as having particular features and/or combinations of components, other embodiments are possible having a combination of any features and/or components from any of embodiments where appropriate. For example, in some embodiments, an auto-injector can include a fluidic circuit to change the direction and/or magnitude of the force produced by the energy storage member and a fluid relief valve to relieve the pressure within the fluidic circuit to assist in the retraction of the needle.

What is claimed is:

1. An apparatus, comprising:
   a housing;
   a medicament injector disposed within the housing, the medicament injector configured to inject a medicament contained therein into a body, the medicament injector including a needle, the needle defining a longitudinal axis; and
   an actuator configured to be disposed within the housing and to move the medicament injector between a first medicament injector position and a second medicament injector position, in the first medicament injector position a second end of the needle is within the housing, in the second medicament injector position the second end of the needle is outside the housing, the actuator including:
      an energy storage member having a first position and a second position, in the first position the energy storage member has a first potential energy, in the second position the energy storage member has a second potential energy less than the first potential energy, the energy storage member configured to convert a portion of the first potential energy into a kinetic energy when moved in a first direction from the first position to the second position, wherein the kinetic energy directly moves the medicament injector in a second direction between the first medicament injector position and the second medicament injector position, the second direction opposite the first direction the energy storage member having a longitudinal axis offset from the longitudinal axis of the needle; and
      a release member configured to selectively deploy the energy storage member from the first position to the second position.

2. The apparatus of claim 1, wherein the actuator is configured to move the medicament injector with a force sufficient for the needle to penetrate skin.

3. The apparatus of claim 1, wherein the energy storage member is configured to move along its longitudinal axis between the first position and the second position.

4. The apparatus of claim 1, wherein:
   the energy storage member is a gas container configured to contain a gas having a first pressure when the gas container is in the first position and a second pressure when the gas container is in the second position, the second pressure being lower than the first pressure; and
   the actuator includes a puncturer configured to penetrate a portion of the gas container when the gas container is in the second position.

5. The apparatus of claim 1, wherein:
   the medicament injector includes a medicament container; and
   the actuator is configured to move the medicament container between a first medicament container position and a second medicament container position, in the first medicament container position, a lumen defined by the needle is fluidically isolated from the medicament container, in the second medicament container position, the lumen is in fluid communication with the medicament container.

6. The apparatus of claim 1, wherein:
the medicament injector includes a medicament container; and
the actuator is configured to move the medicament container between a first medicament container position and a second medicament container position, in the first medicament container position, a lumen defined by the needle is fluidically isolated from the medicament container, in the second medicament container position, the first end of the needle is disposed within the medicament container such that the lumen is in fluid communication with the medicament container.

7. The apparatus of claim 1, wherein:
the medicament injector includes a medicament container and a movable member having a first portion and a second portion, the first portion of the movable member being configured to receive a portion of the kinetic energy produced by the energy storage member when the energy storage member moves between the first position and the second position, the second portion of the movable member being configured to move within the medicament container to expel a medicament contained within the medicament container.

8. The apparatus of claim 1, wherein the housing has a substantially rectangular shape.

9. The apparatus of claim 1, wherein the release member is movably coupled to a distal end portion of the housing.

10. The apparatus of claim 1, further comprising:
a retraction spring configured to bias the medicament injector in the first medicament injector position, a longitudinal axis of the retraction spring being offset from the longitudinal axis of the needle.

11. An apparatus, comprising:
a housing having a distal end portion and a proximal end portion;
a medicament injector disposed within the housing, the medicament injector configured to inject a medicament contained therein into a body, the medicament injector including a medicament container and a needle;
an energy storage member having first configuration and a second configuration, the energy storage member configured to produce a force when moved from the first configuration to the second configuration to move the medicament injector in a first direction between a first medicament injector position and a second medicament injector position;
a first actuation member having a first position and a second position, first actuation member configured to move the energy storage member from its first configuration to its second configuration when the first actuation member is moved in a second direction from its first position to its second position, the second direction substantially opposite the first direction, the first actuation member configured to be selectively moved from its first position to its second position by manipulating a second actuation member adjacent the distal end portion of the housing; and
a biasing member configured to bias the first actuation member.

12. The apparatus of claim 11, wherein:
when the medicament injector is in the first medicament injector position the needle is contained within the housing; and
when the medicament injector is in the second medicament injector position a portion of the needle extends from the distal end of the housing.

13. The apparatus of claim 11, wherein a longitudinal axis of the medicament container is offset from a longitudinal axis of the energy storage member.

14. The apparatus of claim 11, wherein the energy storage member is configured to move between a first position and a second position, the energy storage member being disposed in its first position when in the first configuration, the energy storage member being disposed in its second position when in the second configuration.

15. The apparatus of claim 11, wherein the energy storage member is a gas container configured to contain a gas having a first pressure when the gas container is in the first configuration and a second pressure when the gas container is in the second configuration, the second pressure being lower than the first pressure, the apparatus further comprising:
a puncturer configured to penetrate a portion of the gas container when the gas container is in the second configuration.

16. The apparatus of claim 11, wherein:
the biasing member is a spring; and
the first actuation member includes a spring retainer configured to retain the spring.

17. The apparatus of claim 11, wherein:
the biasing member is a spring; and
the first actuation member has a distal end configured to engage the distal end portion of the housing and a proximal end configured to engage the energy storage member, the first actuation member configured to be moved from its first position to its second position by disengaging the distal end of the retainer from the distal end portion of the housing by manipulating the second actuation member.

18. The apparatus of claim 11, wherein:
the biasing member is a spring configured to bias the first actuation member towards its second position; and
the first actuation member has a distal end configured to engage the distal end portion of the housing and a proximal end configured to engage the energy storage member, the first actuation member configured to be moved from its first position to its second position by moving the second actuation member inwardly towards the proximal end portion of the housing to disengage the distal end of the retainer from the distal end portion of the housing.

19. The apparatus of claim 11, wherein the second actuation member defines an opening within which a portion of the needle is disposed when the medicament injector is in the second medicament injector position.

20. The apparatus of claim 11, further comprising:
a retraction spring configured to bias the medicament injector in the first medicament injector position, a longitudinal axis of the retraction spring being offset from a longitudinal axis of the medicament container.

21. An apparatus, comprising:
a housing;
a medicament injector disposed within the housing, the medicament injector configured to inject a medicament contained therein into a body, the medicament injector including a medicament container and a needle;
a gas container configured to contain a gas, the gas container having first configuration in which the gas has a first pressure and a second configuration in which the gas has a second pressure lower than the first pressure, the gas container configured to produce a force when moved from the first configuration to the second configuration to move the medicament injector between a first medicament injector position and a second medicament injector position, a longitudinal axis of the gas container being noncoaxial with a longitudinal axis of the medicament container;

a puncturer configured to penetrate a portion of the gas container when the gas container is in the second configuration; and a retraction spring configured to bias the medicament injector in the first medicament injector position, the retraction spring configured to exert a biasing force along an axis noncoaxial with the longitudinal axis of the medicament container.

22. The apparatus of claim 21, further comprising:

an actuation member having a first position and a second position, the actuation member configured to move the gas container from its first configuration to its second configuration when the actuation member is moved from its first position to its second position, the actuation member configured to be selectively moved from its first position to its second position by manipulating a distal end portion of the housing.

23. The apparatus of claim 21, further comprising:

an actuation member having a first position and a second position, the actuation member configured to move the gas container from its first configuration to its second configuration when the actuation member is moved from its first position to its second position, the actuation member configured to be selectively moved from its first position to its second position by manipulating a distal end portion of the housing; and a biasing member configured to bias the actuation member.

24. The apparatus of claim 21, wherein:

when the medicament injector is in the first medicament injector position the needle is contained within the housing; and when the medicament injector is in the second medicament injector position a portion of the needle extends from a distal end of the housing.

25. The apparatus of claim 21, wherein the gas container is configured to move between a first position and a second position, the gas container being disposed in its first position when in the first configuration, the gas container being disposed in its second position when in the second configuration.

26. The apparatus of claim 21, wherein:

the medicament injector includes a medicament container; and the force is configured to move the medicament container between a first medicament container position and a second medicament container position, a lumen defined by the needle is fluidically isolated from the medicament container when the medicament container is in the first medicament container position, the lumen being in fluid communication with the medicament container, when the medicament container is in the second medicament container position.

* * * * *

UNITED STATES PATENT AND TRADEMARK OFFICE
CERTIFICATE OF CORRECTION

PATENT NO.        : 7,648,482 B2
APPLICATION NO.   : 11/562061
DATED             : January 19, 2010
INVENTOR(S)       : Edwards et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 376 days.

Signed and Sealed this

Twenty-third Day of November, 2010

David J. Kappos
*Director of the United States Patent and Trademark Office*